US009499615B2

(12) United States Patent
Hoffman et al.

(10) Patent No.: US 9,499,615 B2
(45) Date of Patent: *Nov. 22, 2016

(54) MULTIPLE-VARIABLE DOSE REGIMEN FOR TREATING IDIOPATHIC INFLAMMATORY BOWEL DISEASE

(71) Applicant: AbbVie Biotechnology Ltd, Hamilton (BM)

(72) Inventors: Rebecca S. Hoffman, Wilmette, IL (US); Elliot K. Chartash, Randolph, NJ (US); Lori K. Taylor, Wadsworth, IL (US); George R. Granneman, Lindenhurst, IL (US); Philip Yan, Vernon Hills, IL (US)

(73) Assignee: ABBVIE BIOTECHNOLOGY LTD, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,164

(22) Filed: Jul. 20, 2015

(65) Prior Publication Data

US 2016/0185849 A1   Jun. 30, 2016

Related U.S. Application Data

(63) Continuation of application No. 14/628,068, filed on Feb. 20, 2015, now Pat. No. 9,187,559, which is a continuation of application No. 14/229,664, filed on Mar. 28, 2014, now Pat. No. 8,961,973, which is a continuation of application No. 11/104,117, filed on Apr. 11, 2005, now Pat. No. 8,889,136.

(60) Provisional application No. 60/569,100, filed on May 7, 2004, provisional application No. 60/561,710, filed on Apr. 12, 2004, provisional application No. 60/561,139, filed on Apr. 9, 2004.

(51) Int. Cl.
*A61K 39/395* (2006.01)
*C07K 16/24* (2006.01)
*A61K 9/00* (2006.01)
*A61K 39/00* (2006.01)

(52) U.S. Cl.
CPC .......... *C07K 16/241* (2013.01); *A61K 9/0019* (2013.01); *A61K 39/3955* (2013.01); *A61K 2039/505* (2013.01); *A61K 2039/545* (2013.01); *C07K 2316/96* (2013.01); *C07K 2317/21* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,231,024 A | 7/1993 | Moeller et al. |
| 5,654,407 A | 8/1997 | Boyle et al. |
| 5,795,967 A | 8/1998 | Aggarwal et al. |
| 5,859,205 A | 1/1999 | Adair et al. |
| 5,877,293 A | 3/1999 | Adair et al. |
| 5,929,212 A | 7/1999 | Jolliffe et al. |
| 5,994,510 A | 11/1999 | Adair et al. |
| 6,090,382 A | 7/2000 | Salfeld et al. |
| 6,214,870 B1 | 4/2001 | McClure et al. |
| 6,235,281 B1 | 5/2001 | Stenzel et al. |
| 6,258,562 B1 | 7/2001 | Salfeld et al. |
| 6,270,766 B1 | 8/2001 | Feldman et al. |
| 6,509,015 B1 | 1/2003 | Salfeld et al. |
| 6,627,196 B1 | 9/2003 | Baughman et al. |
| 6,732,589 B2 | 5/2004 | Eickhoff et al. |
| 7,223,394 B2 | 5/2007 | Salfeld et al. |
| 7,250,165 B2 | 7/2007 | Heavner et al. |
| 7,541,031 B2 | 6/2009 | Salfeld et al. |
| 7,588,761 B2 | 9/2009 | Salfeld et al. |
| 7,863,426 B2 | 1/2011 | Wan et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pia et al. |
| 8,187,836 B2 | 5/2012 | Hsieh et al. |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |

(Continued)

FOREIGN PATENT DOCUMENTS

| | | |
|---|---|---|
| CA | 2243459 | 8/1997 |
| CA | 2 803741 | 1/2004 |

(Continued)

OTHER PUBLICATIONS

Adalimumab U.S. Product Label, Sep. 2003, 18 pages.*

(Continued)

*Primary Examiner* — Zachary Skelding
(74) *Attorney, Agent, or Firm* — Ropes & Gray LLP; Karen Mangasarian; Brian M. Gummow

(57) ABSTRACT

Multiple-variable dose methods for treating TNFα-related disorders, including Crohn's disease and psoriasis, comprising administering TNFα inhibitors, including TNFα antibodies, are described. Multiple-variable dose methods include administration of a TNF-inhibitor in an induction or loading phase followed by administration of the agent in a maintenance or treatment phase, wherein the TNF-inhibitor is administered in a higher dosage during the induction phase.

28 Claims, 10 Drawing Sheets

(56) References Cited

U.S. PATENT DOCUMENTS

| | | |
|---|---|---|
| 8,436,149 B2 | 5/2013 | Borhani et al. |
| 8,889,136 B2 | 11/2014 | Hoffman et al. |
| 8,961,973 B2 | 2/2015 | Hoffman et al. |
| 8,961,974 B2 | 2/2015 | Hoffman et al. |
| 9,061,005 B2 | 6/2015 | Hoffman et al. |
| 2002/0022720 A1 | 2/2002 | Le et al. |
| 2003/0012786 A1 | 1/2003 | Teoh et al. |
| 2003/0049725 A1 | 3/2003 | Heavner et al. |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0123541 A1 | 6/2005 | Heavner et al. |
| 2005/0249735 A1 | 11/2005 | Le et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0153846 A1 | 7/2006 | Krause |
| 2006/0246073 A1 | 11/2006 | Knight et al. |
| 2007/0003548 A1 | 1/2007 | Heavner et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0202104 A1 | 8/2007 | Banerjee et al. |
| 2007/0249813 A1 | 10/2007 | Salfeld et al. |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0311043 A1 | 12/2008 | Hoffman et al. |
| 2009/0017472 A1 | 1/2009 | Stuhlmuller |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmller et al. |
| 2012/0077213 A1 | 3/2012 | Pia et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0258114 A1 | 10/2012 | Salfeld et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |

FOREIGN PATENT DOCUMENTS

| | | |
|---|---|---|
| CA | 2493067 | 1/2004 |
| EP | 0 101 681 | 3/1984 |
| EP | 0 186 833 | 7/1986 |
| EP | 0 212 489 | 3/1987 |
| EP | 0 230 574 | 8/1987 |
| EP | 0 260610 | 3/1988 |
| EP | 0 351 789 | 1/1990 |
| EP | 0 366 043 | 5/1990 |
| EP | 0 374 510 | 6/1990 |
| EP | 0 377 823 | 7/1990 |
| EP | 0 453898 | 10/1991 |
| EP | 0 492 448 | 7/1992 |
| EP | 0 585705 | 3/1994 |
| EP | 0 614 984 | 9/1994 |
| EP | 0 659 766 | 6/1995 |
| EP | 1 232 753 | 8/2002 |
| GB | 2 279 077 | 12/1994 |
| WO | WO 91/02078 | 2/1991 |
| WO | WO 91/04054 | 4/1991 |
| WO | WO 91/09967 | 7/1991 |
| WO | WO 92/11383 | 7/1992 |
| WO | WO 92/16221 | 10/1992 |
| WO | WO 92/16553 | 10/1992 |
| WO | WO 92/17583 | 10/1992 |
| WO | WO 93/06213 | 4/1993 |
| WO | WO 93/11793 | 6/1993 |
| WO | WO 93/19751 | 10/1993 |
| WO | WO 94/29347 | 12/1994 |
| WO | WO 95/23813 | 9/1995 |
| WO | WO 96/33204 | 10/1996 |
| WO | WO 97/29131 | 8/1997 |
| WO | WO 98/04281 | 2/1998 |
| WO | WO 98/05357 | 2/1998 |
| WO | WO 01/00229 | 1/2001 |
| WO | WO 01/37874 | 5/2001 |
| WO | WO 02/02773 | 1/2002 |
| WO | WO 02/100330 | 12/2002 |
| WO | WO 2004/009776 | 1/2004 |
| WO | WO 2004/016286 | 2/2004 |
| WO | WO 2004/092448 | 10/2004 |
| WO | WO 2006/041970 | 4/2006 |

OTHER PUBLICATIONS

Mease, "Etanercept, a TNF antagonist for treatment for psoriatic arthritis and psoriasis," Skin Therapy Lett, 8(1):1-4 (2003).

Goffe et al. "Etanercept: an overview," Journal of the American Academy of Dermatology, 49(2):S105-S111 (2003).

Marzo-Ortega et al., Infliximab is effective in the treatment of resistant psoriatic arthritis and skin psoriasis: A clinical and MRI study, Biological Abstract, Osteoporosis, OP11, (Jan. 4, 2002).

Emma Hitt, PhD: "Adalimumab Effective for Psoriasis", Feb. 10, 2004 (Feb. 10, 2004), Retrieved from the Internet: URL:www.medscape.com/viewarticle/468942_print (EP_Opp_D19).

Nigel Bates: "Cambridge Antibody Technology and Genzyme Announce Preliminary Results From Phase 1/11 Trial of Cat-192 for Scleroderma", www.siliconinvestor.com, Feb. 9, 2004 (Feb. 9, 2004), Retrieved from the Internet: URL:??? (EP_Opp_D20).

(56) References Cited

OTHER PUBLICATIONS

Abbott Laboratories: "ABT Announces Positive Result", Feb. 9, 2004 (Feb. 9, 2004), Retrieved from the Internet: URL:http://www.investegate.co.uklarticlePrint.aspc?id=200402091648151924V [retrieved on Oct. 13, 2015] (EP_Opp_D21).
Abbott Laboratories Announces Positive Results of Phase II Humira® (Adalimumab) Study in Psoriasis, EvaluatePharma, Feb. 9, 2004 (Feb. 9, 2004), Retrieved from the Internet: URL:??? (EP_Opp_D22).
"Adalimumab has achieved significant reductions in disease activity in patients with moderate-to-severe chronic plaque psoriasis", Inpharma 1424, Feb. 14, 2004, (Feb. 14, 2004), Retrieved from the Internet: URL:??? (EP-Opp_D23).
"Abbott Laboratories Announces Positive Results of Two Clinical Trials of HUMIRA (adalimumab) in Crohn's Disease," Press Release May 18, 2004.
Abbott Laboratories Press Release of Jan. 6, 2003, "Abbott Laboratories Receives FDA Approval Earlier Than Anticipated for Humira TM (Adalimumab) for the Treatment of Rheumatoid Arthritis (RA)," pp. 1-4.
Abbott Provisional Assignment (2005) (5 pages).
Abraham, E. et al., "Efficacy and Safety of Monoclonal Antibody to Human Tumor Necrosis Factor α in Patients with Sepsis Syndrome," JAMA, vol. 273(12):934-941 (1995).
Abraham, E., "Why Immunomodulatory Therapies Have Not Worked in Sepsis," Intensive Care Med., vol. 25:556-566 (1999).
Abstract #435 to the Talk by Sandborn et al. at the Digestive Disease Week and the 105th Annual Meeting of the American Gastroenterological Association held on May 15-20, 2004; Published in a Supplement to Gastroenterology 126 (2004).
Adalimumab Product Label, Abbott Laboratories, North Chicago, IL 60064, Dec. 20, 2002, 1-16.
Adalimumab U.S. Product Label of the Product (Dec. 2002) (16 pages).
Advisory Committee Briefing Document HUMIRA™ (Adalimumab), Document Dated Feb. 4, 2003, Advisory Meeting Date Mar. 4, 2003.
Afif et al., "Clinical Utility of Measuring Infliximab and Human Anti-Chimeric Antibody Concentrations in Patients With Inflammatory Bowel Disease," American Journal Gastroenterology, vol. 105:1133-1139 (2010).
Aggarwal, Bharat B., "Signalling Pathways of the TNF Superfamily: A Double-Edged Sword," Nature Reviews, 3:745-756 (2003).
Agnholt et al., Infliximab Downregulates Interferon-γ Production in Activated Gut T-Lymphocytes from Patients with Crohn's Disease, CYTOKINE, 15(4):212-222 (2001).
American Thoracic Society "Idiopathic pulmonary fibrosis: diagnosis and treatment," Am. J. Respir. Crit. Care Med. vol. 161, p. 646-664 (2000).
Anticevich et al., "Induction of human airway hyperresponsiveness by tumour necrosis factor-α," Eur J Pharmacol. vol. 284, p. 221-225 (1995).
Asakura H. et al., "Colonic Inflammation and Tumors: Clinical and Clinicopathological Studies," J. of Gastroenterology Studies, vol. 16:763-769 (2001).
Aulton M., "Dosage Regimens: Their Influence on the Concentration-Time Profile of a Drug in the Body," Pharmaceutics: The Science of Dosage Form Design, 2nd Ed., Chapter 19, pp. 276-288 (2001).
AusPAR Attachment 2, "Extract from the Clinical Evaluation Report for Adalimumab," Australian Government, Dept of Health, Therapeutic Goods Administration (86 pages) (Date of Cer: Mar. 28, 2013).
Awni et al., "Pharmacokinetics of Adalimumab in Adult Patients with Moderately to Severely Active Ulcerative Colitis," Feb. 6, 2013 (1 page).
Awni, W. et al., "Steady-State Pharmacokinetics (PK) of Adalimumab (HUMIRA ™, Abbott) Following 40 mg Subcutaneous (SC) Injection Every Other Week (EOW) in Rheumatoid Arthritis (RA) Patients with and without Methotrexate (MTX) Background Therapy," Arthritis Rheum., vol. 48(Suppl. 9):5140 (2003).
Baeder et al., "Rapamycin prevents the onset of insulin-dependent diabetes mellitus (IDDM) in NOD mice," Clin Exp Immunol. vol. 89, p. 174-178 (1992).
Baert F. et al., "Influence of Immunogenicity on the Long-Term Efficacy of Infliximab in Crohn's Disease," N. Engl. J. Med., 348:601-608 (2003).
Bailey et al. "Influence of genetic background and age in the expression of the obese hyperglycaemic syndrome in Aston ob/ob mice," Int. J. Obesity vol. 6, p. 11-21 (1982).
Bang et al., "Adalimumab—A Review of its Use in Rheumatoid Arthritis," ADIS Drug Evaluation, Biodrugs, 18(2):121-139 (2004).
Barbieri et al., "Is Chronic inflammation a determinant of blood pressure in the elderly?," Am J Hypertens vol. 16, p. 537-543 (2003).
Barbuto, J. A. M. et al., "Production of Neutralizing Antibodies to Tumor Necrosis Factor by Human Tumor-Infiltrating B Lymphocytes," Proc. Am. Assoc. Cancer Res., 34:487, Abstr. 2904 (1993).
Barrera, P. et al., "Drug Survival, Efficacy and Toxicity of Monotherapy with a Fully Human Anti-Tumour Necrosis Factor-α Antibody Compared With Methotrexate in Long-Standing Rheumatoid Arthritis," Rheumatology, vol. 41:430-439 (2002).
Barrera, P. et al., "Effect of a Fully Human Anti-TNFα Monoclonal Antibody on the Local and Systemic Expression of TNFα and IL-β," Arthritis Rheum., vol. 42(9 Suppl.):575 (1999).
Beenhouwer et al., "Mechanisms of Action of Tumor Necrosis Factor Antagonists and Granulomatous Infections," The Journal of Rheumatology, 31(10):1888-1892 (2004).
Bendtzen et al. "Auto-antibodies to IL-1α and TNFα in Normal Individuals and in Infectious and Immunoinflammatory Disorders," The Physiological and Pathological Effects of Cytokines, pp. 447-452 (1990).
Bendtzen et al., "Individual medicine in inflammatory bowel disease: monitoring bioavailability, pharmacokinetics and immunogenicity of anti-tumour necrosis factor-alpha antibodies," Scand J Gastroenterol., vol. 44(7):774-81 (2009) (abstract supplied—1 page).
Ben-Horin et al., "The immunogenic part of infliximab is the F(ab')2, but measuring antibodies to the intact infliximab molecule is more clinically useful," GUT, vol. 60(1):41-48 (2011).
Benjafield et al., "TNFRSF1B in genetic predisposition to the clinical neuropathy and effect on HDL cholesterol and glycosylated hemoglobin in type 2 diabetes," Diabetes Care vol. 24, p. 753-757 (2001).
Bennett; Zie, "A peripheral mononeuropathy in rat that produces disorders of pain sensation like those seen in man," Pain vol. 33, pp. 87-107 (1988).
Berk; Harris, "Restenosis after percutaneous transluminal coronary angioplasty: new therapeutic insights from pathogenic mechanisms," Adv. Intern. Med. vol. 40, p. 455-500 (1995).
Bermejo et al., "Infliximab induces clinical, endoscopic and histological responses in refractory ulcerative colitis," Rev Esp Enferm Dig (Madrid), 96:92-101 (2004).
Bieber et al., "Tuberculosis and opportunistic infections: Relevance to biologic agents," Clin Exp. Rheumatol 22:(suppl. 35) S-126-S-133 (2004).
Boekstegers, P., et al., "Repeated Administration of a F(ab')2 Fragment of an Anti-Tumor Necrosis Factor Alpha Monoclonal Antibody in Patients With Severe Sepsis: Effects on the Cardiovascular System and Cytokine Levels," Shock, vol. 1(4):237-245 (1994).
Bombardier, C. et al., "Pattern of DMARD use in a North American Cohort of Patients with Early Rheumatoid Arthritis (RA) (SONORA)," Arthritis Rheum., vol. 46(9 Suppl.):5344 (2002).
Bongartz et al., "Anti-TNF Antibody Therapy in Rheumatoid Arthritis and the Risk of Serious Infections and Malignancies, Systematic Review and Meta-analysis of Rare Harmful Effects of Randomized Controlled Trials," JAMA, 295(21):2275-2482 (2006).
Boyle, P. et al., "A Novel Monoclonal Human IgM Autoantibody which Binds Recombinant Human and Mouse Tumor Necrosis Factor—α," Cell. Immunol., 152:556-568 (1993).

(56) References Cited

OTHER PUBLICATIONS

Boyle, P. et al., "The B5 Monoclonal Human Autoantibody Binds to Cell Surface TNFα on Human Lymphoid Cells and Cell Lines and Appears to Recognize a Novel Epitope," Cell. Immunol., 152:569-581 (1993).

Braun et al., "Low secretion of tumor necrosis factor α, but no other Th1 or Th2 cytokines, by peripheral blood mononuclear cells correlates with chronicity in reactive arthritis," Arthritis Rheum. vol. 42, No. 10, p. 2039-2044 (1999).

Braun, J. et al., "Novel Approaches in the Treatment of Ankylosing Spondylitis and Other Spondyloarthritides," Expert Opin. Investig. Drugs, 12:1097-1109 (2003).

Breedveld, F. et al., "Sustained Efficacy Over 4 Years with Adalimumab in Patients with Active Rheumatoid Arthritis," Ann. Rheum. Dis., vol. 62(Suppl. 1):169 (2003).

Breedveld, F. et al., "Sustained Efficacy over 5 Years with Adalimumab (HUMIRA ™) in Patients with Active Rheumatoid Arthritis," Arthritis Rheum., vol. 48(Suppl. 9):S118 (2003).

Breedveld, F. et al., "The Fully Human Anti-TNF Antibody Adalimumab (D2E7) in Combination with Methotrexate (MTX) in the Treatment of Active Rheumatoid Arthritis: Results of a 2-Year Study," Presented at: The Annual Meeting of the European League Against Rheumatism (EULAR), Prague, Czech Republic, Jun. 2001.

Breedveld, F. et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," JCR: Journal of Clinical Rheumatology, vol. 8(Suppl. 3):546 2 pages, (2002).

Brekke, Ole Henrik et al., "Therapeutic Antibodies for Human Diseases at the Dawn of the Twenty-first Century," Nature, vol. 2:52-62 (2002).

Brouwer et al., "Antimyeloperoxidase-associated proliferative glomerulonephritis: an animal model," J Exp. Med. vol. 177, p. 905-914 (1993).

Brown et al., "Tumor Necrosis Factor Antagonist Therapy and Lymphoma Development," Arthritis & Rheumatism 46(12):3151-3158 (2002).

Burmester, G. et al., "Long-Term Efficacy and Safety of Adalimumab (D2E7) Monotherapy in Patients With DMARD-Refractory Rheumatoid Arthritis—Results From a 2-Year Study," Arthritis Rheum., vol. 46(9 Suppl.):S537 (2002).

Burmester, G. et al., "Sustained Efficacy of Adalimumab Monotherapy for More than Four Years in DMARD-Refractory RA," Ann. Rheum. Dis., vol. 62(Suppl. 1):192-3 (2003).

Business Wire, Biogen Idec and Elan Announce Voluntary Suspension of TYSABRI-R-, press release Feb. 28, 2005 (3 pages).

Callen, "New Psoriasis Treatments Based Upon a Deeper Understanding of the Pathogenesis of Psoriasis Vulgaris and Psoriatic Arthritis: A Personal Appraisal of Their Use in Practice," J. Am. Acad. Deramatol., 49:351-356 (2003).

Case, John P., "Old and New Drugs Used in Rheumatoid Arthritis: A Historical Perspective," American Journal of Therapeutics, vol. 8:163-179 (2001).

Cassinotti et al., "Adalimumab for the treatment of Crohn's disease," Biologics: Targets & Therapy, 2(4):763-777 (2008).

Casteele et al., "Antibody Response to Infliximab and its Impact on Pharmacokinetics can be Transient," The American Journal of Gastroenterology, vol. 108:962-971 (2013).

Challenges in Crohn's Disease, Gastroenterology, vol. 4, Supplement 3, 2004 (1 page).

Chartash, E. et al., "Adalimumab Improves Fatigue in Patients with Active Rheumatoid Arthritis," Ann. Rheum. Dis., vol. 62(Suppl. 1):349 (2003).

Cheifetz et al., "The Incidence and Management of Infusion Reactions to Infliximab: A Large Center Experience," The American Journal of Gastroenterology, vol. 98(6):1315-1324 (2003).

Chen, D. et al., "Adalimumab Efficacy and Safety in Patients with Moderate to Severe Chronic Plaque Psoriasis: Preliminary Findings From a 12-Week Dose-Ranging Trial," Supplement to the J. Am. Acad. of Dermatol., 50(3):P1 (2004).

Chiu et al., "Serum Adalimumab Concentration and Clinical Remission in Patients with Crohn's Disease," Inflamm Bowel Dis, vol. 19(6):1112-1122 (2013).

Chow, A. et al., "Effect of Monoclonal Antibody on Human Tumor Necrosis Factor (TNF MAb) on TNFα, IL-1β, and IL-6 levels in patients with sepsis syndrome," Clinical Research, 42(2)299A (1994).

Chu "Glycemic status and soluble tumor necrosis factor receptor levels in relation to plasma leptin concentration among normal weight and overweight US men," Int J Obes Relat Metab Disord vol. 24, p. 1085-1092 (2000).

Clagett et al., "morphogenesis and clinicopathologic characteristics of recurrent carotid disease," J. Vasc. Surg. vol. 3, p. 10-23 (1986).

Clausell et al. "Increased expression of tumor necrosis factor-α in diabetic macrovasculopathy," Cardiovasc Pathol. vol. 8, p. 145-151 (1999).

Clowes et al., "Mechanisms of stenosis after arterial injury," Lab. Invest. vol. 49, p. 208-215 (1983).

Coccia et al., "Novel erythropoiesis stimulating protein (darbepoetin alfa) alleviates anemia associated with chronic inflammatory disease in a rodent model," Exp Hematology vol. 29, pp. 1201-1209 (2001).

Coelho et al., Systemic lipopolysaccharide influences rectal sensitivity in rats: role of mast cells, cytokines, and vagus nerve, Am J Physiol Gastrointest Liver Physiol. vol. 279, p. G781-G790 (2000).

Cohen, Jonathan, et al., "Intersept: An international, Multicenter, Placebo-Controlled Trial of Monoclonal Antibody to Human Tumor Necrosis Factor-α in Patients with Sepsis," Crit. Care Med., vol. 24(9):1431-1440 (1996).

Colburn; Moore: 'Myointimal Hyperplasia', in 'Vascular Surgery: A Comprehensive Review Philadelphia', 1998, Saunders pp. 690-709.

Coleman, "Obese and diabetes: two mutant genes causing diabetes-obesity syndromes in mice," Diabetologia vol. 14, p. 141-148 (1978).

Colletti et al., "Role of tumour necrosis factor-α in the pathophysiologic alteration after hepatic ischemia/reperfusion injury in the rat," J Clin Invest. vol. 85, p. 1936-1943 (1990).

Colman, P. "Effects of Amino Acid Sequence Changes on Antibody-Antigen Interactions," Research in Immunology, vol. 145(1):33-36 (1994).

Colombel et al., "P182. Impact of Induction Dosing on Maintenance Outcome With Adalimumab in Crohn's Disease," (Handout) Clinical Therapy and observation, European Crohn's and Colitis Organisation (Feb. 24-26, 2011) (4 pages).

Colombel Jean-Frederic et al., "The Safety Profile of Infliximab in Patients With Crohn's Disease: The Mayo Clinic Experience in 500 Patients," Gastroenterology, 126:19-31 (2004).

Cox, J. P. L. et al., "A Directory of Human Germ-Line VK Segments Reveals a Strong Bias in Their Usage," Eur. J. Immunol., 24(2):827-36 (1994).

Daimon et al., "Decreased serum levels of adiponectin are a risk factor for the progression to type 2 diabetes in the Japanese population," Diabetes Care. vol. 26, p. 2015-2020 (2003).

Demeter et al. "Clinical relevance of the TNF-alpha promoter/enhancer polymorphism in patients with aplastic anemia," Ann Hematol. vol. 81, p. 566-569 (2002).

den Broeder A. et al., "Dose Titration Using the Disease Activity Score (DAS28) in Rheumatoid Arthritis Patents Treated with Anti-TNF-α," Rheumatology, 41:638-642 (2002).

den Broeder, A. et al, "The Effect of D2E7, a New Human Anti-TNFα Monoclonal Antibody, on the Oxidative Burst of PMN in Patients With RA," Arthritis and Rheumatism, 41(9):557 (1998).

den Broeder, A. et al., "A Single Dose, Placebo Controlled Study of the Fully Human Anti-Tumor Necrosis Factor-α Antibody Adalimumab (D2E7) in Patients with Rheumatoid Arthritis," The Journal of Rheumatology, vol. 29(11):2288-2298 (2002).

den Broeder, A.A. et al., "Long term anti-tumour necrosis factor α monotherapy in rheumatoid arthritis: effect on radiological course and prognostic value of markers of cartilage turnover and endothelial activation," Ann. Rheum. Dis., vol. 61:311-318 (2002).

(56) References Cited

OTHER PUBLICATIONS

Department of Surgery, University of Toronto, Annual Report (1998-1999).
Devaraj et al., "Low density lipoprotein postsecretory modification, monocyte function and circulating adhesion molecules in type 2 diabetic patients with and without macrovascular complications: the effect of α-tocopherol supplementation," Circulation vol. 102, p. 191-196 (2000).
Dicato, "Anemia and cancer: some pathophysiological aspects," The Oncologist vol. 8, No. 1, p. 19-21 (2003).
Ding, T. & Deighton, C., "Complications of anti-TNF therapies," Future Rheumatol., 2(6):587-597 (2007).
Doring et al., "Identification and Characterization of a TNFα Antagonist Derived from a Monoclonal Antibody," Mol. Immunol., 31(14):1059-1067 (1994).
Dotan et al., "Population Pharmacokinetic Evaluation of Adalimumab Reveals Patient Factors that Increase Adalimumab Clearance and Shorten Half-Life in Inflammatory Bowel Disease Patients," American Gastroenterological Association Poster (2014).
Duffy et al. "Effect of nimesulfide on cox-1 and cox-2 expression and related prostanoid formation in patients with acute knee inflammation," Am Coll. Rheumato. 66th Annual Scientific Meeting, abstract 342, (Oct. 24-29, 2002).
Eason et al. "Inhibtion of the effects of TNF in renal allograft recipients using recombinant human dimeric tumor necrosis factor receptors," Transplantation vol. 59, p. 300-305 (1995).
Eckardt et al., "Pure red-cell aplasia due to anti-erythropoietin antibodies," Nephrol Dial Transplant 18:865-869 (2003).
Eckert et al., "Pharmacokinetics of Adalimumab in Paediatric Patients with Moderate to Severe Crohn's Disease," Feb. 6, 2013 (1 page).
Egan et al., "Advances in the Treatment of Crohn's Disease," Gastroenterology, 126(6):1574-1581 (2004).
Egan, L. et al, "A Randomized, Single-Blind, Pharmacokinetic and Dose Response Study of Subcutaneous Methotrexate, 15 and 25 Mg/week, for Refractory Ulcerative Colitis and Crohn's Disease," Gastroenterology, vol. 114(4):G3978 (1998).
Elliot, M.J. et al., "Randomised double-blind comparison of chimeric monoclonal antibody to tumour necrosis factor α (cA2) versus placebo in rheumatoid arthritis," Lancet vol. 344, pp. 1105-1110 (1994).
Elliott, M. et al. "Treatment of Rheumatoid Arthritis with Chimeric Monoclonal Antibodies to Tumor Necrosis Factor α," Arthritis and Rheumatism, 36(12):1681-1690 (1993).
Elliott, M.J. "Repeated therapy with monoclonal antibody to tumour necrosis factor (cA2) in patients with rheumatoid arthritis," Lancet vol. 344, pp. 1125-1127 (1994).
EMEA European Agency for the Evaluation of Medicinal Products, Points to Consider on Clinical Investigation of Medicinal Products for the Management of Crohn's Disease, CPMP/EWP/2284/99, Jun. 27, 2001 (6 pages).
EMEA European Medicines Agency, Concept Paper on the Revision of the CHMP Points to Consider on Clinical Investigation of Medicinal Products for the Management of Crohn's Disease, Doc. Ref. CHMP/EWP/18446/2006, Jan. 26, 2006 (4 pages).
EMEA European Medicines Agency, Guideline on the Development of New Medicinal Products for the Treatment of Crohn's Disease, Doc. Ref. CPMP/EWP/2284/99, Jul. 24, 2008 (11 pages).
EMEA European Medicines Agency, Guideline on the Development of New Medicinal Products for the Treatment of Crohn's Disease, Draft, Doc. Ref. CPMP/EWP/2284/99 Rev. 1, Feb. 22, 2007 (8 pages).
Emery, Paul et al., "Changes in PRO-MMP-1 in Relation to Standard Measures of Disease Activity Over a 6 Month Treatment Period with Adalimumab (D2E7) in Rheumatoid Arthritis," Arthritis & Rheumatism, vol. 44(9):S215 (2001).
Empl et al., "TNF-alpha expression in painful and nonpainful neuropathies," Neurology vol. 56, p. 1371-1377 (2001).
Enbrel approval letter (1998) (4 pages).
Etanercept FDA appoval letter Nov. 2, 1998.
Fasanmade et al., "Population pharmacokinetic analysis of infliximab in patients with ulcerative colitis," Eur J Clin Pharmacol, vol. 65:1211-1228 (2009).
FDA Advisory Committee Reviews Safety of TNF Inhibitors (2001) (2 pages).
FDA Briefing Document, Mar. 4, 2003 Meeting of Arthritis Advisory Committee, "Update on the TNF-Blocking Agents" (47 pages).
Feagan B. et al., "A Comparison of Methotrexate with Placebo for the Maintenance of Remission in Crohn's Disease," N. Engl. J. Med., 342(22):1627-1632 (2000).
Federal Register, Department of Health and Human Services, vol. 68(37) 1 page 8771-8772 (2003).
Feldmann, M. et al., "Anti-TNFα Therapy of Rheumatoid Arthritis: What Have We Learned," Annu. Rev. Immunol., vol. 19:163-196 (2001).
Ferns et al., Inhibition of neointimal smooth muscle accumulation after angioplasty by and antibody to PDGF, Science vol. 253, p. 1129-1132 (1991).
Fietze et al. "Cytomegalovirus infection in transplant recipients,"Transplantation vol. 58, p. 675-680 (1994).
Figini, M. et al., "In Vitro Assembly of Repertoires of Antibody Chains on the Surface of Phage by Renaturation," J. Mol. Biol., vol. 239:68-78 (1994).
Fomsgaard, A. et al., "Auto-antibodies to Tumour Necrosis Factor α in Healthy Humans and Patients with Inflammatory Diseases and Gram-Negative Bacterial Infections," Scand. J. Immunol., 30:219-23 (1989).
Foote, J. et al., "Antibody Framework Residues Affecting the Conformation of the Hypervariable Loops," J. Mol. Biol., vol. 224:487-499 (1992).
Furst, D. et al., "Adalimumab, a Fully Human Anti-Tumor Necrosis Factor-α Monoclonal Antibody, and Concomitant Standard Antirheumatic Therapy for the Treatment of Rheumatoid Arthritis: Results of Star (Safety Trial of Adalimumab in Rheumatoid Arthritis)," The Journal of Rheumatology, vol. 30(12):2563-2571 (2003).
Furst, D. et al., "Safety and Efficacy of Adalimumab (D2E7), a Fully Human Anti-TNF-α Monoclonal Antibody, Given in Combination with Standard Antirheumatic Therapy: Safety Trial of Adalimumab in Rheumatoid Arthritis," Arthritis Rheum., vol. 46(9 Suppl.):5572 (2002).
Furst, D. et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," Arthritis Rheum., vol. 44(9 Suppl.):5215 (2001).
Furst, Daniel E., "The Risk of Infections with Biologic Therapies for Rheumatoid Arthritis," Rheumatoid Arthritis, pp. 327-346 (2010).
Fuss et al., "Treatment of ulcerative colitis with infliximab: are we there yet?" J. Pediatric Gastroenterology and Nutrition, 38:247-249 (2004).
Gardam et al., "Anti-tumour necrosis factor agents and tuberculosis risk: mechanisms of action and clinical management," Lancet Infect Dis. 3:148-155 (2003).
Geboes, Histopathology of Crohn's disease and ulcerative colitis, Inflammatory Bowel Disease, Edinburgh, London, Melbourne: Churchill Livingstone, 255-275 (2003).
Gomez-reino et al., "Treatment of Rheumatoid Arthritis With Tumor Necrosis Factor Inhibitors May Predispose to Significant Increase in Tuberculosis Risk," Arthritis & Rheumatism, 48(8):2122-2127 (2003).
Gordon et al., "Clinical response to adalimumab treatment in patients with moderate to severe psoriasis: double-blind, randomized controlled trial and open-label extension study," J. Am. Acad. Dermatol., 55(4) 598-606.
Gordon K.B. et al.: "Efficacy and safety of efalizumab in a large cohort of patients with moderate to severe plaque psoriasis: pooled results from randomized phase III trials", Supplemental to J. Amer. Academy of Dermatology, 50(3), Mar. 2004.
Gordon, K. et al., "Adalimumab efficacy and safety in patients with moderate to severe chronic plaque psoriasis: preliminary findings

(56) References Cited

OTHER PUBLICATIONS from a 12-week dose-ranging trial," poster presented Feb. 2004 at the American Academy of Dermatology Meeting (62nd Annual Meeting; Feb. 6-11, 2004).
Gornet et al., "Infliximab for refractory ulcerative colitis or indeterminate colitis: an open-label multicentre study," Aliment Pharmacol Ther, 18:175-181 (2003).
Goto, Daisuke et al., "Adalimumab," Medline AC NLM12510366 (2002).
Goto, Daisuke et al., "Adalimumab," Nippon Rinsho, 60(12):2384-2389 (2002).
Gottlieb, A. B., "Infliximab for Psoriasis," J. Am. Acad. Dermatol., 49(2):S112-S117 (2003).
Gottlieb, A. et al., "Infliximab Monotherapy Provides Rapid and Sustained Benefit for Plaque-Type Psoriasis," J. Am. Acad. Dermatol., 48(6):829-835 (2003).
Granneman, Richard G. et al., "Pharmacokinetic/Pharmacodynamic (PK/PD) Relationships of Adalimumab (HUMIRA™, Abbott) in Rheumatoid Arthritis (RA) Patients during Phase II/III Clinical Trials," Arthritis Rheum., vol. 48(Suppl. 9):S140 (2003).
Griffiths, A.D. et al. "Human Anti-Self Antibodies with High Specificity from Phage Display Libraries," The EMBO J., 12(2):725-34 (1993).
Guidance for Industry, Rheumatoid Arthritis: Developing Drug Products for Treatment, Draft Guidance, U.S. Department of Health and Human Services, Food and Drug Administration, May 2013 (11 pages in total).
Haley, H. et al., "Infliximab Therapy for Sarcoidosis (Lupus Pernio)," British J. Dermatol., 150(1):146-149 (2004).
Hamada et al., "Insuliln secretion to glucose as well as nonglucose stimuli ins impaired in spontaneously diabetic nagoya-shibata-yasuda mice," Metabolism. vol. 50, p. 1282-1285 (2001).
Hamilton, K. et al, "Tumour Necrosis Factor-α Blockade: A New Era for Effective Management of Rheumatoid Arthritis." Expert Opin. Pharm., 1(5):1041-1052 (2000).
Hanauer et al., "Incidence and Importance of Antibody Responses to Infliximab After Maintenance or Episodic Treatement in Crohn's Disease," Clinical Gastroenterology and Hepatology, vol. 2(7):542-553 (2004).
Hanauer S. et al., "A Randomized, Double-Blind, Placebo-Controlled Trial of the Human Anti-TNF-alpha Monoclonal Antibody Adalimumab for the Induction of Remission in Patients with Moderate to Severely Active Crohn's Disease," Gastroenterology, 127(1):331-332 (2004).
Hanauer S. et al., "Human Anti-Tumor Necrosis Factor Monoclonal Antibody (Adalimumab) in Crohn's Disease: the Classic-I Trial," Gastroenterology, 130(2):323-333 (2006).
Hanauer, S. et al., "Maintenance infliximab for Crohn's Disease: The Accent I Randomised Trial," Lancet, 359(9317):1541-1549 (2002).
Hanauer, Stephen B., Efficacy and Safety of Tumor Necrosis Factor Antagonists in Crohn's Disease: Overview of Randomized Clinical Studies, Reviews in Gastroenterological Disorders, 4(3):S18-S24 (2004).
Harriman G. et al., "Summary of Clinical Trials in Rheumatoid Arthritis Using Infliximab, an Anti-TNFα Treatment," Ann. Rheum. Dis. vol. 58(1):161-164 (1999).
Haseyama et al., "Complications of IgA nephropathy in a non-insulin dependent diabetes model the Akita mouse," Tohoku J Exp Med. vol. 198, p. 233-244 (2003).
Hattori et al, "High glucose induced nuclear factor κB activation in vascular smooth muscle cells,". Cardiovasc Res. vol. 46, p. 188-197 (2000).
Hawkins, Robert E. et al., "Selection of Phage Antibodies by Binding Affinity Mimicking Affinity Maturation," J. Mol. Biol., vol. 226:889-896 (1992).
Hessel et al., "Bronchoconstriction and airway hyperresponsiveness after ovalbumin inhalation in sensititzed mice," Eur Jpharmacol. vol. 293, p. 401-412 (1995).
HighBeam Research, "Adalimumab is safe, well tolerated, and improves RA signs, symptoms," Drug Week, Jan. 17, 2003 (2 pgs).
Hochberg et al., "Comparison of the efficacy of the tumour necrosis factor alpha blocking agents adalimumab, etanercept, and infliximab when added to methotrexate in patients with active rheumatoid arthritis," Annals of the Rheumatic Diseases, British Medical Association, London, GB, 62(2-Suppl.):ii13-ii16 (2003).
Holler, E. et al., "Modulation of Acute Graft-Versus-Host Disease After Allogeneic Bone Marrow Transplantation by Tumor Necrosis Factor α (TNFα) Release in the Course of Pretransplant Conditioning: Role of Conditioning Regimens and Prophylactic Application of a Monoclonal Antibody Neutralizing Human TNFα (MAK 195F)," Blood, vol. 86(3):890-899 (1995).
Holliger et al., "Engineered Antibody Fragments and the Rise of Single Domains," Nat. Biotechnol., 23(9):1126-1136 (2005).
Hoogenboom, Hennie R. et al., "Converting rodent into human antibodies by guided selection," Antibody Engineering, Oxford University Press, Chpt. 8, pp. 169-185 (1996).
Huse, W. et al., "Generation of a Large Combinatorial Library of the Immunoglobulin Repertoire in Phage Lambda" Science, 246:1275-81 (1989).
Huygen et al., "Evidence for local inflammation in complex pain syndrome type 1," Mediators Inflamm. vol. 11, p. 47-51 (2002).
Infliximab FDA approval letter Aug. 24, 1998.
International Preliminary Report on Patentability for Application No. PCT/US05/12007, dated Oct. 16, 2006.
Ishii et al., "Tumor necrosis factor alpha gene G-308 polymorphism, insulin resistance, and fasting plasma glucose in young, older and diabetic Japanese men," Metabolism vol. 49, p. 1616-1618 (2000).
Iznaga-escobar et al., "Factors Affecting Pharmacokinetics of Monoclonal Antibodies: A Review Article," Methods Find Exp Clin Pharmacol, 26(2):123-127 (2004).
Janeway et al., "The Immune System in health and Disease," Immunobiology, 5th Ed., Garland Science, pp. 94-105 (2001).
Janeway, Charles A., Jr., "The Protein Products of MHC class I and class II genes are highly polymorphic," Immunobiology, Third Edition, pp. 4:24-4:30 (1997).
Javed et al., "Tumor necrosis factor-α antibody eluting stents reduce vascular smooth muscle cell proliferation in saphenous vein organ culture," Exp and Mol Pathol vol. 73, p. 104-111 (2002).
Jenkins et al., "Guidelines for the initial biopsy diagnosis of suspected chronic idiopathic inflammatory bowel disease. The British Society of Gastroenterology Initiative," J Clin Pathol., 50:93-105 (1997).
Jespers, Laurent S. et al., "Guiding the Selection of Human Antibodies from Phage Display Repertoires to a Single Epitope of an Antigen," Bio/Technology, vol. 12:899-903 (1994).
Jongen-Lavrencic et al., "Elevated levels of inflammatory cytokines in bone marrow of patients with rheumatoid arthritis and anemia of chronic disease," J. Rheumalol vol. 24, p. 1504-1509 (1997).
Kaijtzel et al., "Polymorphism within the tumor necrosis factor α (TNF) promoter region in patients with ankylosing spondylitis," Hum Immunol. vol. 60, p. 140-144 (1999).
Kanakoudi-Tsakalidou, F. et al., "Influenza vaccination in children with chronic rheumatic diseases and long-term immunosuppressive therapy," Clinical and Experimental Rheumatology, vol. 19:589-594 (2001).
Kavanaugh, A. et al., "Immune Response is Not Affected by Adalimumab Therapy," Ann. Rheum. Dis., vol. 62(Suppl. 1):169 (2003).
Kavanaugh, A. F. et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," Ann. Rheum. Dis., vol. 61 (Suppl. 1):S168 (2002).
Kavanaugh, Arthur F. et al., "Treatment with Adalimumab (D2E7) does not Affect Normal Immune Responsiveness," Arthritis Rheum., vol. 46(9 Suppl.):S132 (2002).
Kaymkcalan, Z. et al., "Comparison of Adalimumab (D2E7), Infliximab, and Etanercept in the Prevention of Polyarthritis in the Transgene Murine Model of Rheumatoid Arthritis," Arthritis, Rheum., vol. 46(9 Suppl.):S304 (2002).

(56) References Cited

OTHER PUBLICATIONS

Keast et al., "A survey of pathological changes associated with long-term high tar tobacco smoke exposure in a murine model," J. Pathol. vol. 135, p. 249-257 (1981).
Kempeni, J., "Update on D2E7: A Fully Human Anti-Tumour Necrosis Factor α Monoclonal Antibody," Ann. Rheum. Dis., vol. 59(Suppl.1):144-145 (2000).
Kempeni, Joachim, "Preliminary Results of early clinical trials with the fully human anti-TNFα monoclonal antibody D2E7," Ann. Rheum. Dis., vol. 58(Suppl. 1):170-172 (1999).
Keystone, "Appropriate and Effective Rheumatoid Arthritis Control: Role of TNF Antagonists," Drugs of Today, (39)Suppl. B:9-15, (2003).
Keystone, E. C. et al., "Subgroup Analysis of Radiographic Progression in RA Patients with Moderate Disease Treated with Adalimumab (HUMIRA®)," Ann. Rheum. Dis., vol. 62(Suppl. 1):169 (2003).
Keystone, E. et al., "Adalimumab Inhibits the Progression of Structural Joint Damage in Patients with Active RA," Ann. Rheum. Dis., vol. 62(Suppl. 1):64-5 (2003).
Keystone, E. et al., "Efficacy and safety of Adalimumab (D2E7), the fully human anti-TNF monoclonal antibody, in MTX partial responders: Results of the 24-week Armada trial," JCR: Journal of Clinical Rheumatology, vol. 8(3):S69 (2002).
Keystone, E. et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)," Presented at the Annual Meeting of the European League Against Rheumatoid Arthritis (EULAR), Prague, Czech Republic, Jun. 2001.
Keystone, Edward et al., "Sustained Radiographic Inhibition with Adalimumab (HUMIRA™) over 2 years in Patients with Long Standing Rheumatoid Arthritis (RA)," Arthritis Rheum., vol. 48(Suppl. 9):S315 (2003).
Keystone, Edward et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatism, vol. 44(9):S213 (2001).
Kim; Chung, "An experimental model for peripheral neuropathy produced by segmental spinal nerve ligation in the rat," PAIN vol. 50, pp. 355-363 (1992).
Kimball A. B. et al., "Efficacy and Safety of Adalimumab in Treatment of Moderate to Severe Hidradenitis Suppurativa: Results for the Placebo-controlled Portion of a Phase II, Randomized, Double-Blind Study," 69th Annual Meeting of the Am. Acad. of Derma. in New Orleans, Feb. 4, 2011.
Kinjoh et al., "Genetic selection for crescent formation yields mouse strain with rapidly progressive glomerulonephritis and small vessel vasculitis," Proc. Natl. Acad Sci., USA vol. 90, p. 3413-3417 (1993).
Kohn et al., "Infliximab in the treatment of severe ulcerative colitis: a follow-up study," European Review for Medical and Pharmacological Sciences, 8:235-237 (2004).
Kolb, "Mouse models of insulin dependent diabetes: low dose streptozocin induced diabetes and nonobese diabetic (NOD) mice," Diabetes/Metabolism Reviews vol. 3, p. 751-778 (1987).
Kremer, Joel M., "Rational Use of New and Existing Disease-Modifying Agents in Rheumatoid Arthritis," Ann. Intern. Med., vol. 134:695-706 (2001).
Kroesen et al., "Serious bacterial infections in patients with rheumatoid arthritis under antiTNF-α therapy," Rheumatology 42:617-621 (2003).
Kruger-Thiemer E., "Formal theory of drug dosage regimens. I.," Journal of Theoretical Biology, vol. 13:212-235 (1966) (abstract submitted—1 page).
Kruger-Thiemer, E., "Continuous Intravenous Infusion and Multicompartment Accumulation," European Journal of Pharmacology, vol. 4:317-324 (1968).

Kuo et al., Neonatal Fc Receptor: From Immunity to Therapeutics, J. Clin. Immunol, 30(6):777-789 (2010).
Lerner, R. A. et al., "Antibodies Without Immunization," Science, 258:1313-14 (1992).
Leusch, H-G. et al. "Failure to demonstrate TNFα-specific autoantibodies in human sera by ELISA and Western blot" J. Immunol. Methods, 139:145-47 (1991).
Lewis et al., "Use of alanine scanning mutagenesis to improve the affinity of an anti gp 120 (HIV) antibody," J. Cell. Biochem., 18D:215 (1994).
Libby, "Molecular bases of the acute coronary syndromes," Circulation vol. 91, p. 2844-2850 (1995).
Liberopoulos et al., "Exacerbation of Tuberculosis Enteritis After Treatment with Infliximab," The American Journal of Medicine, vol. 113, p. 615 (2002).
Lilja, I. et al., "Tumor Necrosis Factor-Alpha in Lleal Mast Cells in Patients with Crohn's disease," Digestion, vol. 51(1):68-76 (2000).
Lindner et al., "Mouse model of arterial injury," Circ Res. vol. 73, p. 792-796 (1993).
Lipsky et al., "Infliximab and Methotrexate in the Treatment of Rheumatoid Arthritis," The New England Journal of Medicine 343:1594-1602 (2000).
Lobo et al., "Antibody Pharmacokinetics and Pharmacodynamics," Journal of Pharmaceutical Sciences, 93(11):2645-2668 (2004).
Lobo, E.D., Hansen, R.J. and Balthasar, J.P. (2004), Antibody pharmacokinetics and pharmacodynamics. J. Pharm. Sci., retrieved from Internet on Jan. 27, 2014 http://onlinelibrary.wiley.com/doi/10/1002/jps.20178/abstract;jsessionid=B34750619DF22 . . . (3 pages).
Loftus et al., "Adalimumab real-world dosage pattern and predictors of weekly dosing: Patients with Crohn's disease in the United States," Journal of Crohn's and Colitis, 5:550-554 (2011).
Lorenz, "Technology Evaluation: Adalimumab, Abbott Laboratories," Current Opinion in Molecular Therapeutics, London, GB, 4(2):185-190 (2002).
Low, Nigel M. et al., "Mimicking Somatic Hypermutation: Affinity Maturation of Antibodies Displayed on Bacteriophage Using a Bacterial Mutator Strain," J. Mol. Biol., vol. 260:359-368 (1996).
Low, Nigel M., Thesis Extract, Cambridge University (1996).
Lugering et al., "Infliximab Induces Apoptosis in Monocytes From Patients With Chronic Active Crohn's Disease by Using a Caspase-Dependent Pathway," Gastroenterology, 121(5):1145-1157 (2001).
Macdonald et al., "Tumour necrosis factor-alpha an interferon—gamma production measured at the single cell level in normal and inflamed human intestine," Clin. Exp. Immunol. vol. 81, p. 301-305 (1990).
Machold, Klaus P. et al., "Adalimumab-A New TNF-α Antibody for Treatment of Inflammatory Joint Disease," Expert Opin. Biol. Ther., vol. 3(2):351-360 (2003).
Maini et al., "How does infliximab work in rheumatoid arthritis?" Arthritis Research, 4(2):S22-S28 (2002).
Maini R. N. et al., "Therapeutic Efficacy of Multiple Intravenous Infusions of Anti-Tumor Necrosis Factor a Monoclonal Antibody Combined with Low-Dose Weekly Methotrexate in Rheumatoid Arthritis," Arthritis & Rheumatism, 41(9):1552-1563 (1998).
Makino et al., "Breeding of a non-obese diabetic strain of mice," Exp.Anim. vol. 29, p. 1-13 (1980).
Mamula et al., "Infliximab in pediatric ulcerative colitis: two year follow-up," J. Pediatric Gastroenterology and Nutrition, 38:289-301 (2004).
Manadan et al., "Mycobacteria tuberculosis peritonitis associated with etanercept therapy," Letters to the Editor, p. 526.
Marks, J. et al. "By-passing immunization: Human antibodies from V-gene libraries displayed on phage" J. Mol. Biol., 222:581-97 (1991).
Massarotti, E. M. et al., "Treatment Patterns in Early-Onset Rheumatoid Arthritis (RA): Results from the Sonora Study," Ann. Rheum. Dis., vol. 61 (Suppl. 1):593 (2002).
Mccall et al., "Serum tumour necrosis factor alpha and insulin resistance in gastrointestinal cancer," Br. J. Surg. vol. 79, p. 1361-1363 (1992).

(56) References Cited

OTHER PUBLICATIONS

Medall et al., "Relation of serum cytokine concentrations to cardiovascular risk factors and coronary heart disease," Heart vol. 78, p. 273-277 (1997).
Medynski, Dan, "Phage Display: All Dressed Up and Ready to Role," Bio/Technology, vol. 12:1134-1136 (1994).
Mohan et al., "Effects of Tumor Necrosis Factor Alpha on Host Immune Response in Chronic Persistent Tuberculosis: Possible Role for Limiting Pathology," Infection and Immunity, 69(3):1847-1855 (2001).
Moller A. et al. "Monoclonal Antibodies to Human Tumor Necrosis Factor α: in Vitro and Vivo Application" Cytokine, 2(3):162-69 (1990).
Molnar et al., "Frequency and Predictors of loss of Response to Infliximab or Adalimumab in Crohn's Disease after One-Year Treatment Period—A Single Center Experience," J. Gastrointestin Liver Dis. 21(3):265-269 (2012).
Mould et al, "Basic Concepts in Population Modeling, Simulation, and Model-Based Drug Development," CPT Pharmacometrics Syst Pharmacol Sep. 25, 2012;1:e6.
Mould et al, "Basic concepts in population modeling, simulation, and model-based drug development-part 2: introduction to pharmacokinetic modeling methods," CPT Pharmacometrics Syst Pharmacol Apr. 17, 2013;2:e38.
Mould et al, "Population pharmacokinetic-pharmacodynamic modeling of biological agents: when modeling meets reality," J Clin Pharmacol Sep. 2010;50(9 Suppl):91S-100S.
Mould et al., "Pharmacokinetics and Pharmacodynamics of Monoclonal Antibodies, Concepts and Lessons for Drug Development," Biodrugs, 24(1):23-39 (2010).
Mould et al., "The pharmacokinetics and pharmacodynamics of monoclonal antibodies—mechanistic modeling applied to drug development," Current Opinion in Drug Discovery & Development, 10(1):84-96 (2007).
Myers, "The pathogenesis of neuropathic pain," Regional Anesthesia vol. 20, p. 173-185 (1995).
Nahar et al., "Infliximab Treatment of Rheumatoid Arthritis and Crohn's Disease," The Annals of Pharmacotherapy 37:1256-1265.
Nakamura et al. "Induction of left ventricular remodeling and dysfunction in the recipient heart following donor heart myocardial infarction; new insights into the pathological role of tumor necrosis factor-α from a novel heterotopic transplant coronary ligation model," J Cardiol. vol. 41, p. 35-46 (2003).
Nash et al., "Expression of tumour necrosis factor-α in cryptogenic fibrosing alveolitis," Histopathology vol. 22, p. 343-347 (1993).
Navarro et al., "Inflammatory parameters are independently associated with urinary albumin in type 2 diabetes mellitus," Am JKidney Dis. vol. 42, p. 53-61 (2003).
Nestorov "Clinical Pharmacokinetics of TNF Antagonists: How Do They Differ?," Arthritis and Rheumatism 12-18 (2005).
Nestorov "Clinical Pharmacokinetics of Tumor Necrosis Factor Antagonists," The Journal of Rheumatology 13-18 (2003).
Nilsson, Bjorn, "Antibody engineering," Current Opinion in Structural Biology, vol. 5:450-456 (1995).
Noertersheuser et al., "Factors Affecting Adalimumab Pharmacokinetics in Adult Patients with Moderate to Severe Crohn's Disease," Feb. 6, 2013 (1 page).
Nose et al., "Arteritis in a novel congenic strain of mice derived from MRL/lpr lupus mice," Am. J. Path. vol. 149, p. 1763-1769 (1996).
Office Action cited during prosecution of U.S. Appl. No. 10/163,657, dated Sep. 21, 2006.
Office Action cited during prosecution of U.S. Appl. No. 10/163,657, dated Jun. 18, 2007.
Office Action cited during prosecution of U.S. Appl. No. 10/622,932, dated Sep. 6, 2006.
Office Action cited during prosecution of U.S. Appl. No. 10/622,932, dated May 23, 2007.
Office Action cited during prosecution of U.S. Appl. No. 10/622,932, dated Jul. 3, 2008.
Office Action cited during prosecution of U.S. Appl. No. 10/622,932, dated Jan. 13, 2009.
Ordas et al., "Anti-TNF Monoclonal Antibodies in Inflammatory Bowel Disease: Pharmacokinetics-Based Dosing Paradigms," Clinical Pharmacology & Therapeutics, 91(4):635-646 (2012).
Osbourn, Jane et al., "From Rodent Reagents to Human Therapeutics Using Antibody Guided Selection," Methods, 36:61-68 (2005).
Palladino, M. A. et al., "Anti-TNF-α Therapies: the Next Generation." Nat. Rev. Drug Discov., 2(9):736-746 (2003).
Papadakis et al., "Safety and Efficacy of Adalimumab (D2E7) in Crohn's Disease Patients with an Attenuated Response to Infliximab," Am. J. Gastroent., 100(1):75-79 (2005).
Parada et al., "Tumor necrosis factor receptor type-1 in sensory neurons contributes to induction of chronic enhancement of inflammatory hyperalgesia in rat," Eur J Neurosci vol. 17, p. 1847-1852 (2003).
Partsch et al., T cell derived cytokines in psoriatic arthritis synovial fluids, Ann Rheum Dis. vol. 57, p. 691-693 (1998).
Patel, T. et al., "Adalimumab: Efficacy and Safety in Psoriasis and Rheumatoid Arthritis," Dermatologic Therapy, vol. 17(5):427-431 (2004).
Paulson S. et al., "Pharmacokinetics of Adalimumab from Classic, a Randomized Phase 3 Trial for the Induction of Clinical Remission in Patients with Crohn's Disease," Gastroenterology, 128(4) (Suppl. 2):A585 (2005) [Abstract W1057].
Pendley et al., "Immunogenicity of Therapeutic Monoclonal Antibodies," Current Opinion in Molecular Therapeutics 5(2):172-179 (2003).
Peyrin-Biroulet L. et al., "Efficacy and Safety of Tumor Necrosis Factor Antagonists in Crohn's Disease: Meta-Analysis of Placebo-Controlled Trials," Clin. Gastroent. Hepatol., American Gastroenterological Association, US, 6(6):644-653 (2008).
Pfeiffer et al. "Circulating tumor necrosis factor α is elevated in male but not in female patients with type II diabetes mellitus," Horm Metab Res. vol. 29, p. 111-114 (1997).
Pihlajamaki j et al. "The effect of the -308A allele of the TNF-α gene on insulin action is dependent on obesity," Obes Res. vol. 11, p. 912-917 (2003).
Pincus, Theodore et al, "Combination Therapy with Multiple Disease-Modifying Antirheumatic Drugs in Rheumatoid Arthritis: A Preventive Strategy," Ann. Intern. Med., vol. 131:768-774 (1999).
Piquet et al., "Tumor necrosis factor/cachectin plays a key role in bleomycin-induced pneumopathy and fibrosis," J Exp Med. vol. 170, p. 655-663 (1989).
Plosker et al., "Adalimumab," Biodrugs 21(2):125-132 (2007).
Pradhan et al., "Relationship between Adalimumab Concentration and Efficacy for the Induction of Clinical Remission in Paediatric Patients with Moderate to Severe Crohn's Disease," Feb. 6, 2013 (1 page).
Prescribing information for REMICADE™ (Infliximab) © Centocor, Inc. Dec. 1, 2000, pp. 14-31.
Present et al., "Infliximab for the Treatment of Fistulas in Patients with Crohn's Disease," N. Engl. J. Med., 340:1398-405 (1999).
Probert et al., "Infliximab in moderately severe glucocorticoid resistant ulcerative colitis: a randomised controlled trial," Gut., 52:998-1002 (2003).
Proudfoot, S., (updated by John Collett), "Dosage Regimens: Their Influence on the Concentration-Time Profile of a Drug in the Body," in Michael E. Aulton, Pharmaceutics: The Science of Dosage Form Design, 2nd Ed., Chapter 19 pp. 275-288 (2001).
Qiang et al. "Inhibitory effect of troglitazone on diabetic neuropathy in streptozotocin-induced diabetic rats," Diabetologia vol. 41, p. 1321-1326 (1998).
Queen, Cary et al., "A Humanized Antibody that Binds to the Interleukin 2 Receptor," Proc. Natl. Acad. Sci. USA, vol. 86:10029-10033 (1989).
R&D Focus Drug News, Jan. 13, 2003, IMS World Publications Ltd. 1 page.
Rankin, E.C. et al., "The therapeutic effects of an engineered human anti-tumor necrosis factor alpha antibody (CDP571) in rheumatoid arthritis," Br. J. Rheumatol. vol. 34, 1995, pp. 334-342 (1995).
Rau, R. et al., "2.5-Year Treatment Results with Adalimumab (D2E7), the First Fully Human Anti-TNF Monoclonal Antibody, in

(56) References Cited

OTHER PUBLICATIONS

Combination with Methotrexate in Active Rheumatoid Arthritis," Ann. Rheum. Dis., vol. 61(Suppl. 1):S55 (2002).
Rau, R. et al., "Erfahrungen mit D2E7," Akt. Rheumatol., vol. 25:83-88 (2000).
Rau, R. et al., "Kombinationstheraipe mit dem humanen Anti-α-Antikorper D2E7 and Methotrexat bei aktiver chronischer Polyarthritis," Z. Rheumatol., vol. 58(Suppl. 1 ):1/35, F20 (1999).
Rau, R. et al., "Long-term Treatment with the Fully Human Anti-TNF-Antibody D2E7 Slows Radio-graphic Disease Progression in Rheumatoid Arthritis," Arthritis and Rheumatism, vol. 42(9):S400 (1999).
Rau, R. et al., "Treatment with Adalimumab (D2E7), the Fully Human Anti-TNF Monoclonal Antibody, Slows Radiographic Disease Progression in Rheumatoid Arthritis: Results of a 12-Month Study," J. Clin. Rheum., vol. 8(Suppl.):S78 (2002).
Rau, R. et al., "Wirkung under Vertraglichkeit wiederholter intravenoser Gaben der humanen anti-TNF Antikorpers D2E7 bei Patienten mit chronischer Polyarthritis," Z. Rheumatol., vol. 58(Suppl. 1):1/41, P12 (1999).
Rau, R., "Adalimumab (a fully human anti-tumour necrosis factor a monoclonal antibody) in the treatment of active rheumatoid arthritis: the initial results of five trials," Ann. Rheum. Dis., vol. 61(Suppl.II):ii70-ii73 (2002).
Rau, R., "Erfahrungen mit D2E7," Z. Rheumatol., vol. 58(Suppl. 1):1/21, S51 (1999).
Rau, R.et al., "Adalimumab Inhibits Radiographic Disease Progression in Long-Standing, Rapidly Progressive Rheumatoid Arthritis," Ann. Rheum. Dis., vol. 62(Suppl. 1):191 (2003).
Rau, Rolf et al., "Long-term efficacy and tolerability of multiple I.V. doses of the fully human Anti-TNF-Antibody D2E7 in patients with Rheumatoid Arthritis," Arthritis & Rheumatism, vol. 41(Suppl. ):555, No. 137 (1998).
Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care. Med., vol. 24(5):733-742 (1996).
Remicade "Advisory Committee Briefing Document for Safety with Remicade," 1-24 (2001).
Remicade approval letter (1998) (4 pages).
Remicade for IV Injection, Centocor, Inc., pp. 1-23, Jun. 2002.
Revicki, D. et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," Arthritis Rheum., vol. 46(9 Suppl.):S537 (2002).
Riechmann, Lutz et al., "Phage Display and Selection of a Site-Directed Randomized Single-Chain Antibody Fv Fragment for Its Affinity Improvement," Biochemistry, vol. 32:8848-8855 (1993).
Ritchlin et al., Patterns of cytokine production in psoriatic synovium, J Rheumatol. vol. 25, p. 1544-1552 (1998).
Rosh et al., "Retrospective Evaluation of the Safety and Effect of Adalimumab Therapy (RESEAT) In pediatric Crohn's disease," Am. J. Gastroenterol., 104(12):3042-3049 (2009).
Rudikoff, Stuart et al., "Single Amino Acid Substitution Altering Antigen-Binding Specificity," Proc. Natl. Acad. Sci. USA, vol. 79:1979-1983 (1982).
Russell, D; Thompson, R.C. "Targets for sepsis therapies:tumor necrosis factor versus interleukin-1,"Curr. Opin. Biotech. vol. 4, pp. 714-721 (1993).
Rutgeerts "Challenges in Crohn's Disease," Rev. Gastroenterol Disord. 4(3):S1-S2) 2004.
Rutgeerts et al., "Comparison of Scheduled and Episodic Treatment Strategies of Infliximab in Crohn's Disease," Gastroenterology, vol. 126(2):402-413 (2004).
Rutgeerts et al., "Efficacy and Safety of Retreatment With Anti-Tumor Necrosis Factor Antibody (Infliximab) to Maintain Remission in Crohn's Disease," Gastroenterology 117:761-769 (1999).
Rutgeerts, "An Historical Overview of the Treatment of Crohn's Disease: Why Do We Need Biological Therapies?" Reviews in Gastroenterological Disorders, 4(3):53-59 (2004).
Salfeld, J. et al., "Generation of Fully Human Anti-TNF Antibody D2E7," Arthritis Rheum., vol. 41(9 Suppl.):S57 (1998).
Sandborn et al., "Adalimumab 160-/180-mg Induction Regimen is Associated with Better Outcomes Compared with the 80-/40-mg Regimen During Maintenance Therapy in Patients with Crohn's Disease," Sa1245 p. 1.
Sandborn et al., "Adalimumab for maintenance treatment of Crohn's disease: results of the Classic I Trial," Gut, 56:1232-1239 (2007).
Sandborn et al., "An Engineered Human Antibody to TNF (CDP571) for Active Crohn's Disease: A Randomized Double-blind Placebo-Controlled Trial," Gastroenterology, 120(6):1330-1338 (2001).
Sandborn et al., "Dosage Adjustment During Long-term Adalimumab Treatment for Crohn's Disease: Clinical Efficacy and Pharmacoeconomics," Inflamm Bowel Dis 17:141-151 (2011).
Sandborn et al., "Etanercept for Active Crohn's Disease: a Randomized, Double-Blind, Placebo-Controlled Trial," Gastroenterology, 121(5): 1088-1094 (2001).
Sandborn et al., "How Future Tumor Necrosis Factor Antagonists and Other Compounds Will Meet the RemainingChallenges in Crohn's Disease," Rev Gastroenterol Disord. 4(suppl 3):S25-S33 (2004).
Sandborn et al., "Natalizumab Induction and Maintenance Therapy for Chrohn's Disease," N Engl J Med, vol. 353:1912-1925 (2005).
Sandborn et al., "Optimizing anti-tumor necrosish factor strategies in inflammatory bowel disease," Curr Gastroenterol Rep., 5:501-505 (2003).
Sandborn et al., Inflammatory Bowel Disease, "CDP571, a humanised monoclonal antibody to tumour necrosis factor α, for moderate to severe Crohn's disease: a randomised, double blind, placebo controlled trial," GUT, 53:1485-1493 (2004).
Sandborn, W. "Strategies for Targeting Tumor Necrosis Factor in IBD," Best Practice and Research Clin. Gastroenterology, vol. 17(1):105-117 (2003).
Sandborn, W. et al, "An open-label study of the human anti-TNF monoclonal antibody adalimumab in subjects with prior loss of response or intolerance to infliximab for Crohn's disease." Am. J. Gastroenterol, vol. 99(10):1984-1989 (2004).
Sandborn, W. et al., "Infliximab in the Treatment of Crohn's Disease: A User's Guide for Clinicians," The American Journal of Gastroenterology, vol. 97(12):2962-2972 (2002).
Sands "Why Do Anti-Tumor Necrosis Factor Antibodies Work in Crohn's Disease?," Rev Gastroenterol Disord. 4(suppl 3):S10-S17 (2004).
Santora, L. C. et al., "Characterization of Noncovalent Complexes of Recombinant Human Monoclonal Antibody and Antigen Using Carbon Exchange, Size Exclusion Chromatography, and BIAcore," Analytical Biochemistry, vol. 299(2):119-129 (2001).
Santora, L. C. et al., "Characterization of Recombinant Human Monoclonal Tissue Necrosis Factor-α Antibody Using Caution-Exchange HPLC and Capillary Isoelectric Focusing," Analytical Biochemistry, vol. 275:98-108 (1999).
Scallon et al., "Binding and Functional Comparisons of Two Types of Tumor Necrosis Factor Antagonists," The Journal of Pharmacology and Experimenttal Therapeutics 301:418-426 (2002).
Schafers et al., "Increased sensitivity of injured and adjacent uninjured rat primary sensory neurons to expgeous tumor necrosis factor-α after spinal nerve ligation" J Neurosci vol. 23, p. 3028-3038 (2003).
Schattenkirchner, M. et al, "Efficacy and Tolerability of Weekly Subcutaneous Injections of the Fully Human Anti-TNF-Antibody D2E7 in Patients with Rheumatoid Arthritis—Results of a Phase I Study," Arthritis and Rheumatism, vol. 41(9):S57 (1998).
Schattenkirchner, M. et al., "Long-term Use of the Fully Human Anti-TNF Antibody Adalimumab (D2E7) in Dmard-refractory Rheumatoid Arthritis," Presented at: The Annual Meeting of the European League Against Rheumatism (EULAR), Prague, Czech Republic, Jun. 2001.

(56) References Cited

OTHER PUBLICATIONS

Schattenkirchner, M. et al., "Long-term Use of the Fully Human Anti-TNF Antibody D2E7 in Combination with Methotrexate in Active Rheumatoid Arthritis," Presented at: The Annual Meeting of the European League Against Rheumatism, p. S228 (2000).
Schattenkirchner, M. et al., "Phase-1-Studie zur Wirksamkeit and Vertraglichkeit Wochentlicher subcutaner Injekttionen des humanen Anti-TNF-Antikorpers D2E7 bei cP," Z. Rheumatol., vol. 58(Suppl. 1):1/42, p. 14 (1999).
Schellekens "Factors Influencing the Immunogenicity of Therapeutic Proteins," Nephrology Dialysis Transplantation, Nephrol Dial Transplant 20(6):vi3-vi9 (2005).
Schiff, M. et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," Ann. Rheum .Dis., vol. 61 (Suppl. 1):S169 (2002).
Schiff, M. et al., "Rates of Infection in Adalimumab Rheumatoid Arthritis Clinical Trials," Ann. Rheum. Dis., vol. 62(Suppl. 1):184 (2003).
Schiff, Michael H. et al., "Sustained Efficacy of Adalimumab (HUMIRATM) Plus Methotrexate in Rheumatoid Arthritis (RA) Patients," Arthritis Rheum., vol. 48(Suppl. 9):S314 (2003).
Scientific Discussion, Humira/Trudexa, Procedure No. EMEA/H/C/481-482/II/33, Apr. 26, 2007 (20 pages) Variation.
Scribano "Review Article: Medical Treatment of Moderate to Severe Crohn's Disease," Aliment Pharmacol Ther 17 (Suppl. 2): 23-30 (2003).
Shargel et al., "Applied Biopharmaceutics and Pharmacokinetics," 4th Ed., 1999, Appleton and Lange, 436-37.
Shargel et al., "Applied Biopharmaceutics and Pharmacokinetics," 5th Ed., McGraw-Hill, 2007, (1040 pages).
Sharma et al., "Relationship between Adalimumab Concentration and Efficacy for the Maintenance of Clinical Remission in Paediatric Patients with Moderate to Severe Crohn's Disease," Feb. 6, 2013 (1 page).
Shvidel, "Cytokine release by activate T-cells in large granular lymphocytic leukemia associate with autoimmune disorders" Hematol J. vol. 3, p. 32-37 (2002).
Sibilia, Jean, "Combinaison de traitements de fond dans la polyarthrite rhumatorde," Ann. Med. Interne., 153(1):41-52 (2002).
Smeets et al., "Tumor Necrosis Factor Blockade Reduces the Synovial Cell Infiltrate Early After Initiation of Treatment, but Apparently Not by Induction of Apoptosis in Synovial Tissue," Arthritis & Rheumatism 48(8):2155-2162 (2003).
Sommer, "Tierexperimentelle untersuchungen bei neuropathischem shmerz," Schmerz vol. 13, p. 315-323 (1999).
Sorkin et al., "Tumor necrosis factor-α induces ectopic activity in nociceptive primary afferent fibres," Neuroscience vol. 81, p. 255-262 (1997).
Spiegelman; Hotamisligil, "through thick and thin: wasting, obesity, and TNFα," Cell vol. 73, p. 625-627 (1993).
Statement on a Nonproprietary Name Adopted by the USAN Council, Adalimumab, published from 2001-2004 on the USAN website http://www.amaassn.org/ama1/pub/upload/mm/365/adalimumab.doc, 1 page.
Strand et al., "Biologic therapies in rheumatology: lessons learned, future directions," Nature Publishing Group 6:75-92 (2007).
Strand, New Developments in Rheumatic Diseases, 2:(1), pp. 1-8 Summer 2004.
Strand, V. et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," Ann. Rheum. Dis., vol. 61(Suppl. 1):S175 (2002).
Studnicka-Benke et al., Tumour necrosis factor alpha and its soluble receptors parallel clinical disease and autoimmune activity in systemic lupus erythematosus, Br J Rheumatol. vol. 35, p. 1067-1074 (1996).
Su et al., "Influence of Immunogenicity on the Long-term Efficacy of Infliximab in Crohn's Disease," Gastroenterology, vol. 125(5):1544-1546 (2003).
Sugano et al., "In vivo gene transfer of soluble TNF-α receptor 1 alleviates myocardial infarction," FASEB J vol. 16, p. 1421 (2002).
Sun et al., "Bowel necrosis induced by tumor necrosis factor in rats is mediated by platelet activating factor," J Clin. Invest. vol. 81, p. 1328-1331 (1988).
Suthanthiran; Strom, "Renal transplantation," New Engl. J. Med. vol. 331, p. 365-376 (1994).
Targan et al., "A Short-Term Study of Chimeric Monoclonal Antibody cA2 to Tumor Necrosis Factor a for Crohn's Disease," The New England Journal of Medicine 337(15):1029-1035 (1997).
Targan et al., "Natalizumab for the Treatment of Active Crohn's Disease: Results of the Encore Trial," Gastroenterology, vol. 132(5):1672-1683 (2007).
Taurog et al.: 'The Spondylarthritides.', 1998, Oxford University Press.
Taylor et al., "Tuberculosis following therapy with infliximab may be refractory to antibiotic therapy," Rheumatology 42:901-902 (2003).
The Merck Manual, "Inflammatory Bowel Diseases," Mark H. Beers, Ed., Merck Research Laboratories, 302-313 (1999).
Third party observations dated Jun. 11, 2013 in European Application No. 05777317.8 (Publication No. EP1737491) (12 pages).
Third party observations dated Jul. 12, 2013 in European Application No. 05777317.8 (Publication No. EP1737491) (2 pages).
Third party observations dated Aug. 27, 2012 in European Application No. 05777317.8 (Publication No. EP1737491) (17 pages).
Third party observations dated Oct. 21, 2013 in European Application No. 05777317.8 (Publication No. EP1737491) (4 pages).
Third party observations dated Nov. 12, 2013 in European Application No. 05777317.8 (Publication No. EP1737491) (4 pages).
Third party observations dated Dec. 17, 2013 in European Application No. 05777317.8 (Publication No. EP1737491) (12 pages).
Third party Submissions dated Nov. 15, 2013 in U.S. Appl. No. 13/433,205 (47 pages).
Third party Submissions dated Feb. 18, 2014 in U.S. Appl. No. 13/433,205 (60 pages).
Thomas, Clayton L., Taber's Cyclopedic Medical Dictionary, F.A. Davis Company, 118-119 (1977).
Thompson, Julia et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., vol. 256:77-88 (1996).
Tiegs, "Experimental hepatitis and role of cytokines," Acta Gastroefiterol Belg vol. 60, p. 176-179 (1997).
Tomlinson, Ian M. et al., "The Repertoire of Human Germline VH Sequences Reveals about Fifty Groups of VH Segments with Different Hypervariable Loops," J. Mol. Biol., vol. 227:776-798 (1992).
Tomlinson, Ian M. et al., "The structural repertoire of the human Vκ domain," The EMBO Journal, vol. 14(18):4628-4638 (1995).
Tracey et al., "Shock and tissue injury by recombinant human cachectin," Science vol. 234, p. 470-474 (1986).
Tracey, Kevin J. et al., "Tumor Necrosis Factor: A Pleiotropic Cytokine and Therapeutic Target," Annu. Rev. Med., vol. 45:491-503 (1994).
Tripathi, M. "Essentials of Medical Pharmacology," Jaypee Brothers Medical Publishers (P) Ltd., New Delhi, Chapter 3:51-56, 5th Ed. (2003).
Tsuda et al., "Dietary Ccyanidin 3-O-β-D-glucoside-rich purple corn color prevents obesity and ameliorates hyperglycemia in mice," J Nutr. vol. 133, p. 2125 (2003).
Upton et al, "Basic Concepts in Population Modeling, Simulation, and Model-Based Drug Development: Part 3—Introduction to Pharmacodynamic Modeling Methods," CPT Pharmacometrics Syst Pharmacol Jan. 2, 2014;3:e88.
Vajdos et al., "Comprehensive Functional Maps of the Antigen-binding Site of an Anti-ErbB2 Antibody Obtained with Shotgun Scanning Mutagenesis," J. Mol. Biol., 320(2):415-428 (2002).

(56) References Cited

OTHER PUBLICATIONS

Van Assche et al., "Progressive Multifocal Leukoencephalopathy after Natalizumab Therapy for Crohn's Disease," N Engl J Med, vol. 353:362-368 (2005).
van de Putte, Atkins Malaise et al., "Adalimumab (D2E7) Monotherapy in the Treatment of Patients with Severely Active Rheumatoid Arthritis (RA)," Arthritis Rheum., vol. 46(9 Suppl.):S171 (2002).
van de Putte, et al., "A Single Dose Placebo Controlled Phase I Study of the Fully Human Anti-TNF Antibody D2E7 in Patients with Rheumatoid Arthritis," Arthritis Rheum., vol. 41:S57 (1998).
van de Putte, et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," Ann. Rheum. Dis., vol. 61(Suppl. 1):S168 (2002).
van de Putte, et al., "Efficacy of the Fully Human anti-TNF Antibody D2E7 in Rheumatoid Arthritis," Arthritis & Rheumatism, vol. 42(9):5400, No. 1977 ( 1999).
van de Putte, L. B. A. et al., "Efficacy and Safety of the Fully Human Anti-Tumour Necrosis Factor α Monoclonal Antibody Adalimumab (D2E7) in DMARD Refractory Patients with Rheumatoid Arthritis: a 12 Week, Phase II Study," Ann. Rheum. Dis., 62:1168-1177 (2003).
van de Putte, L. B. A. et al., "Eine placebo-kontrollierte Phase-1-Studie des humanen AntiTNF-Antikorpers D2E7 bei Patienten mit aktiver chronischer Polyarthritis," Z. Rheumatol., vol. 58(Suppl. 1):1/34, F19 (1999).
van de Putte, L. B. A. et al., "One Year Efficacy Results of the Fully Human Anti-TNF Antibody D2E7 in Rheumatoid Arthritis," Arthritis Rheum., vol. 43(9 Suppl.):S269 (2000).
van de Putte, L. B. A. et al., "Sustained 5-Year Efficacy of Adalimumab (HUMIRATM) Monotherapy in DMARD-Refractory rheumatoid arthritis (RA)," Arthritis Rheum., vol. 48(Suppl. 9):S314 (2003).
van de Putte, L.B. et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," JCR: Journal of Clinical Rheumatology, vol. 8(Suppl. 3):S89 (2002).
van de Putte, Leo, et al., "Adalimumab, TNF α-Inhibition in the Treatment of Rheumatoid Arthritis," MD Martin Dunitz, Larry W. Moreland, Ed., pp. 71-93 (2003).
Van Den Brande et al., "Infliximab but not Etanercept Induces Apoptosis in Lamina Propria T-Lymphocytes From Patients With Crohn's Disease," Gastoenterology 124:1774-1785 (2003).
Van Den Brande et al., "Infliximab Induced T Lymphocyte Apoptosis in Crohn's Disease," The Journal of Rheumatology 32(74):26-30 (2005).
van der Poll, T. et al., "Effect of postponed treatment with an anti-tumour necrosis factor (TNF) F(ab')2 fragment on endotoxin-induced cytokine and neutrophil responses in chimpanzees," Clin. Exp. Immunol., vol. 100:21-25 (1995).
van Deventer, "Transmembrane TNF-α, Induction of Apoptosis, and the Efficacy of TNF-Targeting Therapies in Crohn's Disease," Gastroenterology, 121(5):1242-1246 (2001).
Van dullemen et al., "Treatment of Crohn's disease with anti-tumor necrosis factor chimeric monoclonal antibody (cA2)," Gastroenterology vol. 109, p. 129-135 (1995).
van Riel, P. L. C. et al., "Long-Term Treatment with Adalimumab (D2E7) Using Background Methotrexate in Active Rheumatoid Arthritis: Results of a 3 Year Study," Arthritis Rheum., vol. 46(9 Suppl.):S534 (2002).
Vasilli, "The pathophysiology of tumor necrosis factors," Annu. Rev. Immunol. vol. 10, p. 411-452 (1992).
Vaughan, Tristan J. et al., "Human antibodies by design," Nature Biotechnology, vol. 16:535-539 (1998).
Velagapudi, R. B. et al., "Pharmacokinetics of Adalimumab (D2E7), a Fully Human Anti-TNF-α Monoclonal Antibody, Following a Single Intravenous Injection in Rheumatoid Arthritis Patients Treated with Methotrexate," Arthritis Rheum., vol. 46(9 Suppl.):S133 (2002).
Velagapudi, Raja B. et al., "Effect of Methotrexate (MTX) Coadministration on the Pharmacokinetics (PK) of Adalimumab (HUMIRA ™, Abbott) Following a Single Intravenous (iv) Injection," Arthritis Rheum., vol. 48(Suppl. 9):S141 (2003).
Verjans et al., "Polymorphism of tumor necrosis factor-alpha (TNF-α) at position-308 in relation to ankylosin spondylitis," Clin Exp Immunol. vol. 97, p. 45-47 (1994).
Verjans et al., "Restriction fragment length polymorphism of the tumor necrosis factor region in patients with ankylosing spondylitis," Arthritis Rheum. vol. 34, p. 486-489 (1991).
Ward, E. Sally et al., "Binding activities of a repertoire of single immunoglobulin variable domains secreted from *Escherichia coli*," Nature, vol. 341:544-546 (1989).
Weaver, "Differentiating the New Rheumatoid Arthritis Biologic Therapies," J. Clin. Rheumatol., 9(2):99-114 (2003).
Weinberg, J.M. et al., "Evidence-based review of Biologic therapy for psoriasis: An overview of infliximab, etanercept, efalizumab and alefacept," Advanced Studies in Medicine, 5(4):195-206 (2005).
Weinblatt, M. et al., "The ARMADA Trial: Efficacy and Safety of Adalimumab in Patients with Active RA at 24 Months," Ann. Rheum. Dis., vol. 62(Suppl. 1):98 (2003).
Weinblatt, Michael E. et al., "Adalimumab, a Fully Human Anti-Tumor Necrosis Factor α Monoclonal Antibody, for the Treatment of Rheumatoid Arthritis in Patients Taking Concomitant Methotrexate," Arthritis & Rheumatism, vol. 48(1):35-45 (2003).
Weinblatt, Michael E. et al., "The ARMADA Trial: Sustained Improvement and Tolerability in Long-Term Follow-Up of Patients Treated with Adalimumab (HUMIRA™)," Arthritis Rheum., vol. 48(Suppl. 9):S314 (2003).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, 25(6):1700-1721 (2003).
Weisman, Michael et al., "A Dose Escalation Study Designed to Demonstrate the Safety, Tolerability and Efficacy of the Fully Human Anti-TNF Antibody, D2E7, Given in Combination with Methotraxate," Arthritis Rheum., vol. 43(9 Suppl.):S391 (2000).
Weisman, Michael H. et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, vol. 25(6):1700-1721 (2003).
Wellborne, F. et al., "Adalimumab (D2E7), a Fully Human Anti-TNF-α Monoclonal Antibody, Improved Health-Related Quality of Life in Patients with Active Rheumatoid Arthritis Despite Concomitant Methotrexate Therapy," Arthritis Rheum., vol. 46(9 Suppl.):S518 (2002).
Wells, A. F. et al., "Incidence of Injection-Site Reactions Associated with Adalimumab (D2E7) Give Subcutaneously for at Least 6 Months: A Retrospective Analysis of 4 Phase II/III Clinical Trials," Arthritis Rheum., vol. 46(9 Suppl.):S171 (2002).
Wells, A. F. et al., "Injection-site Reactions in Adalimumab Rheumatoid Arthritis (RA) Pivotal Clinical Trials," Ann. Rheum. Dis., vol. 62(Suppl. 1):411 (2003).
Whyte et al., "Increased risk of fibrosing alveolitis associated with interleukin-1 receptor antagonis and tumor necrosis factor-α gene polymorphisms," Am J Respir Crit Care Med. vol. 162, p. 755-758 (2000).
Wiendl, Heinz et al., "Therapeutic Approaches in Multiple Sclerosis, Lessons from Failed and Interrupted Treatment Trials," Biodrugs, vol. 16(3):183-200 (2002).
Winter, Greg et al., "Making Antibodies by Phage Display Technology," Annu. Rev. Immunol., vol. 12:433-455 (1994).
Winter, Greq et al, "Humanized antibodies," Immunology Today, vol. 14(6):243-246 (1993).
Wolfe et al., "Tuberculosis Infection in Patients With Rheumatoid Arthritis and the Effect of Infliximab Therapy," Arthritis & Rheumatism, vol. 50(2):372-379 (2009).

(56) References Cited

OTHER PUBLICATIONS

Yakeuchi T. et al., "Anti-TNF Therapy in Rheumor Arthritis," Jpn. J. Clin. Immunol., 27(1):7-15 (2004).
Youdim et al., "A Pilot Study of Adalimumab in Infliximab-Allergic Patients," Inflammatory Bowel Diseases, 10(4):333-338 (2004).
Zandaman-Goddard, Gisele, "Infection and Anti-Tumor Necrosis Factor-Alpha Therapy," IMAJ, vol. 5:814-816 (2003).
Zeidler, "Undifferentiated spondyloarthropathies," Rheum Dis Clin North Am. vol. 18, p. 187-202 (1992).
Zhang et al. "Enhanced IL-1β and tumor necrosis factor-α release and messenger RNA expression in macrophages from idiopathic pulmonary fibrosis or after asbestos exposure," J Immunol vol. 150, p. 4188-4196 (1993).
Zhang et al. "Tumor necrosis factor expression in arterial walls of diabetic rats," J Tongji Med Univ. vol. 19, p. 203-205 (1999).
Zhou et al. "effect of anti-tumor necrosis factor-α polyclonal antibody on restenosis after balloon angioplasty in a rabbit atherosclerotic model," Atherosclerosis vol. 161, p. 153-159 (2002).
Zia-Amirhosseini et al., "Pharmacokinetics and Pharmacodynamics of SB-240563, a Humanized Monoclonal Antibody Directed to Human Interleukin-5, in Monkeys," J. Pharmacol. Exp. Ther., 291(3):1060-7 (1999).
Zimmerman et al "Lack of TNF-α attenuates intimal hyperplasia after mouse carotid artery injury," Am J Pyhsiol Regul Integr Comp Physiol vol. 283, p. R505-F512 (2002).
Attia et al., "Autoimmunity Correlates with Tumor Regression in Patients with Metastatic Melanoma Treated with Anti-Cytotoxic T-Lymphocyte Antigen-4," J. Clin. Oncol., 23(5):6043-6053 (2005).
Baselga et al., "Phase II Study of Weekly Intravenous Trastuzumab (Herceptin) in Patients with HER2/neu-Overexpressing Metastatic Breast Cancer," Semin. Oncol., 26 (4 Suppl. 12):78-83 (1999).
Colombel et al., "Adalimumab for maintenance of clinical response and remission in patients with Crohn's disease: the CHARM trial," Gastroenterology, 132(1):52-65 (2007).
Eckelbecker, Lisa, "D2E7 Placed Before FDA; Approval Sought for Local Drug," Worcester, Mass. Telegram & Gazette, p. E1 (Apr. 10, 2002).
ERBITUX® (cetuximab) Product Label (Feb. 2004).
FDA Center for Biologics Evaluation and Research (Arthritis Advisory Committee), "Advisory Committee Briefing Document:HUMIRA™ (Adalimumab)," prepared by Abbott Laboratories (Feb. 4, 2003).
Ford et al., "Efficacy of Biological Therapies in Inflammatory Bowel Disease: Systematic Review and Meta-Analysis," Am. J. Gastroenterol. 106(4):644-659 (2011).
Gibaldi, Biopharmaceutics and Clinical Pharmacokinetics, 4th ed., Chapter 12, pp. 234-271 (1991).
Gibaldi, M. & Perrier, D., Pharmacokinetics, 2d ed. (1982).
Goldenberg, "Trastuzumab, a recombinant DNA-derived humanized monoclonal antibody, a novel agent for the treatment of metastatic breast cancer," Clinical Therapeutics, 21(2):309-318 (1999).
HUMIRA® (adalimumab) Label (Jan. 2008).
HUMIRA® (adalimumab) Label (Sep. 2012).
Japsen, Bruce, "Abbott bullish on drug future," Chicago Tribune (Jun. 22, 2001).
Japsen, Bruce, "Drug Dose Boosts Abbott Muscle," Chicago Tribune (Dec. 16, 2000).
Marketletter, "CAT/Abbott's D2E7 in Crohn's disease trials" (Feb. 12, 2001).
Oussalah et al., "Long-term outcome of adalimumab therapy for ulcerative colitis with intolerance or lost response to infliximab: a single-centre experience," Aliment. Pharmacol. Ther., 28(8):966-972 (2008).
Podolsky, "Inflammatory Bowel Disease," N. Engl. J. Med., 347(6):417-429 (2002).
Robert et al., "Phase I Study of Anti- Epidermal Growth Factor Receptor Antibody Cetuximab in Combination with Radiation Therapy in Patients with Advanced Head and Neck Cancer," J. Clin. Oncol., 19(13):3234 3243 (2001).
Rosenberg, Daniel, "Abbott sees new uses for rheumatoid arthritis drug [D2E7]," FirstWord Pharma (Sep. 7, 2002).
Rowland, M. & Tozer, T., Clinical Pharmacokinetics: Concepts and Applications, 3d ed., Chapter 7, pp. 83-105 (1995).
Rutgeerts et al., "Adalimumab Induces and Maintains Mucosal Healing in Patients with Crohn's Disease: Data from the Extend Trial," Gastroenterology, 142(5):1102-1111 (2012).
Sandborn et al., "Adalimumab induction therapy for Crohn's disease previously treated with infliximab: a randomized trial," Ann. Intern. Med., 146(12):829-838 (2007).
Sandborn, "New Concepts in Anti Tumor Necrosis Factor Therapy for Inflammatory Bowel Disease," Rev. Gastroenterol. Disord., 5(1):10-18 (2005).
Sands et al., "Randomized, controlled trial of recombinant human interleukin-11 in patients with active Crohn's disease," Aliment. Pharmacol. Ther., 16(3):399-406 (2002).
Schneider et al, "Safety, pharmacokinetics and biological activity of enlimomab (anti-ICAM-1 antibody): an open-label, dose escalation study in patients hospitalized for acute stroke," Eur. Neurol., 40:78-83 (1998).
Su et al., "Efficacy of anti-tumor necrosis factor therapy in patients with ulcerative colitis," Am. J. Gastroenterol., 97(10):2577-2584 (2002).
Van den Bosch et al., "Effects of a loading dose regimen of three infusions of chimeric monoclonal antibody to tumour necrosis factor α (infliximab) in spondyloarthropathy: an open pilot study," Ann. Rheum. Dis., 59:428-433 (2000).
Wan, Process Mapping—A Necessary Step in Product Lifecycle, BioProcess International Conference (Oct. 7, 2004) (Presentation Slides).
Winsor, "Patients report drug has helped," Worcester, Mass. Telegram & Gazette (Apr. 26, 2000).
2002 REMICADE (infliximab) Label.

\* cited by examiner

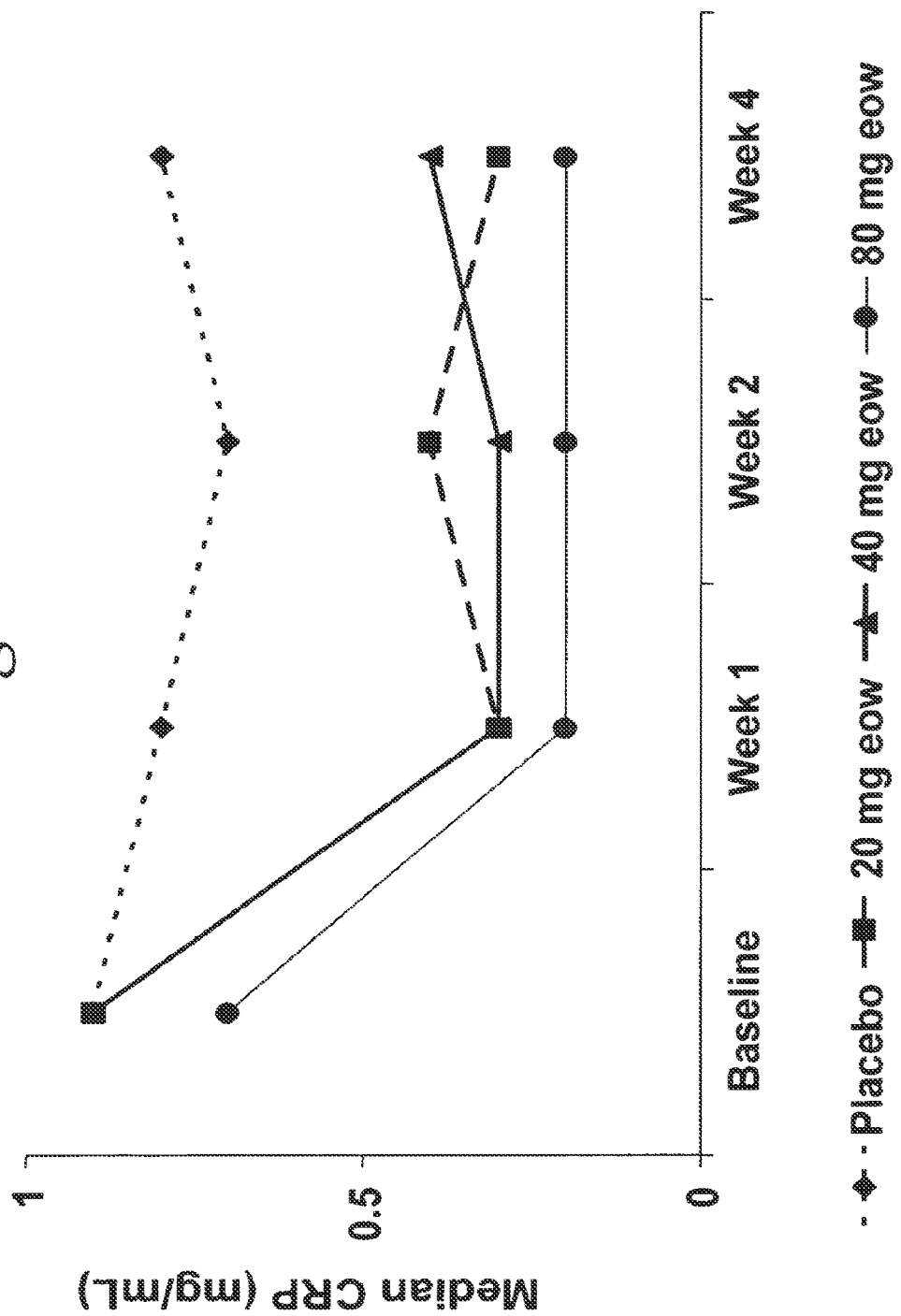

MULTIPLE-VARIABLE DOSE REGIMEN FOR TREATING IDIOPATHIC INFLAMMATORY BOWEL DISEASE

RELATED APPLICATIONS

This application is a continuation of U.S. patent application Ser. No. 14/628,068 (now pending), filed Feb. 20, 2015, which is a continuation of U.S. patent application Ser. No. 14/229,664, filed Mar. 28, 2014, now U.S. Pat. No. 8,961,973, which is a continuation of U.S. patent application Ser. No. 11/104,117, filed Apr. 11, 2005, now U.S. Pat. No. 8,889,136, which claims the benefit of U.S. Provisional Application No. 60/561,139, filed Apr. 9, 2004; U.S. Provisional Application No. 60/561,710, filed Apr. 12, 2004; and U.S. Provisional Application No. 60/569,100, filed May 7, 2004, the contents of each of which applications are hereby incorporated by reference in their entirety.

This application is related to U.S. Pat. Nos. 6,090,382, 6,258,562, and 6,509,015. This application is also related to U.S. patent application Ser. No. 09/801,185, filed Mar. 7, 2001; U.S. patent application Ser. No. 10/302,356, filed Nov. 22, 2002; U.S. patent application Ser. No. 10/163,657, filed Jun. 5, 2002; U.S. patent application Ser. No. 10/133,715, filed Apr. 26, 2002; U.S. patent application Ser. No. 10/222,140, filed Aug. 16, 2002; U.S. patent application Ser. No. 10/693,233, filed Oct. 24, 2003; U.S. patent application Ser. No. 10/622,932, filed Jul. 18, 2003; U.S. patent application Ser. No. 10/623,039, filed Jul. 18, 2003; U.S. patent application Ser. No. 10/623,076, filed Jul. 18, 2003; U.S. patent application Ser. No. 10/623,065, filed Jul. 18, 2003; U.S. patent application Ser. No. 10/622,928, filed Jul. 18, 2003; U.S. patent application Ser. No. 10/623,075, filed Jul. 18, 2003; U.S. patent application Ser. No. 10/623,035, filed Jul. 18, 2003; U.S. patent application Ser. No. 10/622,683, filed Jul. 18, 2003; U.S. patent application Ser. No. 10/622,205, filed Jul. 18, 2003; U.S. patent application Ser. No. 10/622,210, filed Jul. 18, 2003; U.S. patent application Ser. No. 10/623,318, filed Jul. 18, 2003; and U.S. patent application Ser. No. 10/422,287, filed Apr. 24, 2003. The entire contents of each of these patents and patent applications are hereby incorporated herein by reference.

SEQUENCE LISTING

The instant application contains a Sequence Listing which has been submitted electronically as a text file in ASCII format and is hereby incorporated by reference in its entirety. Said text file, created on Jul. 20, 2015, is named 110222-0010-112_Sequence_Listing.txt and is 12,508 bytes in size.

BACKGROUND OF THE INVENTION

Cytokines, such as interleukin-1 (IL-1) and tumor necrosis factor (TNF) are molecules produced by a variety of cells, such as monocytes and macrophages, which have been identified as mediators of inflammatory processes. Cytokines, including TNF, regulate the intensity and duration of the inflammatory response which occurs as the result of an injury or infection. Elevated levels of TNF play an important role in pathologic inflammation. TNF also referred to as (TNFα) has been implicated in the pathophysiology of a variety of human diseases and disorders, including sepsis, infections, autoimmune diseases, transplant rejection and graft-versus-host disease (see e.g., Moeller et al. (1990) *Cytokine* 2:162; U.S. Pat. No. 5,231,024 to Moeller et al.; European Patent Publication No. 260 610 B1 by Moeller, A. et al.; Vasilli (1992) *Annu. Rev. Immunol.* 10:411; Tracey and Cerami (1994) *Annu. Rev. Med.* 45:491).

TNF has been implicated in psoriasis. Expression of TNF-induced proteins and the presence of activated T lymphocytes in psoriatic plaques but not uninvolved skin, suggest their involvement in the pathogenesis of the disease. There are several types of psoriasis according to cutaneous manifestations: plaque psoriasis, guttate psoriasis, erythrodermic psoriasis, generalized pustular and localized pustular psoriasis. Plaque psoriasis is the most common type, however. Treatment of psoriasis depends on the extent of the disease. Topical corticosteroids are commonly used for mild to moderate localized cases. Keratolytic agents and coal tar are also used as topical medications, and phototherapy is commonly used for more widespread disease. Other systemic therapy, such as methotrexate cyclosporine and synthetic retinoids are effective, but are often administered in rotation due to their possible cumulative toxic effect.

TNF has also been implicated in Crohn's disease. Crohn's is diagnosed on the basis of clinical, endoscopic, radiographic, and histologic criteria. The treatment of Crohn's disease is challenging. Treatment is based on location, extent, and severity of disease. Current compounds and regimens do not completely abate the inflammatory process and have significant side effects.

SUMMARY OF THE INVENTION

There is a need to treat TNFα-related disorders, where TNFα activity is detrimental, in a safe and effective manner. The present invention includes multiple-variable dose methods for improved treatment of TNFα-related disorders where TNFα activity is detrimental.

The invention describes a multiple-variable dose method for treating a disorder in which TNFα activity is detrimental, comprising administering to a subject in need thereof at least one induction dose of a TNFα inhibitor such that a threshold level of TNFα inhibitor is achieved within an induction phase; and subsequently administering to the subject at least one treatment dose of the TNFα inhibitor within a treatment phase, such that treatment occurs.

The invention also describes a multiple-variable dose method for treating Crohn's disease, comprising administering to a subject in need thereof at least one induction dose of a TNFα inhibitor such that a threshold level of TNFα inhibitor is achieved within an induction phase; and subsequently administering to the subject at least one treatment dose of the TNFα inhibitor within a treatment phase, such that treatment occurs. The multiple-variable dose method of the invention can also be used to treat ulcerative colitis or psoriasis. In another embodiment, multiple-variable dose method of the invention is used to treat as psoriasis in combination with psoriatic arthritis.

The invention includes a multiple-variable dose method of inducing remission of Crohn's disease, comprising administering to a subject in need thereof at least one induction dose of a TNFα inhibitor such that a threshold level of TNFα inhibitor is achieved within an induction phase; and subsequently administering to the subject at least one treatment dose of the TNFα inhibitor within a treatment phase, such that treatment occurs.

In an additional embodiment, the invention includes a multiple-variable dose method of reducing psoriatic plaques comprising administering to a subject in need thereof at least one induction dose of a TNFα inhibitor such that a threshold level of TNFα inhibitor is achieved within an induction phase; and subsequently administering to the subject at least one treatment dose of the TNFα inhibitor within a treatment phase, such that treatment occurs.

In one embodiment, the TNFα inhibitor is etanercept or infliximab.

In one embodiment of the invention, the TNFα inhibitor is a TNFα antibody, or antigen-binding fragment thereof. In another embodiment of the invention, the TNFα inhibitor is a human TNFα antibody, or antigen-binding fragment thereof. In one embodiment, the antibody is an isolated human antibody, or an antigen-binding portion thereof, that dissociates from human TNFα with a $K_d$ of $1\times10^{-8}$ M or less and a $K_{off}$ rate constant of $1\times10^{-3}$ $s^{-1}$ or less, both determined by surface plasmon resonance, and neutralizes human TNFα cytotoxicity in a standard in vitro L929 assay with an $IC_{50}$ of $1\times10^{-7}$ M or less. In another embodiment, the antibody has the following characteristics:

a) dissociates from human TNFα with a $K_{off}$ rate constant of $1\times10^{-3}$ $s^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In still another embodiment, the antibody has a light chain variable region (LCVR) comprising the amino acid sequence of SEQ ID NO:1 and a heavy chain variable region (HCVR) comprising the amino acid sequence of SEQ ID NO:2. In a further embodiment, the antibody is D2E7.

The methods of the invention can be used to treat a TNFα-related disorder selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, and vasculitis. In one embodiment, the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome. In another embodiment, the TNFα-related disorder is selected from the group consisting of inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, and radiation toxicity. In still another embodiment, the TNFα-related disorder is selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In one embodiment of the invention, the TNFα-related disorder is Crohn's disease. In another embodiment, the disorder is ulcerative colitis. In still another embodiment, the disorder is psoriasis. In still another embodiment, the disorder is psoriasis in combination with psoriatic arthritis (PsA). In still another embodiment, the TNFα-related disorder is rheumatoid arthritis.

In one embodiment, the treatment dose is 40-60% of the induction dose.

In one embodiment, the induction dose used in the multiple variable dose regimen of the invention ranges from about 20 to 200 mg. In another embodiment, the induction dose ranges from about 80 to 160 mg.

In one embodiment, the treatment dose used in the multiple variable dose regimen of the invention ranges from about 20 to 120 mg. In another embodiment, the treatment dose ranges from about 40 to 80 mg.

In one embodiment of the invention, the induction dose comprises about 160 mg. In another embodiment, the treatment dose comprises about 80 mg.

In one embodiment of the invention, the induction dose comprises about 80 mg. In still another embodiment, the treatment dose comprises about 40 mg.

In one embodiment, the induction dose used in the multiple variable dose regimen of the invention ranges from 20 to 200 mg. In another embodiment, the induction dose ranges from 80 to 160 mg. In one embodiment, the treatment dose used in the multiple variable dose regimen of the invention ranges from 20 to 120 mg. In another embodiment, the treatment dose ranges from 40 to 80 mg.

In still another embodiment of the invention, the induction dose comprises 160 mg. In yet another embodiment, the treatment dose comprises 80 mg.

In one embodiment of the invention, the induction dose comprises 80 mg. In yet another embodiment, the treatment dose comprises 40 mg.

In one embodiment, the treatment dose is administered about 2 weeks following the induction dose.

In one embodiment, the TNFα inhibitor is administered subcutaneously. In another embodiment, the TNFα inhibitor is administered in combination with methotrexate. The methotrexate can be administered, for example, in a dose of between 2.5 mg and 30 mg.

In one embodiment, the threshold level of a multiple dose method of treatment of Crohn's disease is determined by a reduction in the subject's Crohn's Disease Activity Index (CDAI) score.

In one embodiment, the threshold level of a multiple dose method of treatment of psoriasis is determined as a therapeutic effect selected from the group consisting of a reduction in psoriatic plaques, an improvement in the subject's Psoriatic Area Severity Index (PASO, and an improvement in the subject's Physician's Global Assessment (PGA) score.

The invention describes a multiple-variable dose method of inducing remission of Crohn's disease, comprising administering to a subject in need thereof at least one induction dose of D2E7 such that a threshold level of TNFα inhibitor is achieved within an induction phase; and subsequently administering to the subject at least one treatment dose of D2E7 within a treatment phase, such that treatment occurs.

In another embodiment, the invention includes a multiple-variable dose method of reducing psoriatic plaques comprising: administering to a subject in need thereof at least one induction dose of D2E7 such that a threshold level of TNFα inhibitor is achieved within an induction phase; and subsequently administering to the subject at least one treatment dose of the D2E7 within a treatment phase, such that treatment occurs.

The invention provides a kit for the treatment of a disorder in which TNFα activity is detrimental comprising:

a) at least one container comprising an induction dose of a TNFα inhibitor;

b) at least one container comprising a treatment dose a TNFα inhibitor; and c) instructions for administration of the induction dose within an induction phase and the treatment dose of the TNFα inhibitor within a treatment phase.

The invention also describes a kit for the treatment of a disorder in which TNFα activity is detrimental, comprising at least one container comprising an induction dose of a TNFα inhibitor packaged with instructions for administration of the induction dose within an induction phase.

The invention describes a kit for the treatment of a disorder in which TNFα activity is detrimental, comprising at least one container comprising a treatment dose of a TNFα inhibitor packaged with instructions for administration of the treatment dose within a treatment phase.

In one embodiment of the invention, the kit is used for the treatment disorder is selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, and vasculitis. In one embodiment, the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome. In still another embodiment, the TNFα-related disorder is selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In one embodiment of the invention, the kit is used for the treatment disorder is selected from the group consisting of Crohn's disease, ulcerative colitis, psoriasis in combination with psoriatic arthritis, and psoriasis.

In another embodiment, the TNFα inhibitor in the kit is a TNFα antibody, or antigen-binding fragment thereof. In one embodiment, the antibody is an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In another embodiment, the antibody has the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In still another embodiment, the antibody has a light chain variable region (LCVR) comprising the amino acid sequence of SEQ ID NO:1 and a heavy chain variable region (HCVR) comprising the amino acid sequence of SEQ ID NO:2. In yet another embodiment, the antibody is D2E7.

In one embodiment, the TNFα inhibitor of the kit of the invention is etanercept or infliximab.

In one embodiment, the treatment dose provided in the kit is 40-60% of the induction dose.

In one embodiment, the induction dose provided in the kit ranges from about 20 to 200 mg. In another embodiment, the induction dose provided in the kit ranges from 80 to 160 mg.

In one embodiment, the treatment dose provided in the kit ranges from about 20 to 120 mg. In another embodiment, the treatment dose provided in the kit ranges from about 40 to 80 mg.

In one embodiment, the induction dose provided in the kit of the invention comprises about 160 mg. In another embodiment, the treatment dose comprises about 80 mg. In still another embodiment, the induction dose comprises about 80 mg. In yet another embodiment, the treatment dose comprises about 40 mg.

In one embodiment, the induction dose provided in the kit of the invention comprises 160 mg. In another embodiment, the treatment dose comprises 80 mg. In still another embodiment, the induction dose comprises 80 mg. In yet another embodiment, the treatment dose comprises 40 mg.

In yet another embodiment, the container is a pre-filled syringe. In still another embodiment, the kit contains instructions for administering the treatment dose 2 weeks following the induction dose.

The invention also provides method for treating a disorder in which TNFα activity is detrimental, comprising administering to a subject in need thereof, a single dose of a TNFα inhibitor such that the disorder is treated. In one embodiment, the TNFα inhibitor is an anti-TNFα antibody, or an antigen binding portion thereof. In another embodiment, the TNFα inhibitor is a human anti-TNFα antibody, or antigen binding portion thereof, including, for example, a human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In one embodiment, said human antibody, or antigen-binding portion thereof, dissociates from human TNFα with a $K_{off}$ rate constant of $5\times10^{-4}$ s$^{-1}$ or less. In another embodiment, said human antibody, or antigen-binding portion thereof, dissociates from human TNFα with a $K_{off}$ rate constant of $1\times10^{-4}$ s$^{-1}$ or less. In still another embodiment, said human antibody, or antigen-binding portion thereof, neutralizes human TNFα cytotoxicity in a standard in vitro L929 assay with an IC$_{50}$ of $1\times10^{-8}$ M or less. In yet another embodiment, said human antibody, or antigen-binding portion thereof, neutralizes human TNFα cytotoxicity in a standard in vitro L929 assay with an IC$_{50}$ of $1\times10^{-9}$ M or less. In a further embodiment, said human antibody, or antigen-binding portion thereof, neutralizes human TNFα cytotoxicity in a standard in vitro L929 assay with an IC$_{50}$ of $1\times10^{-10}$ M or less. The human antibody, or antigen-binding portion thereof, can also be a recombinant antibody, or recombinant antigen-binding portion thereof. In one embodiment, said human antibody, or an antigen-binding portion thereof, is D2E7. In another embodiment, the single dose is selected from the group consisting of about 80 mg, 40, mg, and 20 mg. In still another embodiment, the administration is by subcutaneous injection. In one embodiment of the invention, the TNFα-related disorder is Crohn's disease. In another embodiment, the disorder is ulcerative colitis. In still another embodiment, the disorder is psoriasis. In still another embodiment, the disorder is psoriasis in combination with psoriatic arthritis (PsA). In still another embodiment, the TNFα-related disorder is rheumatoid arthritis.

BRIEF DESCRIPTION OF THE DRAWINGS

FIG. 3A graphically provides the percentage of patients with a ≥70 point CDAI decrease at four weeks. The P-values represent comparison with the placebo group. FIG. 3B provides a graph of the percentage of patients with a CDAI decrease ≥70 over time; *p=0.015 vs. placebo and **p=0.008 vs. placebo.

FIG. 4A graphically provides the percentage of patients with a ≥100 point CDAI decrease at four weeks (p-values represent comparison with the placebo group). FIG. 4B shows the percentage of patients with a CDAI decrease ≥100 over time; *p=0.002 vs. placebo.

FIG. 5 provides results showing the median CRP levels in Crohn's patients receiving multiple-variable treatments versus the placebo.

DETAILED DESCRIPTION OF THE INVENTION

I. Definitions

Figure 1:
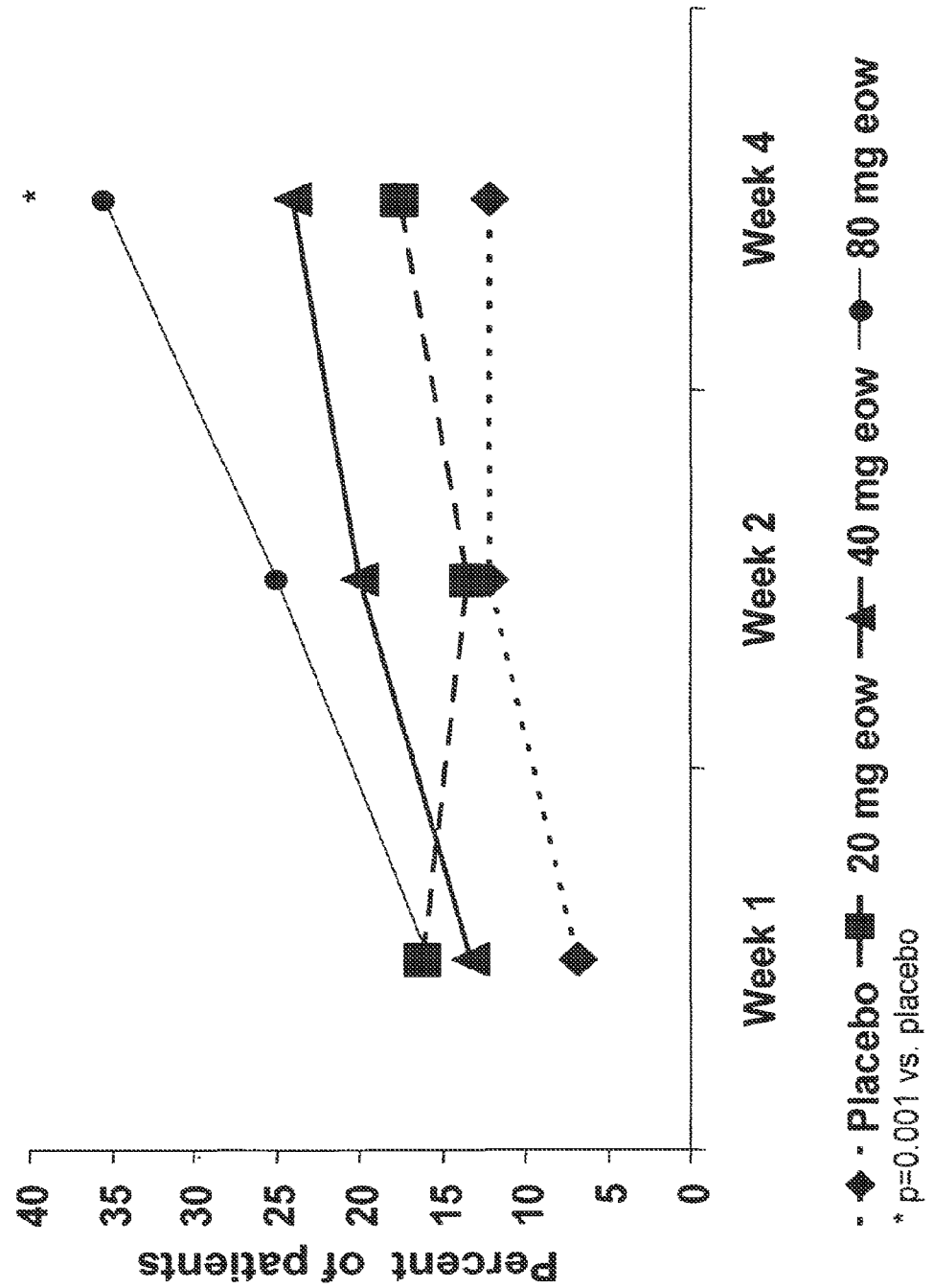
FIG. 1 provides results demonstrating the percentage of patient's with Crohn's disease remission (CDAI<150) over time using the multiple-variable dose regimen.

In order that the present invention may be more readily understood, certain terms are first defined.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. Examples of TNFα inhibitors include etanercept (Enbrel®, Amgen), infliximab (Remicade®, Johnson and Johnson), human anti-TNF monoclonal antibody (D2E7/HUMIRA®, Abbott Laboratories), CDP 571 (Celltech), and CDP 870 (Celltech), as well as other compounds which inhibit TNFα activity, such that when administered to a subject suffering from or at risk of suffering from a disorder in which TNFα activity is detrimental, the disorder is treated. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356, each incorporated by reference herein.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, and in U.S. patent application Ser. Nos. 09/801,185 and 10/302,356, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). The antibody portions of the invention are described in further detail in U.S. Pat. Nos. 6,090,382, 6,258,562, 6,509,015, and in U.S. patent application Ser. Nos. 09/801,185 and 10/302,356, each of which is incorporated herein by reference in its entirety.

Binding fragments are produced by recombinant DNA techniques, or by enzymatic or chemical cleavage of intact immunoglobulins. Binding fragments include Fab, Fab', $F(ab')_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor, L. D. et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "dose," as used herein, refers to an amount of TNFα inhibitor which is administered to a subject.

The term "multiple-variable dose" includes different doses of a TNFα inhibitor which are administered to a subject for therapeutic treatment. "Multiple-variable dose regimen" or "multiple-variable dose therapy" describe a treatment schedule which is based on administering different amounts of TNFα inhibitor at various time points throughout the course of treatment. In one embodiment, the invention describes a multiple-variable dose method of treatment comprising an induction phase and a treatment phase, wherein a TNFα inhibitor is administered at a higher dose during the induction phase than the treatment phase.

The term "induction phase" or "loading phase", as used herein, refers to a period of treatment comprising administration of a TNFα inhibitor to a subject in order to attain a threshold level. During the induction phase, at least one induction dose of TNFα inhibitor is administered to a subject suffering from a disorder in which TNFα is detrimental.

The term "threshold level", as used herein, refers to a therapeutically effective level of a TNFα inhibitor in a subject. A threshold level is achieved by administering at least one induction dose during the induction phase of treatment. Any number of induction doses may be administered to achieve a threshold level of TNFα inhibitor. Once a threshold level is achieved, the treatment phase is initiated.

The term "induction dose" or "loading dose," used interchangeably herein, refers to the first dose of TNFα inhibitor, which is larger in comparison to the maintenance or treatment dose. The induction dose can be a single dose or, alternatively, a set of doses. The induction dose is often used to bring the drug in the body to a steady state amount, and may be used to which to achieve maintenance drug levels quickly. An induction dose is subsequently followed by administration of smaller doses of TNFα inhibitor, i.e., the treatment dose. The induction dose is administered during the induction phase of therapy. In one embodiment of the invention, the induction dose is at least twice the given amount of the treatment dose. In another embodiment of the invention, the induction dose of D2E7 is 160 mg. In another embodiment, the induction dose of D2E7 is 80 mg.

The term "treatment phase" or "maintenance phase", as used herein, refers to a period of treatment comprising administration of a TNFα inhibitor to a subject in order to maintain a desired therapeutic effect. The treatment phase follows the induction phase, and, therefore, is initiated once a threshold level is achieved.

The term "treatment dose" or "maintenance dose" is the amount of TNFα inhibit or taken by a subject to maintain or continue a desired therapeutic effect. A treatment dose is administered subsequent to the induction dose. A treatment dose can be a single dose or, alternatively, a set of doses. A treatment dose is administered during the treatment phase of therapy. Treatment doses are smaller than the induction dose and can be equal to each other when administered in succession. In one embodiment, the invention describes at least one induction dose of D2E7 of about 160 mg, followed by at least one treatment dose of about 80 mg. In another embodiment, the invention describes at least one induction dose of D2E7 of about 80 mg, followed by at least one treatment dose of about 40 mg. In still another embodiment, the treatment dose is administered at least two weeks following the induction dose.

A "dosage regimen" or "dosing regimen" includes a treatment regimen based on a determined set of doses. In one embodiment, the invention describes a dosage regimen for the treatment of Crohn's disease, wherein D2E7 is first administered as an induction dose and then administered in treatment doses which are lower than that of the induction dose.

The term "dosing", as used herein, refers to the administration of a substance (e.g., an anti-TNFα antibody) to achieve a therapeutic objective (e.g., the treatment of a TNFα-associated disorder).

The terms "biweekly dosing regimen", "biweekly dosing", and "biweekly administration", as used herein, refer to the time course of administering a substance (e.g., an anti-TNFα antibody) to a subject to achieve a therapeutic objective (e.g., the treatment of a TNFα-associated disorder). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug, such as a DMARD or NSAID. The other drug(s) may be administered concomitant with, prior to, or following the administration of an anti-TNFα antibody.

The term "TNFα-mediated condition" or "TNFα-related disorder" refers to a local and/or systemic physiological disorder where TNFα is a primary mediator leading to the manifestation of the disorder.

The term "kit" as used herein refers to a packaged product comprising components with which to administer the TNFα antibody of the invention for treatment of a TNFα-related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody D2E7, as described in PCT/IB03/04502 and U.S. application Ser. No. 10/222,140.

Various aspects of the invention are described in further detail herein.

II. TNFα Inhibitors of the Invention

This invention provides a multiple-variable dose method of treating a TNFα-related disorder in which the administration of a TNFα inhibitor is beneficial. In one embodiment, these methods include administration of isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies. The most preferred recombinant, neutralizing antibody of the invention is referred to herein as D2E7, also referred to as HUMIRA® and adalimumab (the amino acid sequence of the D2E7 VL region is shown in SEQ ID NO: 1; the amino acid sequence of the D2E7 VH region is shown in SEQ ID NO: 2). The properties of D2E7 (HUMIRA®) have been described in Salfeld et al., U.S. Pat. Nos. 6,090,382, 6,258,562, and 6,509,015, which are each incorporated by reference herein. Other examples of TNFα inhibitors include chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the multiple-variable dose method of the invention includes the administration of D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In one embodiment, the invention provides multiple-variable dose treatment with an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to multiple-variable dose methods of treating a TNFα-related disorder in which the TNFα activity is detrimental by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the invention provides multiple-variable dose methods of treating a TNFα-related disorder by the administration of an isolated human antibody, or antigen-binding portion thereof. The antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα with a $K_{off}$ of $1 \times 10^{-4}$ s$^{-1}$ or less.

In yet another embodiment, the invention provides multiple-variable dose methods of treating a TNFα-related disorder by the administration of an isolated human antibody, or antigen-binding portion thereof. The antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa I$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H 3$ human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the invention provides multiple-variable dose methods of treating a TNFα-related disorder by the administration of an isolated human antibody, or antigen-binding portion thereof. The antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention provides multiple-variable dose methods of treating a TNFα-related disorder in which the administration of an anti-TNFα antibody is beneficial administration of an isolated human antibody, or an antigen-binding portions thereof. The antibody or antigen-binding portion thereof preferably contains D2E7-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In another embodiment, the TNFα inhibitor of the invention is etanercept (described in WO 91/03553 and WO 09/406476), infliximab (described in U.S. Pat. No. 5,656, 272), CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, or a pegylated soluble TNF receptor Type I (PEGs TNF-R1).

The TNFα antibody of the invention can be modified. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat TNFα-related disorders of the invention by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7- related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human antibodies with high affinity and a low off rate constant for hTNFα are also described in U.S. Pat. Nos. 6,090,382, 6,258,562, and 6,509,015, each of which is incorporated by reference herein.

III. Uses of the TNFα Inhibitors of the Invention

The invention provides a multiple-variable dose method for inhibiting TNFα activity in a subject suffering from a disorder in which TNFα activity is detrimental. TNFα has been implicated in the pathophysiology of a wide variety of disorders (see e.g., Moeller, A., et al. (1990) *Cytokine* 2:162-169; U.S. Pat. No. 5,231,024 to Moeller et al.; European Patent Publication No. 260 610 B1 by Moeller, A.). TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). The invention provides multiple-variable dose methods for inhibiting TNFα activity in a subject suffering from a TNFα-related disorder, which method comprises administering to a subject an initial induction dose and subsequently administering a treatment dose of an antibody, antibody portion, or other TNFα inhibitor, such that TNFα activity is inhibited. Preferably, the TNFα is human TNFα and the subject is a human subject. In one embodiment, the TNFα inhibitor is D2E7, also referred to as HUMIRA® (adalimumab).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of TNFα inhibitors, including antibodies and antibody portions, of the invention in the treatment of specific disorders using a multiple-variable dose therapy is discussed further below:

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey, K. J. and Cerami, A. (1994) *Annu. Rev. Med.* 45:491-503; Russell, D and Thompson, R. C. (1993) *Curr. Opin. Biotech.* 4:714-721). The multiple-variable dose methods of the invention can be used to treat sepsis in any of its clinical settings, including septic shock, endotoxic shock, gram negative sepsis and toxic shock syndrome.

Furthermore, to treat sepsis, an anti-hTNFα antibody, or antibody portion, of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510). Other combination therapies including multiple-variable dose therapies for the treatment of sepsis are discussed further in subsection IV. In a preferred embodiment, an anti-TNFα antibody or antibody portion is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

TNFα inhibitors, including human antibodies, and antibody portions such as D2E7, may be used in a multiple-variable dose method to treat autoimmune diseases, in particular those associated with inflammation. Examples of such autoimmune conditions include rheumatoid arthritis, rheumatoid spondylitis, osteoarthritis and gouty arthritis, allergy, multiple sclerosis, autoimmune diabetes, autoimmune uveitis and nephrotic syndrome. Other examples of autoimmune conditions include multisystem autoimmune diseases and autoimmune hearing loss.

Typically, the antibody, or antibody portion, is administered systemically, although for certain disorders, local administration of the antibody or antibody portion at a site of inflammation may be beneficial (e.g., local administration in the joints in rheumatoid arthritis or topical application to diabetic ulcers, alone or in combination with a cyclohexanylidene derivative as described in PCT Publication No. WO 93/19751). TNFα inhibitors, including human antibodies, and antibody portions such as D2E7, also can be administered with one or more additional therapeutic agents useful in the multiple-variable dose treatment of autoimmune diseases, as discussed further in subsection IV.

In one embodiment of the invention, a human TNFα antibody is used in multiple-variable dose therapy to treat autoimmune disorders such as lupus. Lupus is has been shown to be associated with TNF activity (Shvidel et al. (2002) *Hematol J.* 3:32; Studnicka-Benke et al. (1996) *Br J Rheumatol.* 35:1067). The term "lupus" as used herein refers to a chronic, inflammatory autoimmune disorder called lupus erythematosus that may affect many organ systems including the skin, joints and internal organs. Lupus is a general term which includes a number of specific types of lupus, including systemic lupus, lupus nephritis, and lupus cerebritis. In systemic lupus (SLE), the body's natural defenses are turned against the body and rogue immune cells attack the body's tissues. Antibodies may be produced that can react against the body's blood cells, organs, and tissues. This reaction leads to immune cells attacking the affected systems, producing a chronic disease. Lupus nephritis, also referred to as lupus glomerular disease, is kidney disorder that is usually a complication of SLE, and is characterized by damage to the glomerulus and progressive loss of kidney function. Lupus cerebritis refers to another complication of SLE, which is inflammation of the brain and/or central nervous system.

Another autoimmune disease which can be treated using the multiple-variable dose treatment of the invention is Crohn's disease, which is described in more detail below in the Intestinal Disorders Section.

C. Infectious Diseases

Tumor necrosis factor has been implicated in mediating biological effects observed in a variety of infectious diseases. For example, TNFα has been implicated in mediating brain inflammation and capillary thrombosis and infarction in malaria. TNFα also has been implicated in mediating brain inflammation, inducing breakdown of the blood-brain barrier, triggering septic shock syndrome and activating venous infarction in meningitis. TNFα also has been implicated in inducing cachexia, stimulating viral proliferation and mediating central nervous system injury in acquired immune deficiency syndrome (AIDS). Accordingly, antibodies, and antibody portions, directed against TNF, can be used in multiple-variable dose treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze et al. (1994) *Transplantation* 58:675). The antibodies, and antibody portions, of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Eason et al. (1995) *Transplantation* 59:300; Suthanthiran and Strom (1994) *New Engl. J. Med.* 331:365). Accordingly, the antibodies, and antibody portions, of the invention, can be used to inhibit transplant rejection using multiple-variable dose treatment, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies. Accordingly, antibodies, and antibody portions, which directed against TNF, can be used in the multiple-variable dose treatment of malignancies, wherein treatment inhibits tumor growth or metastasis and/or alleviates cachexia secondary to malignancy. The antibody, or antibody portion, may be administered systemically or locally to the tumor site.

F. Pulmonary Disorders

Tumor necrosis factor has been implicated in the pathophysiology of adult respiratory distress syndrome (ARDS), including stimulating leukocyte-endothelial activation, directing cytotoxicity to pneumocytes and inducing vascular leakage syndrome. The multiple-variable dose methods of the invention can be used to treat various pulmonary disorders, including adult respiratory distress syndrome, using multiple-variable dose treatment (see e.g., PCT Publication No. WO 91/04054), shock lung, chronic pulmonary inflammatory disease, pulmonary sarcoidosis, pulmonary fibrosis and silicosis. The antibody, or antibody portion, may be administered systemically or locally to the lung surface, for example as an aerosol. An antibody, or antibody portion, also can be administered with one or more additional therapeutic agents useful in the multiple-variable dose treatment of pulmonary disorders, as discussed further in subsection IV.

Other examples of pulmonary disorders in which TNFα has been implicated in the pathophysiology include idiopathic interstitial lung disease and chronic obstructive airway disorders (see e.g., Piquet et al. (1989) *J Exp Med.* 170:655; Whyte et al. (2000) *Am J Respir Crit Care Med.* 162:755; Anticevich et al. (1995) *Eur J Pharmacol.* 284:221). The invention further provides methods for treating TNFα activity in a subject suffering from such a pulmonary disorder, which method comprises administering to the subject an antibody, antibody portion, or other TNFα inhibitor using a multiple variable dose regimen such that TNFα activity in the subject suffering from idiopathic interstitial lung disease or a chronic obstructive airway disorder is inhibited. Examples of idiopathic interstitial lung diseases and chronic obstructive airway disorders in which TNFα activity is detrimental are discussed further below.

1. Idiopathic Interstitial Lung Disease

In one embodiment, the TNFα antibody of the invention is used in multiple-variable dose treatment regimen to treat subjects who have an idiopathic interstitial lung disease. The term "idiopathic pulmonary fibrosis" or "IPF" refers to a group of disorders characterized by inflammation and eventually scarring of the deep lung tissues, leading to shortness of breath. The scarring of the alveoli (air sacs) and their supporting structures (the interstitium) in IPF eventually leads to a loss of the functional alveolar units and a reduction of the transfer of oxygen from air to blood. IPF is also referred to as diffuse parenchymal lung disease; alveolitis; cryptogenic fibrosing alveolitis (CFA); idiopathic pulmonary pneumonitis (IPP); and usual interstitial pneumonitis (UIP). IPF is often used synonymously with UIP ("IPF/UIP") because UIP is the most common cellular pattern seen in the pathologic diagnosis of IPF.

Idiopathic interstitial lung diseases affect the lungs in three ways: first, the lung tissue is damaged in some known or unknown way; second, the walls of the air sacs in the lung become inflamed; and finally, scarring (or fibrosis) begins in the interstitium (or tissue between the air sacs), and the lung becomes stiff. Examples of idiopathic interstitial lung diseases include idiopathic pulmonary fibrosis (IPF). Tumor necrosis factor has been implicated in the pathophysiology of idiopathic pulmonary fibrosis (IPF) (see Piquet et al. (1989) *J Exp Med.* 170:655; Whyte et al. (2000) *Am J Respir Crit Care Med* 162:755 Corbett et al. (2002) *Am J Respir Crit Care Med.* 165:690). For example, it has been found that IPF patients have increased levels of TNF expression in macrophages and in type II epithelial cells (Piquet et al. (1993) *Am J Pathol* 143:651; Nash et al. (1993) *Histopathology* 22:343; Zhang et al. (1993) *J Immunol* 150:4188). Certain genetic polymorphisms are also associated with increased TNF expression, and are implicated in playing a role in IPF and silicosis (Whyte et al., supra; Corbett et al., supra).

Patients with IPF often exhibit certain symptoms, including a dry cough, chest pain, and/or shortness of breath. Commonly used drugs for the treatment of IPF are prednisone and cytoxan, although only a fraction of patients improve with continued use of these drugs (American Thoracic Society (2000) *Am. J. Respir. Crit. Care Med.* 161: 646). Oxygen administration and transplantation of the lung are other choices for treatment. In one embodiment, antibodies used in the multiple-variable dose methods of the invention may be used in combination with another therapeutic agent, for example oxygen, for the treatment of idiopathic pulmonary fibrosis.

Examples of animal models used to study idiopathic interstitial lung disease and chronic obstructive airway disorders include ovalbumin (OVA) induced allergic asthma mice and cigarette smoke induced chronic obstructive pulmonary disease mice (see Hessel et al. (1995) *Eur J Pharmacol.* 293:401; Keast et al. (1981) *J. Pathol.* 135:249).

2. Chronic Obstructive Airway Disorder

In one embodiment, a TNFα antibody is used in multiple-variable dose treatment regimen to treat a subject who has a chronic obstructive airflow disorder. In these diseases, airflow obstruction may be chronic and persistent or episodic and recurrent. Airflow obstruction is usually determined by forced expiratory spirometry, which is the recording of exhaled volume against time during a maximal expiration. In a subject who does not have an obstructed airflow, a full forced expiration usually takes between 3 and 4 seconds. In a patient with chronic obstructive airflow disorder, wherein airflow is obstructed, it usually takes up to 15 to 20 seconds and may be limited by breath-holding time. The normal forced expiratory volume in the first second of expiration ($FEV_1$) is easily measured and accurately predicted on the basis of age, sex, and height. The ratio of $FEV_1$ to forced vital capacity ($FEV_1/FVC$) normally exceeds 0.75. Recording airflow against volume during forced expiration and a subsequent forced inspiration—the flow-volume loop—is also useful, mainly for distinguishing upper from lower airway narrowing. Examples of chronic obstructive airway disorders are described below.

a. Asthma

Tumor necrosis factor has been implicated in the pathophysiology of asthma, (Anticevich et al. (1995) *Eur J Pharmacol.* 284:221; Thomas et al. 1995. *Am J Respir Crit Care Med.* 152:76; Thomas and Heywood (2002) *Thorax.* 57:774). For example, acute asthma attacks have been found to be associated with pulmonary neutrophilia and elevated BAL TNF levels (Ordonez et al. (2000) *Am J Respir Crit Care Med* 161:1185). It has been found that the severity of asthma symptoms correlates with endotoxin levels in house dust. In rats, anti-TNF antibodies reduced endotoxin-induced airway changes (Kips et al. (1992) *Am Rev Respir Dis* 145:332).

The term "asthma" as used herein, refers to a disorder in which inflammation of the airways causes airflow into and out of the lungs to be restricted. Asthma is also referred to as bronchial asthma, exercise induced asthma—bronchial, and reactive airways disease (RAD). In some instances, asthma is associated with allergies and/or is familial. Asthma includes a condition which is characterized by widespread fluctuations in the diameter or caliber of bronchial airways over short periods of time, resulting in changes in lung function. The resulting increased resistance to air flow produces symptoms in the affected subject, including breathlessness (dyspnea), chest constriction or "tightness," and wheezing.

Patients with asthma are characterized according to NIH guidelines, are described as mild intermittent, mild persistent, moderate persistent, and severe persistent (see NAEPP Expert Panel Report Guidelines for the Diagnosis and Management of Asthma-Update on Selected Topics 2002. JACI 2002; 110: S141-S209; Guidelines for the Diagnosis and Management of Asthma. NIH Publication 97-4051, July 1997). Patients diagnosed with moderate persistent asthma are often treated with inhaled corticosteroids. Patients diagnosed with severe persistent asthma are often treated with high dose inhaled corticosteroids and p.o. corticosteroids.

b. Chronic Obstructive Pulmonary Disease (COPD)

Tumor necrosis factor has been implicated in the pathophysiology of chronic obstructive pulmonary disease, (Keatings (2000) *Chest.* 118:971; Sakao et al. (2001) *Am J Respir*

Crit Care Med. 163:420; Sakao et al. (2002) Chest. 122: 416). The term "chronic obstructive pulmonary disease" or "COPD" as used interchangeably herein, refers to a group of lung diseases characterized by limited airflow with variable degrees of air sack enlargement and lung tissue destruction. The term COPD includes chronic bronchitis (mucous hypersecretion with goblet cell submucosal gland hyperplasia), chronic obstructive bronchitis, or emphysema (destruction of airway parenchyma), or combinations of these conditions. Emphysema and chronic bronchitis are the most common forms of chronic obstructive pulmonary disease. COPD is defined by irreversible airflow obstruction.

In COPD, chronic inflammation leads to fixed narrowing of small airways and lung parenchyma and alveolar wall destruction (emphysema). This is characterized by increased numbers of alveolar macrophages, neutrophils, and cytotoxic T lymphocytes, and the release of multiple inflammatory mediators (lipids, chemokines, cytokines, growth factors). This inflammation leads to fibrosis with a narrowing of the small airways and lung parenchymal destruction. There is also a high level of oxidative stress, which may amplify this inflammation.

G. Intestinal Disorders

Tumor necrosis factor has been implicated in the pathophysiology of inflammatory bowel disorders including Crohn's disease (see e.g., Tracy et al. (1986) Science 234: 470; Sun et al. (1988) J. Clin. Invest. 81:1328; MacDonald et al. (1990) Clin. Exp. Immunol. 81:301). Chimeric murine anti-hTNFα antibodies have undergone clinical testing for treatment of Crohn's disease (van Dullemen et al. (1995) Gastroenterology 109:129). The invention includes a multiple-variable dose regimen comprising administering a TNFα inhibitor to treat intestinal disorders, such as idiopathic inflammatory bowel disease, using human antibodies, or antigen-binding fragments thereof. Idiopathic inflammatory bowel disease includes two syndromes, Crohn's disease and ulcerative colitis. In one embodiment, the multiple-variable dose regimen of the invention is also used to treat disorders often associated with IBD and Crohn's disease. The term "inflammatory bowel disorder (IBD)-related disorder" or "Crohn's disease-related disorder," as used interchangeably herein, is used to describe conditions and complications commonly associated with IBD and Crohn's disease.

The invention includes a multiple-variable dose regimen comprising administering a TNFα inhibitor to treat Crohn's disease. The treatment of Crohn's disease is based on location, extent, and severity of disease. Pharmacologic interventions include anti-inflammatory agents (aminosalicylates and corticosteroids) and immunomodulatory agents (azathioprine and 6-mercaptopurine [6-MP], cyclosporine, methotrexate [MTX], antibiotic agents, and biologic agents). C-reactive protein (CRP) and erythrocyte sedimentation rate (ESR) levels reflect non-specific acute phase reactions. Endoscopy is a primary means of diagnosing Crohn's disease. Radiologic features of Crohn's disease are shown by barium examination includes mucosal edema, aphthous and linear ulcerations, asymmetrical narrowing and strictures, and separation of adjacent loops of bowel caused by mesenteric thickening. Abnormalities are focal and asymmetric. The primary histologic lesion is an aphthous ulcer. Subjects with Crohn's disease can be evaluated using the Crohn's Disease Activity Index (CDAI), which is a standard measure of the severity of the disease with higher scores indicating more severe disease activity.

Examples of Crohn's disease-related disorders which can be treated using the methods of the invention include fistulas in the bladder, vagina, and skin; bowel obstructions; abscesses; nutritional deficiencies; complications from corticosteroid use; inflammation of the joints; erythem nodosum; pyoderma gangrenosum; and lesions of the eye. Other disorders commonly associated with Crohn's disease include Crohn's-related arthralgias, fistulizing Crohn's, indeterminant colitis, and pouchitis.

H. Cardiac Disorders

The multiple-variable dose methods of the invention also can be used to treat in of various cardiac or coronary disorders, including ischemia of the heart (see e.g., European Patent Application Publication No. EP 453 898) and heart insufficiency (weakness of the heart muscle)(see e.g., PCT Publication No. WO 94/20139). TNFα has also been implicated in the pathophysiology of restenosis (see e.g., Clausell et al. (1994), supra; Medall et al. (1997) Heart 78:273).

As used herein, the term "a cardiac disorder in which TNFα activity is detrimental" is intended to include coronary and cardiovascular diseases in which the presence of TNFα in a subject suffering from the disorder has been shown to be or is suspected of being either responsible for the pathophysiology of the disorder or a factor that contributes to a worsening of the disorder, including cardiovascular disorders, e.g., restenosis. The term "cardiovascular disorder" or "coronary disorder" as used interchangeably herein, refers to any disease, disorder, or state involving the cardiovascular system, e.g., the heart, the blood vessels, and/or the blood. A coronary disorder is generally characterized by a narrowing of the blood vessels that supply blood and oxygen to the heart (coronary arteries). Coronary disease may result from the build up of fatty material and plaque. As the coronary arteries narrow, the flow of blood to the heart can slow or stop. Coronary disorders of the invention can apply to any abnormality of an artery, whether structural, histological, biochemical or any other abnormality. An example of coronary heart disease is restenosis. In one embodiment, a coronary disorder refers to any disease, disorder, or state involving the cardiovascular system excluding ischemia of the heart and heart insufficiency.

Coronary disorders in which TNFα activity is detrimental often result from a blockage in an artery. Such a blockage can be caused by a clot, which usually forms in a coronary artery that has been previously narrowed from changes usually related to atherosclerosis. For example, if the atherosclerotic plaque inside the arterial wall cracks, it can trigger the formation of a thrombus, or clot. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. A coronary disorder can be also caused by an imbalance in arterial pressure, a malfunction of the heart, or an occlusion of a blood vessel, e.g., by a thrombus. Coronary disorders includes both coronary artery disease and peripheral vascular disease.

There are numerous examples of cardiac disorders in which TNFα activity is detrimental, including restenosis. The use of the antibodies, antibody portions, and other TNFα inhibitors in multiple-variable dose regimens for treatment of specific coronary disorders is discussed further below. In certain embodiments, a antibody, antibody portion, or other TNFα inhibitor is administered to the subject in combination with another therapeutic agent, as described below.

The invention provides a multiple-variable dose method for inhibiting TNFα activity in a subject with a cardiac disorder. The invention provides multiple-variable dose methods for inhibiting or decreasing TNFα activity in a subject with a coronary disorder, comprising administering to the subject an antibody, or antibody portion, or other TNFα inhibitor of the invention such that TNFα activity in the subject is inhibited or decreased. Preferably, the TNFα is human TNFα and the subject is a human subject. Alternatively, the subject can be a mammal expressing a TNFα with which an antibody of the invention cross-reacts. Still further the subject can be a mammal into which has been introduced hTNFα (e.g., by administration of hTNFα or by expression of an hTNFα transgene). An antibody of the invention can be administered to a human subject for therapeutic purposes.

Moreover, an antibody of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the multiple-variable dose therapeutic efficacy (e.g., testing of dosages and time courses of administration). Commonly used animal models for studying coronary disorders, including restenosis, include the rat or mouse carotid artery ligation model and the carotid artery injury model (Ferns et al. (1991) *Science* 253:1129; Clowes et al. (1983) *Lab. Invest.* 49:208; Lindner et al. (1993) *Circ Res.* 73:792). In the carotid artery ligation model, arterial blood flow is disrupted by ligation of the vessel near the distal bifurcation. As described in Clowes et al., the carotid artery injury model is performed such that the common carotid artery is denuded of endothelium by the intraluminal passage of a balloon catheter introduced through the external carotid artery. At 2 weeks, the carotid artery is markedly narrowed due to smooth muscle cell constriction, but between 2 and 12 weeks the intimal doubles in thickness leading to a decrease in luminal size. Any of these models can be used to determine the potential therapeutic action of the TNFα antibodies of the invention in the prevention and treatment of restenosis in humans.

The invention includes multiple-variable dose regimen for treatment of cardiovascular disorders in which TNFα activity is detrimental, wherein inhibition of TNFα activity is expected to alleviate the symptoms and/or progression of the coronary disease or to prevent the coronary disease. Subjects suffering from or at risk of developing coronary disorders can be identified through clinical symptoms. Clinical symptoms in coronary disease often include chest pain, shortness of breath, weakness, fainting spells, alterations in consciousness, extremity pain, paroxysmal nocturnal dyspnea, transient ischemic attacks and other such phenomena experienced by the patient. Clinical signs of coronary disease can also include EKG abnormalities, altered peripheral pulses, arterial bruits, abnormal heart sounds, rates and wheezes, jugular venous distention, neurological alterations and other such findings discerned by the clinician. Coronary disorders may also be evidenced, for example, by an increase in the concentration of TNFα in a biological fluid of a subject suffering from the disorder (e.g., an increase in the concentration of TNFα in serum, plasma, synovial fluid, etc. of the subject).

Examples of a cardiovascular disorder include, but are not limited to, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, coronary artery spasm, coronary artery disease, valvular disease, arrhythmias, and cardiomyopathies. The use of the antibodies, antibody portions, and other TNFα inhibitors in multiple-variable dose regimens for treatment of specific cardiovascular diseases are discussed further below. In certain embodiments, the antibody, antibody portion, or other TNFα inhibitor is administered to the subject in combination with another therapeutic agent, as described below in section IV.

1. Restenosis

The term "restenosis" as used herein refers to the recurrence of stenosis, which is the narrowing or constriction of an artery. Restenosis often occurs as a preocclusive lesion that develops following a reconstructive procedure in a diseased blood vessel. The term is not only applied to the recurrence of a pre-existing stenosis, but also to previously normal vessels that become partially occluded following vascular bypass. In another embodiment, the invention provides a method of treating restenosis comprising administering the antibody, or antigen binding portion thereof, of the invention to a subject who has or is at risk of developing restenosis.

TNFα has been implicated in the pathophysiology of restenosis (see Zhou et al. (2002) Atherosclerosis. 161:153; Javed et al. (2002) *Exp and Mol Pathol* 73:104). For example, in the murine wire carotid model, TNF −/− mice demonstrated a seven-fold reduction in initial hyperplasia compared to wild type mice (Zimmerman et al. (2002) *Am J Phsiol Regul Integr Comp Physiol* 283:R505). Restenosis can occur as the result of any type of vascular reconstruction, whether in the coronary vasculature or in the periphery (Colburn and Moore (1998) Myointimal Hyperplasia pp. 690-709 in *Vascular Surgery: A Comprehensive Review* Philadelphia: Saunders). For example, studies have reported symptomatic restenosis rates of 30-50% following coronary angioplasties (see Berk and Harris (1995) *Adv. Intern. Med.* 40:455). After carotid endarterectomies, as a further example, 20% of patients studied had a luminal narrowing greater than 50% (Clagett et al. (1986) *J. Vasc. Surg.* 3:10). Restenosis is evidenced in different degrees of symptomotology which accompany preocclusive lesions in different anatomical locations, due to a combination of factors including the nature of the vessels involved, the extent of residual disease, and local hemodynamics.

"Stenosis," as used herein refers to a narrowing of an artery as seen in occlusive disorder or in restenosis. Stenosis can be accompanied by those symptoms reflecting a decrease in blood flow past the narrowed arterial segment, in which case the disorder giving rise to the stenosis is termed a disease (i.e., occlusive disease or restenosis disease). Stenosis can exist asymptomatically in a vessel, to be detected only by a diagnostic intervention such as an angiography or a vascular lab study.

The multiple-variable dose method of the invention can be used to treat a subject suffering from or at risk of developing restenosis. A subject at risk of developing restenosis includes a subject who has undergone PTCA. The subject may have also had a stent inserted to prevent restenosis. The TNFα antibody can be used alone or in combination with a stent to prevent the re-occurrence of stenosis in a subject suffering from cardiovascular disease.

2. Congestive Heart Failure

TNFα has been implicated in the pathophysiology of congestive heart failure (see Zhou et al. (2002) *Atherosclerosis* 161:153). Serum levels of TNFα are elevated in patients with congestive heart failure in a manner which is directly proportional to the severity of the disease (Levine et al. (1990) *N Engl J* Med 323:236; Torre-Amione et al. (1996) *J Am Coll Cardiol* 27:1201). In addition, inhibitors of TNFα have also been shown to improve congestive heart failure symptoms (Chung et al. (2003) Circulation 107: 3133).

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies.

A "subject who has or is suffering from congestive heart failure" is a subject who has a disorder involving a clinical syndrome of diverse etiologies linked by the common denominator of impaired heart pumping in which the heart cannot pump blood commensurate with the requirements of the metabolizing tissues, or can do so only from an elevated filling pressure. A "subject at risk of developing congestive heart failure" is a subject who has a propensity of developing congestive heart failure because of certain factors affecting the cardiovascular system of the subject. It is desirable to reduce the risk of or prevent the development of congestive heart failure in these subjects. The phrase "with congestive heart failure" includes patients who are at risk of suffering from this condition relative to the general population, even though they may not have suffered from it yet, by virtue of exhibiting risk factors. For example, a patient with untreated hypertension may not have suffered from congestive heart failure, but is at risk because of his or her hypertensive condition. In one embodiment of the invention, the antibody D2E7 is used to treat a subject at risk of developing congestive heart failure using multiple-variable dose treatment.

3. Acute Coronary Syndromes

TNFα has been implicated in the pathophysiology of acute coronary syndromes (see Libby (1995) *Circulation* 91:2844). Acute coronary syndromes include those disorders wherein the subject experiences pain due to a blood flow restriction resulting in not enough oxygen reaching the heart. Studies have found that TNFα plays a role in acute coronary syndromes. For example, in a novel rat heterotropic cardiac transplantation-coronary ligation model capable of inducing myocardial infarction in the absence of downstream hemodynamic effects, administration of chimeric soluble TNF receptor (sTNFR) abolished transient LV remodeling and dysfunction (Nakamura, et al. (2003) *J. Cardiol.* 41:41). It was also found that direct injection of an sTNFR expression plasmid to the myocardium, resulted in a reduction in the infarction size in acute myocardial infarction (AMI) experimental rats (Sugano et al. (2002) *FASEB J* 16:1421).

In one embodiment, a TNFα antibody is used in a multiple-variable dose method for the treatment or prevention of an acute coronary syndrome in a subject, wherein the acute coronary syndrome is a myocardial infarction or angina.

As used herein, the term "myocardial infarction" or "MI" refers to a heart attack. A myocardial infarction involves the necrosis or permanent damage of a region of the heart due to an inadequate supply of oxygen to that area. This necrosis is typically caused by an obstruction in a coronary artery from either atherosclerosis or an embolis. MIs which are treated by the TNFα antibody of the invention include both Q-wave and non-Q-wave myocardial infarction. Most heart attacks are caused by a clot that blocks one of the coronary arteries (the blood vessels that bring blood and oxygen to the heart muscle). For example, a clot in the coronary artery interrupts the flow of blood and oxygen to the heart muscle, leading to the death of heart cells in that area. The damaged heart muscle permanently loses its ability to contract, and the remaining heart muscle needs to compensate for it. An MI can also be caused by overwhelming stress in the individual.

The term "angina" refers to spasmodic, choking, or suffocative pain, and especially as denoting angina pectoris which is a paroxysmal thoracic pain due, most often, to anoxia of the myocardium. Angina includes both variant angina and exertional angina. A subject having angina has ischemic heart disease which is manifested by sudden, severe, pressing substernal pain that often radiates to the left shoulder and along the left arm. TNFα has been implicated in angina, as TNFα levels are upregulated in patients with both MI and stable angina (Balbay et al. (2001) *Angiology* 52109).

4. Arteriosclerosis

"Atherosclerosis" as used herein refers to a condition in which fatty material is deposited along the walls of arteries. This fatty material thickens, hardens, and may eventually block the arteries. Atherosclerosis is also referred to arteriosclerosis, hardening of the arteries, and arterial plaque buildup. Polyclonal antibodies directed against TNFα have been shown to be effective at neutralizing TNFα activity resulting in inflammation and restenosis in the rabbit atherosclerotic model (Zhou et al., supra). Accordingly, a TNFα ☐ antibody can be used to treat or prevent subjects afflicted with or at risk of having atherosclerosis using the multiple-variable dose method of the invention.

5. Cardiomyopathy

The term "cardiomyopathy" as used herein is used to define diseases of the myocardium wherein the heart muscle or myocardium is weakened, usually resulting in inadequate heart pumping. Cardiomyopathy can be caused by viral infections, heart attacks, alcoholism, long-term, severe hypertension (high blood pressure), or by autoimmune causes.

In approximately 75-80% of heart failure patients coronary artery disease is the underlying cause of the cardiomyopathy and is designated "ischemic cardiomyopathy." Ischemic cardiomyopathy is caused by heart attacks, which leave scars in the heart muscle or myocardium. The affected myocardium is then unable to contribute to the heart pumping function. The larger the scars or the more numerous the heart attacks, the higher the chance there is of developing ischemic cardiomyopathy.

Cardiomyopathies that are not attributed to underlying coronary artery disease, and are designated "non-ischemic cardiomyopathies." Non-ischemic cardiomyopathies include, but are not limited to idiopathic cardiomyopathy, hypertrophic cardiomyopathy, alcoholic cardiomyopathy, dilated cardiomyopathy, peripartum cardiomyopathy, and restrictive cardiomyopathy.

I. Spondyloarthropathies

TNFα has been implicated in the pathophysiology of a wide variety of disorders, including inflammatory diseases such as spondyloarthropathies (see e.g., Moeller et al. (1990) *Cytokine* 2:162; U.S. Pat. No. 5,231,024; European Patent Publication No. 260 610). The invention provides multiple-variable dose methods for inhibiting TNFα activity in a subject suffering from a spondyloarthropathy, which method comprises administering to the subject an antibody, antibody portion, or other TNFα inhibitor initially in an induction dose, followed by a treatment dose, such that TNFα activity in the subject suffering from a spondyloarthropathy is inhibited.

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include ank/ank transgenic mice, HLA-B27 transgenic rats (see Taurog et al. (1998) *The Spondylarthritides*. Oxford: Oxford University Press).

The multiple-variable dose methods of the invention can also be used to treat subjects who are at risk of developing a spondyloarthropathy using multiple-variable dose methods. Examples of subjects who are at risk of having spondyloarthropathies include humans suffering from arthritis. Spondyloarthropathies can be associated with other forms of arthritis, including rheumatoid arthritis. In one embodiment of the invention, antibodies are used in multiple-variable dose methods to treat a subject who suffers from a spondyloarthropathy associated with rheumatoid arthritis. Examples of spondyloarthropathies which can be treated with a TNFα antibody using the multiple-variable dose method of the invention are described below:

1. Ankylosing Spondylitis (AS)

Tumor necrosis factor has been implicated in the pathophysiology of ankylosing spondylitis (see Verjans et al. (1991) *Arthritis Rheum.* 34:486; Verjans et al. (1994) *Clin Exp Immunol.* 97:45; Kaijtzel et al. (1999) *Hum Immunol.* 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting* Abstract). Accordingly, multiple-variable dose methods comprising administering an antibody, or antigen-binding fragment thereof, of the invention can be used to treat AS.

In one embodiment, the multiple-variable dose method of the invention is used to treat a spondyloarthropathy associated with IBD, including AS. AS is often treated with nonsteroidal anti-inflammatory medications (NSAIDs), such as aspirin or indomethacin. Accordingly, a TNFα antibody used in the multiple-variable dose method of the invention may also be administered in combination with agents commonly used to reduce inflammation and pain commonly associated with ankylosing spondylitis.

2. Psoriatic Arthritis

Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic arthritis or psoriasis associated with the skin, refers to chronic inflammatory arthritis which is associated with psoriasis, which is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. The TNFα antibody, or antigen-binding fragment thereof, of the invention can be used in multiple-variable dose treatment of PsA.

PsA is sometimes associated with arthritis mutilans. Arthritis mutilans refers to a disorder which is characterized by excessive bone erosion resulting in a gross, erosive deformity which mutilates the joint. In one embodiment, the multiple-variable dose method of the invention can be used to treat arthritis mutilans.

3. Reactive Arthritis/Reiter's Syndrome

Tumor necrosis factor has been implicated in the pathophysiology of reactive arthritis, which is also referred to as Reiter's syndrome (Braun et al. (1999) *Arthritis Rheum.* 42(10):2039). Reactive arthritis (ReA) refers to arthritis which complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including chlamydia, campylobacter, salmonella, or yersinia. Accordingly, the multiple-variable dose method of the invention can be used to treat ReA using the multiple-variable dose method of the invention.

4. Undifferentiated Spondyloarthropathies

In one embodiment, multiple-variable dose methods of the invention of the invention are used to treat subjects suffering from undifferentiated spondyloarthropathies (see Zeidler et al. (1992) *Rheum Dis Clin North Am.* 18:187). Other terms used to describe undifferentiated spondyloarthropathies include seronegative oligoarthritis and undifferentiated oligoarthritis. Undifferentiated spondyloarthropathies, as used herein, refers to a disorder wherein the subject demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS. In one embodiment, the multiple-variable dose method of the invention comprises administering different doses of a TNFα antibody, or antigen-binding fragment thereof, to treat undifferentiated spondyloarthropathies.

J. Metabolic Disorders

TNFα has been implicated in the pathophysiology of a wide variety of disorders, including metabolic disorders, such as diabetes and obesity (Spiegelman and Hotamisligil (1993) Cell 73:625; Chu et al. (2000) *Int J Obes Relat Metab Disord.* 24:1085; Ishii et al. (2000) *Metabolism.* 49:1616). The term "metabolic disorder," as used herein, refers to diseases or disorders which affect how the body processes substances needed to carry out physiological functions. Examples of metabolic disorders include, but are not limited to, diabetes and obesity. In one embodiment of the invention, the term "metabolic disorder" is used to refer to disorders which affect how the body processes substances needed to carry out physiological functions, excluding autoimmune diabetes.

The invention provides multiple-variable dose methods for inhibiting TNFα activity in a subject suffering from such a metabolic disorder, which method comprises administering to the subject an induction dose followed by a treatment dose of an antibody, antibody portion, or other TNFα inhibitor such that TNFα activity in the subject suffering from a metabolic disorder is inhibited. TNFα antibodies can also be used to treat subjects who are at risk of developing a metabolic disorder using the multiple-variable dose regimen of the invention.

Metabolic disorders are often associated with arthritis, including rheumatoid arthritis. In one embodiment, a TNFα inhibitor, such as an antibody, is used in a multiple-variable dose regimen in a subject who suffers from a metabolic disorder associated with rheumatoid arthritis. In another embodiment, the multiple-variable dose treatment of the invention comprises administering a TNFα antibody to treat disorders associated with diabetes or obesity.

Examples of animal models for evaluating the efficacy of a multiple-variable dose regimen using a TNFα antibody for the treatment of a metabolic disorder include NOD transgenic mice, Akita mice, NSY transgenic mice and ob/ob mice (see Baeder et al. (1992) *Clin Exp Immunol.* 89:174; Haseyama et al. (2002) *Tohoku J Exp Med.* 198:233; Makino et al. (1980): *Exp. Anim.* 29:1; Kolb (1987) *Diabetes/Metabolism Reviews* 3:751; Hamada et al. (2001) *Metabolism.* 50:1282; Coleman, (1978) *Diabetologia,* 14:141; Bailey et al. (1982) *Int. J. Obesity* 6:11). Examples of animal models used to study vasculitis includes the mouse HSV model (Behcet's disease), the mouse *L. casei* model (Kawasaki's disease), and the mouse ANCA model (Kawasaki's disease). Other models of vasculitis include the McH5-lpr/lpr strain (Nose et al. (1996) *Am. J. Path.* 149:1763) and the SCG/Kj strain of mice (Kinjoh et al. (1993) *Proc. Natl. Acad. Sci., USA* 90:3413). These mice strains spontaneously develop crescentic glomerulonephritis and necrotizing vasculitis of the small arteries and arterioles of the spleen, stomach, heart, uterus and ovaries. These animals develop hypergammaglobulinemia and ANCA autoantibodies that react with myeloperoxidase (MPO). Additionally, immunization of rats with human MPO results in ANCA-associated necrotizing crescentic glomerulonephritis (Brouwer et al. (1993) *J. Exp. Med.* 177:905).

Metabolic disorders affect how the body processes substances needed to carry out physiological functions. A number of metabolic disorders of the invention share certain characteristics, i.e. they are associated the insulin resistance, lack of ability to regulate blood sugar, weight gain, and increase in body mass index. Examples of metabolic disorders include diabetes and obesity. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity. Examples of metabolic disorders which can be treated using multiple-variable dose methods comprising administration of a TNFα antibody are described in more detail below:

1. Diabetes

Tumor necrosis factor has been implicated in the pathophysiology of diabetes. (see e.g., Navarro et al. (2003) *Am J Kidney Dis.* 42:53; Daimon et al. (2003) *Diabetes Care.* 26:2015; Zhang et al. (1999) *J Tongji Med Univ.* 19:203; Barbieri et al. (2003) *Am J Hypertens.* 16:537) For example, TNFα is implicated in the pathophysiology for insulin resistance. It has been found that serum TNF levels in patients with gastrointestinal cancer correlates with insulin resistance (see e.g., McCall et al. (1992) *Br. J. Surg.* 79:1361).

The term "diabetes" or "diabetic disorder" or "diabetes mellitus," as used interchangeably herein, refers to a disease which is marked by elevated levels of sugar (glucose) in the blood. Diabetes can be caused by too little insulin (a chemical produced by the pancreas to regulate blood sugar), resistance to insulin, or both. Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDMM, juvenile onset diabetes, and diabetes—type I. Type 1 diabetes represents is the result of a progressive autoimmune destruction of the pancreatic β-cells with subsequent insulin deficiency.

The term "type 2 diabetes," refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes—type II Diabetes is can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependant diabetes mellitus (type 2 IDDM), non-autoimmune diabetes mellitus, non-insulin-dependant diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14*th* ed., New York, McGraw-Hill).

Diabetes is often treated with diet, insulin dosages, and various medications described herein. Accordingly, a TNFα antibody may also be administered in combination with agents commonly used to treat metabolic disorders and pain commonly associated with diabetes in the multiple-variable dose method of the invention.

In addition, the phrase "disorders associated with diabetes," as used herein, refers to conditions and other diseases which are commonly associated with or related to diabetes. Example of disorders associated with diabetes include, for example, hyperglycemia, hyperinsulinemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis. In one embodiment the multiple-variable dose methods of the invention can be used to treat disorders associated with diabetes.

Diabetes manifests itself in the foregoing categories and can cause several complications that are discussed in the following sections. Accordingly, the antibody, or antigen-binding fragment thereof, of the invention can be used to treat diabetes. In one embodiment, a TNFα antibody, or antigen-binding fragment thereof, is used to treat diabetes associated with the above identified categories using the multiple-variable dose method of the invention. In another embodiment, the invention includes multiple-variable dose regimens comprising administering a TNFα antibody to treat disorders associated with diabetes. Diabetes manifests itself in many complications and conditions associated with diabetes, including the following categories:

a. Diabetic Neuropathy and Peripheral Neuropathy

Tumor necrosis factor has been implicated in the pathophysiology of diabetic neuropathy and peripheral neuropathy. (See Benjafield et al. (2001) *Diabetes Care.* 24:753; Qiang et al. (1998) *Diabetologia.* 41:1321; Pfeiffer et al. (1997) *Horm Metab Res.* 29:111).

The term "neuropathy," also referred to as nerve damage-diabetic, as used herein, refers to a common complication of diabetes in which nerves are damaged as a result of hyperglycemia (high blood sugar levels). A variety of diabetic neuropathies are recognized, such as distal sensorimotor polyneuropathy, focal motor neuropathy, and autonomic neuropathy.

The term "peripheral neuropathy," also known as peripheral neuritis and diabetic neuropathy, as used herein, refers to the failure of the nerves to carry information to and from the brain and spinal cord. Peripheral neuropathy produces symptoms such as pain, loss of sensation, and the inability to control muscles. In some cases, the failure of nerves to control blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

Neuropathies that affect small myelinated and unmyelinated fibers of the sympathetic and parasympathetic nerves are known as "peripheral neuropathies." Furthermore, the related disorder of peripheral neuropathy, also known as peripheral neuritis and diabetic neuropathy, refers to the failure of the nerves to carry information to and from the brain and spinal cord. This produces symptoms such as pain, loss of sensation, and the inability to control muscles. In some cases, failure of nerves controlling blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

The term "diabetic neuropathy" refers to a common complication of diabetes in which nerves are damaged as a result of hyperglycemia (high blood sugar levels). Diabetic neuropathy is also referred to as neuropathy and nerve damage-diabetic. A variety of diabetic neuropathies are recognized, such as distal sensorimotor polyneuropathy, focal motor neuropathy, and autonomic neuropathy.

b. Diabetic Retinopathy

Tumor necrosis factor has been implicated in the pathophysiology of diabetic retinopathy (Scholz et al. (2003) *Trends Microbiol.* 11:171). The term "diabetic retinopathy" as used herein, refers to progressive damage to the eye's retina caused by long-term diabetes. Diabetic retinopathy, includes proliferative retinopathy. Proliferative neuropathy in turn includes neovascularization, pertinal hemorrhage and retinal detachment.

In advanced retinopathy, small vessels proliferate on the surface of the retina. These blood vessels are fragile, tend to bleed and can cause peretinal hemorrhages. The hemorrhage can obscure vision, and as the hemorrhage is resorbed fibrous tissue forms predisposing to retinal detachments and loss of vision. In addition, diabetic retinopathy includes proliferative retinopathy which includes neovascularization, pertinal hemorrhage and retinal detachment. Diabetic retinopathy also includes "background retinopathy" which involves changes occurring with the layers of the retina.

c. Diabetic Ulcerations and Retinopathy Ulcerations

Tumor necrosis factor has been implicated in the pathophysiology of diabetic ulcerations, (see Lee et al. (2003) *Hum Immunol.* 64:614; Navarro et al. (2003) *Am J Kidney Dis.* 42:53; Daimon et al (2003) *Diabetes Care.* 26:2015; Zhang et al. (1999) *J Tongji Med Univ.* 19:203; Barbieri et al. (2003) *Am J Hypertens.* 16:537; Venn et al. (1993) *Arthritis Rheum.* 36:819; Westacott et al. (1994) *J Rheumatol.* 21:1710).

The term "diabetic ulcerations," as used herein, refers to an ulcer which results as a complication of diabetes. An ulcer is a crater-like lesion on the skin or mucous membrane caused by an inflammatory, infectious, malignant condition, or metabolic disorder. Typically diabetic ulcers can be found on limbs and extremities, more typically the feet. These ulcers, caused by diabetic conditions, such as neuropathy and a vascular insufficiency, can lead to ischemia and poor wound healing. More extensive ulcerations may progress to osteomyelitis. Once osteomyelitis develops, it may be difficult to eradicate with antibiotics alone and amputation may be necessary.

The term "retinopathy ulcerations," as used herein refers to an ulcer which causes or results in damages to the eye and the eye's retina. Retinopathy ulcerations may include conditions such has retinoathic hemorrhages.

d. Diabetic Macrovasculopathy

Tumor necrosis factor has been implicated in the pathophysiology of diabetic macrovasculopathy (Devaraj et al. (2000) *Circulation.* 102:191; Hattori et al. (2000) *Cardiovasc Res.* 46:188; Clausell et al. (1999) *Cardiovasc Pathol.* 8:145). The term "diabetic macrovasculopathy," also referred to as "macrovascular disease," as used herein, refers to a disease of the blood vessels that results from diabetes. Diabetic macrovasculopathy complication occurs when, for example, fat and blood clots build up in the large blood vessels and stick to the vessel walls. Diabetic macrovasculopathies include diseases such as coronary disease, cerebrovascular disease, and peripheral vascular disease, hyperglycaemia and cardiovascular disease, and strokes.

2. Obesity

Tumor necrosis factor has been implicated in the pathophysiology of obesity (see e.g., Pihlajamaki J et al. (2003) *Obes Res.* 11:912; Barbieri et al. (2003) *Am J Hypertens.* 16:537; Tsuda et al. (2003) *J Nutr.* 133:2125). The term "obesity" as used herein, refers to a condition in which the subject has an excess of body fat relative to lean body mass. In one embodiment, obesity refers to a condition in which an individual weighs at least about 20% or more over the maximum desirable for their height. When an adult is more than 100 pounds overweight, he or she is considered to be "morbidly obese." In another embodiment, obesity is defined as a BMI (body mass index) over 30 kg/m2. Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea. Obesity can be treated using the multiple-variable dose methods of the invention.

K. Anemia

TNFα has been implicated in the pathophysiology of a wide variety of anemias (see e.g., Jongen-Lavrencic et al. (1997) *J. Rheumatol.* 24:1504; Demeter et al. (2002) *Ann Hematol.* 81:566; DiCato (2003) *The Oncologist* 8 (suppl 1):19). The invention provides multiple-variable dose methods for inhibiting TNFα activity in a subject suffering from anemia, which method comprises administering to the subject an induction dose followed by a treatment dose of a TNFα inhibitor, wherein the TNFα inhibitor is an antibody, antibody portion, such that TNFα activity in the subject suffering from anemia is inhibited. In one embodiment, the anemia is associated with rheumatoid arthritis.

The term "anemia" as used herein, refers to an abnormally low number of circulating red cells or a decreased concentration of hemoglobin in the blood. Examples of anemia related to rheumatoid arthritis include, for example, anemia of chronic disease, iron deficiency anemia, and autoimmune hemolytic anemia. In one embodiment, the invention provides a method of treating anemias related to, for example, anemias related to rheumatoid arthritis, anemias of infection and chronic inflammatory diseases, iron deficiency anemia, autoimmune hemolytic anemia, myelophthisic anemia, aplastic anemia, hypoplastic anemia, pure red cell aplasia and anemia associated with renal failure or endocrine disorders, megaloblastic anemias, defects in heme or globin synthesis, anemia caused by a structural defect in red blood cells, e.g., sickle-cell anemia, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Examples of animal models used to study anemia include rats inoculated with peptidoglycan-polysaccharide polymers (see Coccia et al., (2001) *Exp Hematology.* 29:1201-1209). Examples of animal models used to study pain are well known in the art, and include the rat sciatic nerve ligation model, and the rat segmental spinal nerve ligation model (see Bennett and Zie, (1988) *Pain.* 33:87-107; Kim and Chung, (1992) *Pain* 50:355-363).

L. Pain

TNFα has been implicated in the pathophysiology of a wide variety of pain syndromes (see e.g., Sorkin et al. (1997) *Neuroscience.* 81:255; Huygen et al. (2002) *Mediators Inflamm.* 11:47; Parada et al. (2003) *Eur J Neurosci.* 17:1847). The term "pain" as used herein, refers to all types of pain. The term shall refer to acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term also includes nociceptive pain or nociception.

The invention provides multiple-variable dose methods for inhibiting TNFα activity in a subject suffering from such a pain disorder, which method comprises administering to the subject an induction dose followed by a treatment dose of an antibody, antibody portion, or other TNFα inhibitor such that TNFα activity in the subject suffering from pain is inhibited. Pain has been defined in a variety of ways, including nociceptive pain and neuropathic pain. The most commonly experienced form of pain may be defined as the effect of a stimulus on nerve endings, which results in the transmission of impulses to the cerebrum. Pain is also commonly associated with inflammatory disorders, including, for example, rheumatoid arthritis. In one embodiment, the antibody of the invention is used to treat a subject who suffers from pain associated with rheumatoid arthritis. Examples of pain disorders in which TNFα activity is detrimental are discussed further below.

1. Neuropathic Pain

Tumor necrosis factor has been implicated in the pathophysiology of neuropathic pain (see Sommer (1999) *Schmerz.* 13:315; Empl et al., (2001) *Neurology.* 56:1371; Schafers et al. (2003) *J Neurosci.* 23:3028). As used herein the term "neuropathic pain" refers to pain that results from injury to a nerve, spinal cord, or brain, and often involves neural supersensitivity. Examples of neuropathic pain include chronic lower back pain, pain associated with arthritis, cancer-associated pain, herpes neuralgia, phantom limb pain, central pain, opioid resistant neuropathic pain, bone injury pain, and pain during labor and delivery. Other examples of neuropathic pain include post-operative pain, cluster headaches, dental pain, surgical pain, pain resulting from severe, for example third degree, burns, post partum pain, angina pain, genitourinary tract related pain, and including cystitis.

Neuropathic pain is distinguished from nociceptive pain. Pain involving a nociceptive mechanism usually is limited in duration to the period of tissue repair and generally is alleviated by available analgesic agents or opioids (Myers (1995) *Regional Anesthesia* 20:173). Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra, 1995). Accordingly, the multiple-variable dose methods of the invention can be used to treat neuropathic pain.

2. Nociceptive Pain

As used herein the term "nociceptive pain" refers to pain that is transmitted across intact neuronal pathways, i.e., pain caused by injury to the body. Nociceptive pain includes somatic sensation and normal function of pain, and informs the subject of impending tissue damage. The nociceptive pathway exists for protection of the subject, e.g., the pain experienced in response to a burn). Nociceptive pain includes bone pain, visceral pain, and pain associated with soft tissue.

Tumor necrosis factor has been implicated in the pathophysiology of visceral pain (see Coelho et al. (2000) *Am J Physiol Gastrointest Liver Physiol.* 279:G781; Coelho et al. (2000) *Brain Res Bull.* 52:223). Visceral pain is used to refer to nociceptive pain that is mediated by receptors on A-delta and C nerve fibers. A-delta and C-nerve fibers are which are located in skin, bone, connective tissue, muscle and viscera. Visceral pain can be vague in distribution, spasmodic in nature and is usually described as deep, aching, squeezing and colicky in nature. Examples of visceral pain include pain associated with a heart attack, wherein the visceral pain can be felt in the arm, neck and/or back, and liver capsule pain, wherein the visceral pain can be felt in the back and/or right shoulder. Accordingly, the multiple-variable dose methods of the invention can be used to treat visceral pain.

M. Hepatic Disorders

TNFα has been implicated in the pathophysiology of a wide variety of hepatic disorders (see e.g., Colletti et al. (1990) *J Clin Invest.* 85:1936; Tiegs (1997) *Acta Gastroenterol Belg.* 60:176; Fernandez et al. (2000) *J Endotoxin Res.* 6:321). The invention provides multiple-variable dose methods for inhibiting TNFα activity in a subject suffering from such a hepatic disorder.

As used herein, the term "a hepatic disorder in which TNFα activity is detrimental" is intended to include diseases and other disorders of the liver or conditions associated with hepatocellular injury or a biliary tract disorders in which the presence of TNFα in a subject suffering from the disorder has been shown to be or is suspected of being either responsible for the pathophysiology of the disorder or a factor that contributes to a worsening of the disorder. Accordingly, a hepatic disorder in which TNFα activity is detrimental is a disorder in which inhibition of TNFα activity is expected to alleviate the symptoms and/or progression of the hepatic disorder. In one embodiment, hepatic disorders refers to a human liver disease or condition associated with hepatocellular injury or a biliary tract disorder excluding hepatitis, alcoholic hepatitis, and viral hepatitis.

Examples of animal models used for evaluating the therapeutic efficacy of an agent for treating a hepatic disorder using multiple-variable dose methods include the chimpanzee hepatitis C virus model (see Shimizu et al. (1990) *Proc Natl Acad Sci. USA* 87:6441). Examples of animal models used to study skin and nail disorder disorders include, for example, the severe combined immunodeficient (SCID) mouse model (psoriasis) and the Smith line (SL) chicken and depigmenting mouse (vitiligo) (see Nickoloff (2000) *Investig Dermatol Symp Proc.* 5:67; Austin et al. (1995) *Am J Pathol.* 146:1529; Lerner et al. (1986) *J Invest Dermatol.* 87:299).

Hepatic disorders include many diseases and disorders wherein the liver functions improperly or ceases to function. Hepatocellular injuries can include alcoholic cirrhosis, α1 antitrypsin deficiency, autoimmune cirrhosis, cryptogenic cirrhosis, fulminant hepatitis, hepatitis B and C, and steatohepatitis. Examples of biliary tract disorders include cystic fibrosis, primary biliary cirrhosis, sclerosing cholangitis and biliary obstruction (Wiesner (1996) "Current Indications, Contra Indications and Timing for Liver Transplantation" in *Transplantation of the Liver*, Saunders (publ.); Busuttil and Klintmalm (eds.) Chapter 6; Klein (1998) Partial Hypertension: The Role of Liver Transplantation, Musby (publ.) in *Current Surgical Therapy* 6.sup.th Ed. Cameron, J. (ed).

The term "hepatitis" refers to inflammation of the liver. Hepatitis can be caused by infections with various organisms, including bacteria, viruses (Hepatitis A, B, C, etc.), or parasites. Chemical toxins such as alcohol, drugs, or poisonous mushrooms can also damage the liver and cause it to become inflamed. A rare but extremely dangerous cause of hepatitis results from overdose of acetaminophen (Tylenol), which can be deadly. In addition, immune cells in the body may attack the liver and cause autoimmune hepatitis. Hepatitis may resolve quickly (acute hepatitis), or cause long-term disease (chronic hepatitis). In some instances, progressive liver damage or liver failure may result. The incidence and severity of hepatitis vary depending on many factors, including the cause of the liver damage and any underlying illnesses in a patient.

In one embodiment, the invention features multiple-variable methods for treating a hepatic disorder in which TNFα activity is detrimental, comprising administering to a subject an effective amount of a TNFα inhibitor in an induction dose and subsequently in a treatment dose, such that said disorder is treated. In one embodiment, the hepatic disorder is selected from the group consisting of hepatitis C virus, autoimmune hepatitis, fatty-liver disease, hepatitis B virus, hepatotoxicity, and non-alcoholic hepatitis, including non-alcoholic steatohepatitis (NASH). Examples of hepatic disorders are further described below.

1. Hepatitis C Virus (HCV)

Tumor necrosis factor has been implicated in the pathophysiology of the hepatitis C virus (see Gonzalez-Amaro. (1994) *J Exp Med* 179:841; Nelson et al. (1997) *Dig Dis Sci* 42:2487; Kallinowski et al. (1998) *Clin Exp Immunol.* 111:269). The term "hepatitis C virus" or "HCV" is used to describe the hepatitis virus which is the causative agent of non-A, non-B hepatitis. Hepatitis C virus causes an inflammation of the liver. HCV infection causes hepatitis C. Hepatitis C in the acute stage is, in general, milder than hepatitis B, but a greater proportion of such infections become chronic. HCV is a major cause of acute hepatitis and chronic liver disease, including cirrhosis and liver cancer. HCV is one of the viruses (A, B, C, D, and E), which together account for the vast majority of cases of viral hepatitis. It is an enveloped RNA virus in the flaviviridae family which appears to have a narrow host range. An important feature of the virus is the relative mutability of its genome, which in turn is probably related to the high propensity (80%) of inducing chronic infection. HCV is clustered into several distinct genotypes which may be important in determining the severity of the disease and the response to treatment. In one embodiment, the invention provides a multiple-variable dose method for treating HCV.

2. Autoimmune Hepatitis (AIH)

Tumor necrosis factor has been implicated in the pathophysiology of autoimmune hepatitis (see Cookson et al., (1999) *Hepatology* 30:851; Jazrawi et al., (2003) *Liver Transpl.* 9:377). As used herein, "autoimmune hepatitis" refers to a hepatic disorder characterized by inflammation of the liver caused by rogue immune cells that mistake the liver's normal cells for a foreign tissue or pathogen (disease-causing agent). Autoimmune hepatitis is often responsible for a progressive destruction of the hepatic parenchyma with a high mortality if left untreated (Johnson et al. (1993) *Hepatology,* 18:998). One of the characteristics of autoimmune hepatitis is the presence of circulating autoantibodies in almost 90% of patients' sera. Such antibodies can be used to identify subjects who have autoimmune hepatitis.

Clinical and serological differences between patients have lead to the classification of AIH into two types. Type 1 is characterized by the presence of anti-smooth muscle (SMA) and/or anti-nuclear antibodies (ANA) in patients' sera, while sera from Type II patients show anti-liver kidney microsomal antibodies type 1 (LKM1) (Homberg et al., (1987) *Hepatology,* 7:1333; Maggiore et al. (1993) *J. Pediatr. Gastroenterol Nutr.* 17:376). A serological marker, anti-liver cytosol type I antibodies (LC1), has been identified in 30% of patients with an AIH type II. In addition, LC1 proved to be the only serological marker in 10% of patients tested (Martini et al. (1988) *Hepatology,* 8:1662). In one embodiment, the multiple-variable dose method of the invention is used to treat AIH.

3. Fatty-Liver Disease

Tumor necrosis factor has been implicated in the pathophysiology of fatty-liver disease (see Valenti et al., (2002) Gastroenerology 122:274; Li et al., (2003) *Hepatology* 37:343). Fatty-liver disease refers to a disease wherein fat (hepatocytes) is excessively accumulated in the liver. Fatty liver disease is believed to be caused by supernutrition, hyperingestion of alcohol, diabetes and side effects due to administration of pharmaceuticals. Fatty liver disease can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. In one embodiment, the multiple-variable dose method of the invention is used to treat fatty liver disease.

4. Hepatitis B Virus (HBV)

Tumor necrosis factor has been implicated in the pathophysiology of hepatitis B virus (see Kasahara et al., (2003) *J Virol.* 77:2469; Wang (2003) *World J Gastroenterol.* 9:641; Biermer et al. (2003) *J Virol.* 77:4033). The term "hepatitis B virus" (HBV) is used to describe the virus (serum hepatitis virus) which produces viral hepatitis type B in humans. This is a viral disease with a long incubation period (about 50 to 160 days) in contrast to hepatitis A virus (infectious hepatitis virus) which has a short incubation period. The hepatitis B virus is usually transmitted by injection of infected blood or blood derivatives or merely by use of contaminated needles, lancets or other instruments. Clinically and pathologically, the disease is similar to viral hepatitis type A; however, there is no cross-protective immunity. Viral antigen (HBAg) is found in the serum after infection.

Hepatitis B virus infects humans at a very high rate. Most people who become infected with Hepatitis B get rid of the virus within 6 months, wherein a short infection is known as an "acute" case of Hepatitis B. It is estimated that at least about 300 million people are chronic carriers of HBV. Infection with the virus results in a range of clinical symptoms including minor flu-like symptoms to death. In one embodiment, the multiple-variable dose method of the invention is used to treat HBV infection.

5. Hepatotoxicity

Tumor necrosis factor has been implicated in the pathophysiology of hepatotoxicity (see Bruccoleri et al. (1997) *Hepatology* 25:133; Luster et al. (2000) *Ann NY Acad Sci.* 919:214; Simeonova et al. (2001) *Toxicol Appl Pharmacol.* 177:112). The term hepatotoxicity refers to liver damage caused by medications and other chemicals or drugs. The best indicator for identifying liver toxicity in a subject is the elevation of certain enzyme measurements in the blood, such as AST (aspartate aminotransferase), ALT (alanine aminotransferase), and GOT (glutamate oxalacetate transaminase).

Hepatotoxicity can cause permanent injury and death. Initial symptoms of hepatotoxicity can include acute gastrointestinal symptoms, e.g., severe diarrhea. The second phase of hepatotoxicity is characterized by abatement of symptoms. During this apparent subsidence, biochemical evidence of hepatic injury appears. Oliguria (decreased urine output) is usual during the second phase. The third phase, that of overt hepatic damage, becomes clinically apparent 3 to 5 days after ingestion of the chemical, with the appearance of jaundice. Renal failure may also occur. The symptoms of chemically-induced (drug-induced) hepatitis are similar to that of infectious hepatitis. In one embodiment, the multiple-variable dose method of the invention is used to treat hepatotoxicity.

6. Liver Failure (e.g. Chronic Liver Failure)

Tumor necrosis factor has been implicated in the pathophysiology of liver failure (e.g. chronic liver failure) (see Takenaka et al., (1998) *Dig Dis Sci.* 43:887; Nagaki et al. (1999) *J Hepatol.* 31:997; Streetz et al., (2000) *Gastroenterology.* 119:446. Liver failure, including chronic liver failure, usually develops over a period of years and is caused by a repeated insult to the liver (such as alcohol abuse or infection with hepatitis virus) which slowly damages the organ. Less commonly, liver failure is acute, and occurs over a period of days or weeks. Causes of acute liver failure include hepatitis virus infections, drugs, pregnancy, autoimmune disease, and sudden low blood flow to the liver. In one embodiment, the multiple-variable dose method of the invention is used to treat liver failure.

7. Non-Alcoholic Hepatitis, Including NASH

Tumor necrosis factor has been implicated in the pathophysiology of non-alcoholic hepatitis, including nonalcoholic steatohepatitis (see Crespo et al., (2001) *Hepatology.* 34:1158; Pessayre et al. (2002) 282(2):G193). The term "nonalcoholic steatohepatitis" or "NASH" refers to the development of histologic changes in the liver that are comparable to those induced by excessive alcohol intake, but in the absence of alcohol abuse. NASH is characterized by macrovesicular and/or microvesicular steatosis, lobular and portal inflammation, and occasionally Mallory bodies with fibrosis and cirrhosis. NASH is also commonly associated with hyperlipidemia, obesity, and type II diabetes mellitus.

Additional clinical conditions which characterize hepatic steatosis and inflammation include excessive fasting, jejunoileal bypass, total parental nutrition, chronic hepatitis C, Wilson's disease, and adverse drug effects such as those from corticosteroids, calcium channel blockers, high dose synthetic estrogens, methotrexate and amiodarone. Thus, the term "nonalcoholic steatohepatitis" can be used to describe those patients who exhibit these biopsy findings, coupled with the absence of (a) significant alcohol consumption, (b) previous surgery for weight loss, (c) history of drug use associated with steatohepatitis, (d) evidence of genetic liver disease or (e) chronic hepatitis C infection (see, e.g., Ludwig et al., (1980) *Mayo Clin. Proc.* 55:434; Powell et al. (1990) *Hepatol.* 11:74). In one embodiment, the multiple-variable dose method of the invention is used to treat NASH.

N. Skin and Nail Disorders

Tumor necrosis factor has been implicated in the pathophysiology of skin and nail disorders. In one embodiment, the multiple-variable dose method of the invention comprising administering an induction dose of a TNFα antibody followed by a subsequent treatment dose, can be used to treat skin and nail disorders. The term "skin disorder" or "skin disease" as used interchangeably herein, refers to abnormalities, other than injury wounds, of the skin which have induced a state of inflammation. In one embodiment, the skin disorder of the invention is an inflammatory skin disorder, wherein the skin is characterized by capillary dilatation, leukocytic infiltration, redness, heat, and/or pain. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo. As used herein, the term "skin and nail disorder in which TNFα activity is detrimental" is intended to include skin and/or nail disorders and other disorders in which the presence of TNFα in a subject suffering from the disorder has been shown to be or is suspected of being either responsible for the pathophysiology of the disorder or a factor that contributes to a worsening of the disorder, e.g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors of the invention in the treatment of specific skin and nail disorders is discussed further below. In certain embodiments, the treatment method of the invention is performed in combination with another therapeutic agent, as described below in Section IV. In one embodiment, the multiple-variable dose method of the invention comprising administering a TNFα antibody in combination with another therapeutic agent is used for the treatment of psoriasis and the treatment of psoriasis associated with arthritis.

1. Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1:264). The term "psoriasis" as used herein, refers to skin disorders associated with epidermal hyperplasia. Example of psoriasis include, but are not limited to, chronic plaque psoriasis, guttate psoriasis, inverse psoriasis, pustular psoriasis, psoriasis vulgaris, and erythrodermic psoriasis. Psoriasis can also be associated with other inflammatory disorders, including inflammatory bowel disease (IBD) and rheumatoid arthritis (RA).

Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease. Approximately one third of subjects with psoriasis also have psoriatic arthritis (PsA) which, as described above, causes stiffness, swelling of the joints, pain, and reduced range of motion (Greaves et al. (1995) *N. Eng. J. Med.* 332:581).

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFα inhibitor of the invention is administered in combination with or the presence of one of these common treatments. Additional therapeutic agents which can also be combined with the TNFα inhibitor of the invention for treatment of psoriasis are described in more detail in Section IV.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

Improvements in psoriasis in a subject can be monitored by the subject's Psoriasis Area and Severity Index Score (PASI). The method for determining the PASI has been described in Fredriksson and Pettersson (1978) *Dermatologica* 157:238 and Marks et al. (1989) *Arch Dermatol* 125:235. Briefly, the index is based on evaluation of four anatomic sites, including the head, upper extremities, trunk, and lower extremities, for erythema, induration, and desquamation using a 5 point scale (0=no symptoms; 1=slight; 2=moderate; 3=marked; 4=very marked). Based on the extent of lesions in a given anatomic site, the area affected is assigned a numerical value (0=0; 1=<10%; 2=10-29%; 3=30-49%; 4=50-69%; 5=70=89%; 6=90-100%). The PASI score is then calculated, wherein the possible range of PASI score is 0.0 to 72.0 with the highest score representing complete erythroderma of the severest degree.

In one embodiment of the invention, a TNFα inhibitor is used in multiple-variable dose treatment for psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In another embodiment, a TNFα inhibitor, such as D2E7, is used in a multiple variable dose regimen to treat subjects who have psoriasis in combination with PsA. Specific types of psoriasis included in the treatment methods of the invention are described in detail below:

a. Chronic Plaque Psoriasis

Tumor necrosis factor has been implicated in the pathophysiology of chronic plaque psoriasis (Asadullah et al. (1999) *Br J Dermatol.* 141:94). Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent.

Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

d. Pustular Psoriasis

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders which can be treated with the TNFα antibody of the invention include erythrodermic psoriasis, vulgaris, psoriasis associated with IBD, and psoriasis associated with arthritis, including rheumatoid arthritis.

2. Pemphigus Vulgaris

Pemphigus vulgaris is a serious autoimmune systemic dermatologic disease that often affects the oral mucous membrane and skin. The pathogenesis of pemphigus vulgaris is thought to be an autoimmune process that is directed at skin and oral mucous membrane desmosomes. Consequentially, cells do not adhere to each other. The disorder manifests as large fluid-filled, rupture-prone bullae, and has a distinctive histologic appearance. Anti-inflammatory agents are the only effective therapy for this disease which has a high mortality rate. Complications that arise in patients suffering from pemphigus vulgaris are intractable pain, interference with nutrition and fluid loss, and infections.

3. Atopic Dermatitis/Eczema

Atopic dermatitis (also referred to as eczema) is a chronic skin disorder categorized by scaly and itching plaques. People with eczema often have a family history of allergic conditions like asthma, hay fever, or eczema. Atopic dermatitis is a hypersensitivity reaction (similar to an allergy) which occurs in the skin, causing chronic inflammation. The inflammation causes the skin to become itchy and scaly. Chronic irritation and scratching can cause the skin to thicken and become leathery-textured. Exposure to environmental irritants can worsen symptoms, as can dryness of the skin, exposure to water, temperature changes, and stress.

Subjects with atopic dermatitis can be identified by certain symptoms, which often include intense itching, blisters with oozing and crusting, skin redness or inflammation around the blisters, rash, dry, leathery skin areas, raw areas of the skin from scratching, and ear discharges/bleeding.

4. Sarcoidosis

Sarcoidosis is a disease in which granulomatous inflammation occurs in the lymph nodes, lungs, liver, eyes, skin, and/or other tissues. Sarcoidosis includes cutaneous sarcoidosis (sarcoidosis of the skin) and nodular sarcoidosis (sarcoidosis of the lymph nodes). Patients with sarcoidosis can be identified by the symptoms, which often include general discomfort, uneasiness, or an ill feeling; fever; skin lesions.

5. Erythema Nodosum

Erythema nodosum refers to an inflammatory disorder that is characterized by tender, red nodules under the skin, typically on the anterior lower legs. Lesions associated with erythema nodosum often begin as flat, but firm, hot red painful lumps (approximately an inch across). Within a few days the lesions may become purplish, and then over several weeks fade to a brownish flat patch.

In some instances, erythema nodosum may be associated with infections including, streptococcus, coccidioidomycosis, tuberculosis, hepatitis B, syphilis, cat scratch disease, tularemia, yersinia, leptospirosis psittacosis, histoplasmosis, mononucleosis (EBV). In other instances, erythema nodosum may be associated with sensitivity to certain medications including, oral contraceptives, penicillin, sulfonamides, sulfones, barbiturates, hydantoin, phenacetin, salicylates, iodides, and progestin. Erythema nodosum is often associated with other disorders including, leukemia, sarcoidosis, rheumatic fever, and ulcerative colitis.

Symptoms of erythema nodosum usually present themselves on the shins, but lesions may also occur on other areas of the body, including the buttocks, calves, ankles, thighs and upper extremities. Other symptoms in subjects with erythema nodosum can include fever and malaise.

6. Hidradenitis Suppurative

Hidradenitis suppurativa refers to a skin disorder in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

7. Lichen Planus

Tumor necrosis factor has been implicated in the pathophysiology of lichen planus (Sklavounou et al. (2000) *J Oral Pathol Med.* 29:370). Lichen planus refers to a disorder of the skin and the mucous membranes resulting in inflammation, itching, and distinctive skin lesions. Lichen planus may be associated with hepatitis C or certain medications.

8. Sweet's Syndrome

Inflammatory cytokines, including tumor necrosis factor, have been implicated in the pathophysiology of Sweet's syndrome (Reuss-Borst et al. (1993) *Br J Haematol.* 84:356). Sweet's syndrome, which was described by R. D. Sweet in 1964, is characterized by the sudden onset of fever, leukocytosis, and cutaneous eruption. The eruption consists of tender, erythematosus, well-demarcated papules and plaques which show dense neutrophilic infiltrates microscopically. The lesions may appear anywhere, but favor the upper body including the face. The individual lesions are often described as pseudovesicular or pseudopustular, but may be frankly pustular, bullous, or ulcerative. Oral and eye involvement (conjunctivitis or episcleritis) have also been frequently reported in patients with Sweet's syndrome. Leukemia has also been associated with Sweet's syndrome.

9. Vitiligo

Vitiligo refers to a skin condition in which there is loss of pigment from areas of skin resulting in irregular white patches with normal skin texture. Lesions characteristic of vitiligo appear as flat depigmented areas. The edges of the lesions are sharply defined but irregular. Frequently affected areas in subjects with vitiligo include the face, elbows and knees, hands and feet, and genitalia.

10. Scleroderma

Tumor necrosis factor has been implicated in the pathophysiology of scleroderma (Tutuncu et al. (2002) *Clin Exp Rheumatol*. 20(6 Suppl 28):S146; Mackiewicz et al. (2003) *Clin Exp Rheumatol*. 21:41; Murota et al. (2003) *Arthritis Rheum*. 48:1117). Scleroderma refers to a diffuse connective tissue disease characterized by changes in the skin, blood vessels, skeletal muscles, and internal organs. Scleroderma is also referred to as CREST syndrome or progressive systemic sclerosis, and usually affects people between the ages 30-50. Women are affected more often than men.

The cause of scleroderma is unknown. The disease may produce local or systemic symptoms. The course and severity of the disease varies widely in those affected. Excess collagen deposits in the skin and other organs produce the symptoms. Damage to small blood vessels within the skin and affected organs also occurs. In the skin, ulceration, calcification, and changes in pigmentation may occur. Systemic features may include fibrosis and degeneration of the heart, lungs, kidneys and gastrointestinal tract.

Patients suffering from scleroderma exhibit certain clinical features, including, blanching, blueness, or redness of fingers and toes in response to heat and cold (Raynaud's phenomenon), pain, stiffness, and swelling of fingers and joints, skin thickening and shiny hands and forearm, esophageal reflux or heartburn, difficulty swallowing, and shortness of breath. Other clinical symptoms used to diagnose scleroderma include, an elevated erythrocyte sedimentation rate (ESR), an elevated rheumatoid factor (RF), a positive antinuclear antibody test, urinalysis that shows protein and microscopic blood, a chest X-ray that may show fibrosis, and pulmonary function studies that show restrictive lung disease.

11. Nail Disorders

Nail disorders include any abnormality of the nail. The term "nail disorder" or "nail disease" as used herein, refers to conditions wherein the fingernails or toenails to abnormal color, shape, texture, or thickness. Specific nail disorders include, but are not limited to, pitting, koilonychia, Beau's lines, spoon nails, onycholysis, yellow nails, pterygium (seen in lichen planus), and leukonychia. Pitting is characterised by the presence of small depressions on the nail surface. Ridges or linear elevations can develop along the nail occurring in a "lengthwise" or "crosswise" direction. Beau's lines are linear depressions that occur "crosswise" (transverse) in the fingernail. Leukonychia describes white streaks or spots on the nails. Koilonychia is an abnormal shape of the fingernail where the nail has raised ridges and is thin and concave Koilonychia is often associated with iron deficiency.

Nail disorders which can be treated with the TNFα antibody of the invention also include psoriatic nails. Psoriatic nails include changes in nails which are attributable to psoriasis. In some instances psoriasis may occur only in the nails and nowhere else on the body. Psoriatic changes in nails range from mild to severe, generally reflecting the extent of psoriatic involvement of the nail plate, nail matrix, i.e., tissue from which the nail grows, nail bed, i.e., tissue under the nail, and skin at the base of the nail. Damage to the nail bed by the pustular type of psoriasis can result in loss of the nail. Nail changes in psoriasis fall into general categories that may occur singly or all together. In one category of psoriatic nails, the nail plate is deeply pitted, probably due to defects in nail growth caused by psoriasis. In another category, the nail has a yellow to yellow-pink discoloration, probably due to psoriatic involvement of the nail bed. A third subtype of psoriatic nails are characterized by white areas which appear under the nail plate. The white areas are actually air bubbles marking spots where the nail plate is becoming detached from the nail bed. There may also be reddened skin around the nail. A fourth category is evidenced by the nail plate crumbling in yellowish patches, i.e., onychodystrophy, probably due to psoriatic involvement in the nail matrix. A fifth category is characterized by the loss of the nail in its entirety due to psoriatic involvement of the nail matrix and nail bed.

The multiple-variable dose method of treatment of the invention can also be used to treat nail disorders often associated with lichen planus. Nails in subjects with lichen planus often show thinning and surface roughness of the nail plate with longitudinal ridges or pterygium.

The multiple-variable dose method of treatment of the invention can be used to treat nail disorders, such as those described herein. Often nail disorders are associated with skin disorders. In one embodiment, the invention includes a multiple-variable dose method of treatment for nail disorders using a TNFα antibody. In another embodiment, the nail disorder is associated with another disorder, including a skin disorder such as psoriasis. In another embodiment, the disorder associated with a nail disorder is arthritis, including psoriatic arthritis.

12. Other Skin and Nail Disorders

The multiple-variable dose method of treatment of the invention can be used to treat other skin and nail disorders, such as chronic actinic dermatitis, bullous pemphigoid, and alopecia areata. Chronic actinic dermatitis (CAD) is also referred to as photosensitivity dermatitis/actinic reticuloid syndrome (PD/AR). CAD is a condition in which the skin becomes inflamed, particularly in areas that have been exposed to sunlight or artificial light. Commonly, CAD patients have allergies to certain substances that come into contact with their skin, particularly various flowers, woods, perfumes, sunscreens and rubber compounds. Bullous pemphigoid refers to a skin disorder characterized by the formation of large blisters on the trunk and extremities. Alopecia areata refers to hair loss characterized by round patches of complete baldness in the scalp or beard.

O. Vasculitides

TNFα has been implicated in the pathophysiology of a variety of vasculitides, (see e.g., Deguchi et al. (1989) Lancet. 2:745). In one embodiment, the invention provides a multiple-variable dose method for inhibiting TNFα activity in a subject suffering from a vasculitis in which TNFα activity is detrimental.

The term "vasculitis" or "vasculitides" as used interchangeably herein, refers to a group of disorders which are characterized by the inflammation of blood vessels. Blood vessels of all sizes may be affected, from the largest vessel in the body (the aorta) to the smallest blood vessels in the skin (capillaries). The size of blood vessel affected varies according to the specific type of vasculitis. As used herein, the term "a vasculitis in which TNFα activity is detrimental" is intended to include vasculitis in which the presence of TNFα in a subject suffering from the disorder has been shown to be or is suspected of being either responsible for the pathophysiology of the disorder or a factor that contributes to a worsening of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above.

There are numerous examples of vasculitides in which TNFα activity is detrimental, including Behcet's disease. The use of the antibodies, antibody portions, and other TNFα inhibitors for multiple-variable dose treatment of the invention of specific vasculitides is discussed further below. In certain embodiments, the antibody, antibody portion, or other TNFα inhibitor of the invention is administered to the subject in combination with another therapeutic agent, as described below The multiple-variable dose regimen of the invention can be used to treat vasculitis in which TNFα activity is detrimental, wherein inhibition of TNFα activity is expected to alleviate the symptoms and/or progression of the vasculitis or to prevent the vasculitis. Subjects suffering from or at risk of developing vasculitis can be identified through clinical symptoms and tests. For example, subjects with vasculitides often develop antibodies to certain proteins in the cytoplasm of neutrophils, antineutrophil cytoplasmic antibodies (ANCA). Thus, in some instances, vasculitides may be evidenced by tests (e.g., ELISA), which measure ANCA presence.

Vasculitis and its consequences may be the sole manifestation of disease or it may be a secondary component of another primary disease. Vasculitis may be confined to a single organ or it may simultaneously affect several organs. and depending on the syndrome, arteries and veins of all sizes can be affected. Vasculitis can affect any organ in the body.

In vasculitis, the vessel lumen is usually compromised, which is associated with ischemia of the tissues supplied by the involved vessel. The broad range of disorders that may result from this process is due to the fact that any type, size and location of vessel (e.g., artery, vein, arteriole, venule, capillary) can be involved. Vasculitides are generally classified according to the size of the affected vessels, as described below. It should be noted that some small and large vessel vasculitides may involve medium-sized arteries; but large and medium-sized vessel vasculitides do not involve vessels smaller than arteries. Large vessel disease includes, but is not limited to, giant cell arteritis, also known as temporal arteritis or cranial arteritis, polymyalgia rheumatica, and Takayasu's disease or arteritis, which is also known as aortic arch syndrome, young female arteritis and Pulseless disease. Medium vessel disease includes, but is not limited to, classic polyarteritis nodosa and Kawasaki's disease, also known as mucocutaneous lymph node syndrome. Non-limiting examples of small vessel disease are Behcet's Syndrome, Wegner's granulomatosis, microscopic polyangitis, hypersensitivity vasculitis, also known as cutaneous vasculitis, small vessel vasculitis, Henoch-Schonlein purpura, allergic granulamotosis and vasculitis, also known as Churg Strauss syndrome. Other vasculitides include, but are not limited to, isolated central nervous system vasculitis, and thromboangitis obliterans, also known as Buerger's disease. Classic Polyarteritis nodosa (PAN), microscopic PAN, and allergic granulamotosis are also often grouped together and are called the systemic necrotizing vasculitides. A further description of vasculitis is described below:

1. Large Vessel Vasculitis

In one embodiment, the TNFα antibody of the invention is used to treat subjects who have large vessel vasculitis. The term "large vessel(s)" as used herein, refers to the aorta and the largest branches directed toward major body regions. Large vessels include, for example, the aorta, and its branches and corresponding veins, e.g., the subclavian artery; the brachiocephalic artery; the common carotid artery; the innonimate vein; internal and external jugular veins; the pulmonary arteries and veins; the venae cavae; the renal arteries and veins; the femoral arteries and veins; and the carotid arteries. Examples of large vessel vasculitides are described below.

a. Giant Cell Arteritis (GCA)

Tumor necrosis factor has been implicated in the pathophysiology of giant cell arteritis (Sneller (2002) *Cleve. Clin. J. Med.* 69:SII40; Schett et al. (2002) *Ann. Rheum. Dis.* 61:463). Giant cell arteritis (GCA), refers to a vasculitis involving inflammation and damage to blood vessels, particularly the large or medium arteries that branch from the external carotid artery of the neck. GCA is also referred to as temporal arteritis or cranial arteritis, and is the most common primary vasculitis in the elderly. It almost exclusively affects individuals over 50 years of age, however, there are well-documented cases of patients 40 years and younger. GCA usually affects extracranial arteries. GCA can affect the branches of the carotid arteries, including the temporal artery. GCA is also a systemic disease which can involve arteries in multiple locations.

Histopathologically, GCA is a panarteritis with inflammatory mononuclear cell infiltrates within the vessel wall with frequent Langhans type giant cell formation. There is proliferation of the intima, granulomatous inflammation and fragmentation of the internal elastic lamina. The pathological findings in organs is the result of ischemia related to the involved vessels.

Patients suffering from GCA exhibit certain clinical symptoms, including fever, headache, anemia and high erythrocyte sedimentation rate (ESR). Other typical indications of GCA include jaw or tongue claudication, scalp tenderness, constitutional symptoms, pale optic disc edema (particularly 'chalky white' disc edema), and vision disturbances. The diagnosis is confirmed by temporal artery biopsy.

b. Polymyalgia Rheumatica

Tumor necrosis factor has been implicated in the pathophysiology of polymyalgia rheumatica (Straub et al. (2002) *Rheumatology* (Oxford) 41:423; Uddhammar et al. (1998) *Br. J. Rheumatol.* 37:766). Polymyalgia rheumatica refers to a rheumatic disorder that is associated with moderate to severe muscle pain and stiffness in the neck, shoulder, and hip, most noticeable in the morning. IL-6 and IL-1β expression has also been detected in a majority of the circulating monocytes in patients with the polymyalgia rheumatica. Polymyalgia rheumatica may occur independently, or it may coexist with or precede GCA, which is an inflammation of blood vessels.

c. Takayasu's Arteritis

Tumor necrosis factor has been implicated in the pathophysiology of Takayasu's arteritis (Kobayashi and Numano (2002) *Intern. Med.* 41:44; Fraga and Medina (2002) *Curr. Rheumatol. Rep.* 4:30). Takayasu's arteritis refers to a vasculitis characterized by an inflammation of the aorta and its major branches. Takayasu's arteritis (also known as Aortic arch syndrome, young female arteritis and Pulseless disease) affects the thoracic and abdominal aorta and its main branches or the pulmonary arteries. Fibrotic thickening of the aortic wall and its branches (e.g., carotid, inominate, and subclavian arteries) can lead to reduction of lumen size of vessels that arise from the aortic arch. This condition also typically affects the renal arteries.

Takayasu's arteritis primarily affects young women, usually aged 20-40 years old, particularly of Asian descent, and may be manifested by malaise, arthralgias and the gradual onset of extremity claudication. Most patients have asymmetrically reduced pulses, usually along with a blood pressure differential in the arms. Coronary and/or renal artery stenosis may occur.

The clinical features of Takayasu's arteritis may be divided into the features of the early inflammatory disease and the features of the later disease. The clinical features of the early inflammatory stage of Takayasu's disease are: malaise, low grade fever, weight loss, myalgia, arthralgia, and erythema multiforme. Later stages of Takayasu's disease are characterized by fibrotic stenosis of arteries and thrombosis. The main resulting clinical features are ischaemic phenomena, e.g. weak and asymmetrical arterial pulses, blood pressure discrepancy between the arms, visual disturbance, e.g. scotomata and hemianopia, other neurological features including vertigo and syncope, hemiparesis or stroke. The clinical features result from ischaemia due to arterial stenosis and thrombosis.

2. Medium Vessel Disease

In one embodiment, the TNFα antibody of the invention is used to treat subjects who have medium vessel vasculitis. The term "medium vessel(s)" is used to refer to those blood vessels which are the main visceral arteries. Examples of medium vessels include the mesenteric arteries and veins, the iliac arteries and veins, and the maxillary arteries and veins. Examples of medium vessel vasculitides are described below.

a. Polyarteritis Nodosa

Tumor necrosis factor has been implicated in the pathophysiology of polyarteritis nodosa (DiGirolamo et al. (1997) *J. Leukoc. Biol.* 61:667). Polyarteritis nodosa, or periarteritis nodosa refers to vasculitis which is a serious blood vessel disease in which small and medium-sized arteries become swollen and damaged because they are attacked by rogue immune cells. Polyarteritis nodosa usually affects adults more frequently than children. It damages the tissues supplied by the affected arteries because they don't receive enough oxygen and nourishment without a proper blood supply.

Symptoms which are exhibited in patients with polyarteritis nodosa generally result from damage to affected organs, often the skin, heart, kidneys, and nervous system. Generalized symptoms of polyarteritis nodosa include fever, fatigue, weakness, loss of appetite, and weight loss. Muscle aches (myalgia) and joint aches (arthralgia) are common. The skin of subjects with polyarteritis nodosa may also show rashes, swelling, ulcers, and lumps (nodular lesions).

Classic PAN (polyarteritis nodosa) is a systemic arteritis of small to medium muscular arteritis in which involvement of renal and visceral arteries is common. Abdominal vessels have aneurysms or occlusions in 50% of PAN patients. Classic PAN does not involve the pulmonary arteries although the bronchial vessels may be involved. Granulomas, significant eosinophilia and an allergic diathesis are not part of the syndrome. Although any organ system may be involved, the most common manifestations include peripheral neuropathy, mononeuritis multiplex, intestinal ischemia, renal ischemia, testicular pain and livedo reticularis.

b. Kawasaki's Disease

Tumor necrosis factor has been implicated in the pathophysiology of Kawasaki's disease (Sundel (2002) *Curr. Rheumatol. Rep.* 4:474; Gedalia (2002) *Curr. Rheumatol. Rep.* 4:25). Although the cause of Kawasaki's disease is unknown, it is associated with acute inflammation of the coronary arteries, suggesting that the tissue damage associated with this disease may be mediated by proinflammatory agents such as TNFα. Kawasaki's disease refers to a vasculitis that affects the mucus membranes, lymph nodes, lining of the blood vessels, and the heart. Kawasaki's disease is also often referred to as mucocutaneous lymph node syndrome, mucocutaneous lymph node disease, and infantile polyarteritis. Subjects afflicted with Kawasaki's disease develop vasculitis often involving the coronary arteries which can lead to myocarditis and pericarditis. Often as the acute inflammation diminishes, the coronary arteries may develop aneurysm, thrombosis, and lead to myocardial infarction.

Kawasaki's disease is a febrile systemic vasculitis associated with edema in the palms and the soles of the feet, with enlargement of cervical lymph nodes, cracked lips and "strawberry tongue". Although the inflammatory response is found in vessels throughout the body, the most common site of end-organ damage is the coronary arteries. Kawasaki's Disease predominantly affects children under the age of 5. The highest incidence is in Japan but is becoming increasingly recognized in the West and is now the leading cause of acquired heart disease in US children. The most serious complication of Kawasaki disease is coronary arteritis and aneurysm formation that occurs in a third of untreated patients.

3. Small Vessel Disease

In one embodiment, the TNFα antibody of the invention is used to treat subjects who have small vessel vasculitis. The term "small vessel(s)" is used to refer to arterioles, venules and capillaries. Arterioles are arteries that contain only 1 or 2 layers of sooth muscle cells and are terminal to and continuous with the capillary network. Venules carry blood from the capillary network to veins and capillaries connect arterioles and venules. Examples of small vessel vasculitides are described below.

a. Behcet's Disease

Tumor necrosis factor has been implicated in the pathophysiology of Behcet's disease (Sfikakis (2002) *Ann. Rheum. Dis.* 61:ii51-3; Dogan and Farah (2002) *Oftalmologia.* 52:23). Behcet's disease is a chronic disorder that involves inflammation of blood vessels throughout the body. Behcet's disease may also cause various types of skin lesions, arthritis, bowel inflammation, and meningitis (inflammation of the membranes of the brain and spinal cord). As a result of Behcet's disease, the subject with the disorder may have inflammation in tissues and organs throughout the body, including the gastrointestinal tract, central nervous system, vascular system, lungs, and kidneys. Behcet's disease is three times more common in males than females and is more common in the eastern Mediterranean and Japan.

Subjects who have Behcet's disease may show clinical symptoms including recurrent oral ulcers (resembling canker sores), recurrent genital ulcers, and eye inflammation. Serum levels of TNFα, IL-8, IL-1, IL-6 INF-γ and IL-12 are elevated in Behcet's patients, and the production of these factors has been shown to be elevated in the monocytes of Behcet's patients (see, e.g., *Inflammatory Disease of Blood Vessels* (2001) Marcel Dekker, Inc., eds. G. S. Hoffman and C. M. Weyand, p. 473).

b. Wegener's Granulomatosis

Tumor necrosis factor has been implicated in the pathophysiology of Wegener's granulomatosis (Marquez et al. (2003) *Curr. Rheumatol.* Rep. 5:128; Harman and Margo (1998) *Surv. Ophthalmol.* 42:458). Wegener's granulomatosis refers to a vasculitis that causes inflammation of blood vessels in the upper respiratory tract (nose, sinuses, ears), lungs, and kidneys. Wegener's granulomatosis is also referred to as midline granulomatosis. Wegener's granulomatosis includes a granulomatous inflammation involving the respiratory tract, and necrotizing vasculitis affecting small to medium-sized vessels. Subjects who have Wegener's granulomatosis often also have arthritis (joint inflammation). Glomerulonephritis may also be present in affected subjects, but virtually any organ may be involved.

Patients affected with Wegener's granulomatosis typically show clinical symptoms comprising recurrent sinusitis or epistaxis, mucosal ulcerations, otitis media, cough, hemoptysis and dyspnea. The first symptoms of Wegener's granulomatosis frequently include upper respiratory tract symptoms, joint pains, weakness, and tiredness.

c. Churg-Strauss Syndrome

Tumor necrosis factor has been implicated in the pathophysiology of Churg-Strauss syndrome (Gross (2002) *Curr. Opin. Rheumatol.* 14:11; Churg (2001) *Mod. Pathol.* 14:1284). Churg-Strauss syndrome refers to a vasculitis that is systemic and shows early manifestation signs of asthma and eosinophilia. Churg-Strauss syndrome is also referred to as allergic granulomatosis and angiitis, and occurs in the setting of allergic rhinitis, asthma and eosinophilia. Sinusitis and pulmonary infiltrates also occur in Churg-Strauss syndrome, primarily affecting the lung and heart. Peripheral neuropathy, coronary arteritis and gastrointestinal involvement are common.

Patients afflicted with Churg-Strauss syndrome can be diagnosed according to criteria established by the American College of Rheumatology (ACR). These criteria were intended to distinguish CSS from other forms of vasculitis. Not all patients meet every criterion. Some, in fact, may have only 2 or 3 criteria, yet they are still classified as Churg-Strauss syndrome. The ACR selected 6 disease features (criteria) as being those that best distinguished Churg-Strauss syndrome from other vasculitides. These criteria include: 1) asthma; 2) eosinophilia [>10% on differential WBC count]; 3) mononeuropathy; 4) transient pulmonary infiltrates on chest X-rays; 5) paranasal sinus abnormalities; and 6) biopsy containing a blood vessel with extravascular eosinophils.

P. Other TNFα-Related Disorders

In one embodiment, the invention features a multiple-variable dose method for treating a TNFα-related disorder in which TNFα activity is detrimental, comprising administering to a subject an induction dose of a TNFα inhibitor and a subsequent treatment dose, such that said TNFα-related disorder is treated. Examples of TNFα-related disorders in which TNFα activity is detrimental, are discussed further below.

1. Juvenile Arthritis

Tumor necrosis factor has been implicated in the pathophysiology of juvenile arthritis, including juvenile rheumatoid arthritis (Grom et al. (1996) *Arthritis Rheum.* 39:1703; Mangge et al. (1995) *Arthritis Rheum.* 8:211). In one embodiment, the TNFα antibody of the invention is used to treat juvenile rheumatoid arthritis.

The term "juvenile rheumatoid arthritis" or "JRA" as used herein refers to a chronic, inflammatory disease which occurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test. These classifications help the physician determine how the disease will progress and whether the internal organs or skin is affected. The classifications of JRA include the following a. Pauciarticular JRA, wherein the patient has four or fewer joints are affected. Pauciarticular is the most common form of JRA, and typically affects large joints, such as the knees.

b. Polyarticular HRA, wherein five or more joints are affected. The small joints, such as those in the hands and feet, are most commonly involved, but the disease may also affect large joints.

c. Systemic JRA is characterized by joint swelling, fever, a light skin rash, and may also affect internal organs such as the heart, liver, spleen, and lymph nodes. Systemic JRA is also referred to as it Still's disease. A small percentage of these children develop arthritis in many joints and can have severe arthritis that continues into adulthood.

2. Endometriosis

Tumor necrosis factor has been implicated in the pathophysiology of endometriosis, as women with endometriosis have elevated peritoneal levels of TNF (Eisermann et al. (1988) *Fertil Steril* 50:573; Halme (1989) *Am J Obstet Gynecol* 161:1718; Mori et al. (1991) *Am J Reprod Immunol* 26:62; Taketani et al. (1992) *Am J Obstet Gynecol* 167:265; Overton et al. (1996) *Hum Reprod* 1996; 11:380). In one embodiment, the TNFα antibody of the invention is used to treat endometriosis. The term "endometriosis" as used herein refers to a condition in which the tissue that normally lines the uterus (endometrium) grows in other areas of the body, causing pain, irregular bleeding, and frequently infertility.

3. Prostatitis

Tumor necrosis factor has been implicated in the pathophysiology of prostatitis, as men with chronic prostatitis and chronic pelvic pain have significantly higher levels of TNF and IL-1 in semen compared to controls (Alexander et al. (1998) *Urology* 52:744; Nadler et al. (2000) *J Urol* 164:214; Orhan et al. (2001) *Int J Urol* 8:495) Furthermore, in a rat model of prostatitis TNF levels were also increased in comparison to controls (Asakawa et al. (2001) *Hinyokika Kiyo* 47:459; Harris et al. (2000) *Prostate* 44:25). In one embodiment, the TNFα antibody of the invention is used to treat prostatitis.

The term "prostatitis" as used herein refers to an inflammation of the prostate. Prostatitis is also referred to as pelvic pain syndrome. Prostatitis manifests itself in a variety of forms, including nonbacterial prostatitis, acute prostatitis, bacterial prostatitis, and acute prostatitis. Acute prostatitis refers to an inflammation of the prostate gland that develops suddenly. Acute prostatitis is usually caused by a bacterial infection of the prostate gland. Chronic prostatitis is an inflammation of the prostate gland that develops gradually, continues for a prolonged period, and typically has subtle symptoms. Chronic prostatitis is also usually caused by a bacterial infection 4. Choroidal Neovascularization Tumor necrosis factor has been implicated in the pathophysiology of choroidal neovascularization. For example, in surgically excised choroidal neovascular membranes, neovascular vessels stained positive for both TNF and IL-1 (Oh H et al. (1999) *Invest Ophthalmol Vis Sci* 40:1891). In one embodiment, the TNFα antibody of the invention is used to treat choroidal neovascularization. The term "choroidal neovascularization" as used herein refers to the growth of new blood vessels that originate from the choroid through a break in the Bruch membrane into the sub-retinal pigment epithelium (sub-RPE) or subretinal space. Choroidal neovascularization (CNV) is a major cause of visual loss in patients with the condition.

5. Sciatica

Tumor necrosis factor has been implicated in the pathophysiology of sciatica (Ozaktay et al. (2002) *Eur Spine J.* 11:467; Brisby et al. (2002) *Eur Spine J.* 11:62). In one embodiment, the TNFα antibody of the invention is used to treat sciatica. The term "sciatica" as used herein refers to a condition involving impaired movement and/or sensation in the leg, caused by damage to the sciatic nerve. Sciatica is also commonly referred to as neuropathy of the sciatic nerve and sciatic nerve dysfunction. Sciatica is a form of peripheral neuropathy. It occurs when there is damage to the sciatic nerve, located in the back of the leg. The sciatic nerve controls the muscles of the back of the knee and lower leg and provides sensation to the back of the thigh, part of the lower leg and the sole of the foot. Sciatica can be indicative of another disorder, including a lumbar herniated disc, spinal stenosis, degenerative disc disease, isthmic spondyloisthesis and piniformis syndrome.

6. Sjogren's Syndrome

Tumor necrosis factor has been implicated in the pathophysiology of Sjogren's syndrome (Koski et al. (2001) *Clin Exp Rheumatol.* 19:131). In one embodiment, the TNFα antibody of the invention is used to treat Sjogren's syndrome. The term "Sjogren's syndrome" as used herein refers to a systemic inflammatory disorder characterized by dry mouth, decreased tearing, and other dry mucous membranes, and is often associated with autoimmune rheumatic disorders, such as rheumatoid arthritis. Dryness of the eyes and mouth are the most common symptoms of this syndrome. The symptoms may occur alone, or with symptoms associated with rheumatoid arthritis or other connective tissue diseases. There may be an associated enlargement of the salivary glands. Other organs may become affected. The syndrome may be associated with rheumatoid arthritis, systemic lupus erythematosus, scleroderma, polymyositis, and other diseases.

7. Uveitis

Tumor necrosis factor has been implicated in the pathophysiology of uveitis (Wakefield and Lloyd (1992) *Cytokine* 4:1; Woon et al. (1998) *Curr Eye Res.* 17:955). In one embodiment, the TNFα antibody of the invention is used to treat uveitis. The term "uveitis" as used herein refers to an inflammation of the uvea, which is the layer between the sclera and the retina, which includes the iris, ciliary body, and the choroid. Uveitis is also commonly referred to as iritis, pars planitis, chroiditis, chorioretinitis, anterior uveitis, and posterior uveitis. The most common form of uveitis is anterior uveitis, which involves inflammation in the front part of the eye, which is usually isolated to the iris. This condition is often called iritis. In one embodiment, the term uveitis refers to an inflammation of the uvea which excludes inflammation associated with an autoimmune disease, i.e., excludes autoimmune uveitis.

8. Wet Macular Degeneration

Tumor necrosis factor has been implicated in the pathophysiology of wet macular degeneration. In one embodiment, the TNFα antibody of the invention is used to treat wet macular degeneration. The term "wet macular degeneration" as used herein refers to a disorder that affects the macula (the central part of the retina of the eye) and causes decreased visual acuity and possible loss of central vision. Patients with wet macular degeneration develop new blood vessels under the retina, which causes hemorrhage, swelling, and scar tissue.

9. Osteoporosis

Tumor necrosis factor has been implicated in the pathophysiology of osteoporosis, (Tsutsumimoto et al. (1999) *J Bone Miner Res.* 14:1751). Osteoporosis is used to refer to a disorder characterized by the progressive loss of bone density and thinning of bone tissue. Osteoporosis occurs when the body fails to form enough new bone, or when too much old bone is reabsorbed by the body, or both. The TNFα antibody, or antigen-binding fragment thereof, of the invention can be used to treat osteoporosis.

10. Osteoarthritis

Tumor necrosis factor has been implicated in the pathophysiology of osteoarthritis, (Venn et al. (1993) *Arthritis Rheum.* 36:819; Westacott et al. (1994) *J Rheumatol.* 21:1710). Osteoarthritis (OA) is also referred to as hypertrophic osteoarthritis, osteoarthrosis, and degenerative joint disease. OA is a chronic degenerative disease of skeletal joints, which affects specific joints, commonly knees, hips, hand joints and spine, in adults of all ages. OA is characterized by a number of the following manifestations including degeneration and thinning of the articular cartilage with associated development of "ulcers" or craters, osteophyte formation, hypertrophy of bone at the margins, and changes in the snyovial membrane and enlargement of affected joints. Furthermore, osteoarthritis is accompanied by pain and stiffness, particularly after prolonged activity. The antibody, or antigen-binding fragment thereof, of the invention can be used to treat osteoarthritis. Characteristic radiographic features of osteoarthritis include joint space narrowing, subchondral sclerosis, osteophytosis, subchondral cyst formation, loose osseous body (or "joint mouse").

Medications used to treat osteoarthritis include a variety of nonsteroidal, anti-inflammatory drugs (NSAIDs). In addition, COX 2 inhibitors, including Celebrex, Vioxx, and Bextra, and Etoricoxib, are also used to treat OA. Steroids, which are injected directly into the joint, may also be used to reduce inflammation and pain. In one embodiment of the invention, TNFα antibodies of the invention are administered in combination with a NSAIDs, a COX2 inhibitor, and/or steroids.

11. Other

The methods of the invention, also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders, bone resorption disease, coagulation disturbances, burns, reperfusion injury, keloid formation, scar tissue formation, pyrexia, periodontal disease, obesity, radiation toxicity, age-related cachexia, Alzheimer's disease, brain edema, inflammatory brain injury, cancer, chronic fatigue syndrome, dermatomyositis, drug reactions, such as Stevens-Johnson syndrome and Jarisch-Herxheimer reaction, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, chronic otitis media with or without cholesteatoma, pediatric ear inflammation, myotosis, ovarian cancer, colorectal cancer, therapy associated with induced inflammatory syndrome (e.g., syndromes following IL-2 administration), and a disorder associated with a reperfusion injury.

It is understood that all of the above-mentioned TNFα-related disorders include both the adult and juvenile forms of the disease where appropriate. It is also understood that all of the above-mentioned disorders include both chronic and acute forms of the disease. In addition, the multiple-variable dose methods of the invention can be used to treat each of the above-mentioned TNFα-related disorders alone or in combination with one another, e.g., a subject who is suffering from uveitis and lupus.

IV. Pharmaceutical Compositions and Pharmaceutical Administration

A. Compositions and Administration

Antibodies, antibody-portions, and other TNFα inhibitors for use in the multiple-variable dose methods of the invention, can be incorporated into pharmaceutical compositions suitable for administration to a subject. Typically, the pharmaceutical composition comprises an antibody, antibody portion, or other TNFα inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, an antibody or antibody portion for use in the methods of the invention is coformulated with and/or coadministered with one or more additional therapeutic agents. For example, an anti-hTNFα antibody or antibody portion of the invention may be coformulated and/or coadministered with one or more DMARD or one or more NSAID or one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of a TNFα inhibitor and a pharmaceutically acceptable carrier, wherein the effective amount of the TNFα inhibitor may be effective to treat a TNFα-related disorder, including, for example, Crohn's disease, in a multiple variable dose regimen. In one embodiment, the antibody or antibody portion for use in the multiple variable dose methods of the invention is incorporated into a pharmaceutical formulation as described in PCT/IB03/04502 and U.S. application Ser. No. 10/222,140, incorporated by reference herein. This formulation includes a concentration 50 mg/ml of the antibody D2E7, wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is subcutaneous injection. In another embodiment, administration is via intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The TNFα antibodies of the invention can also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, incorporated by reference herein, are used to treat a TNFα-related disorder using the multiple-variable dose methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 10 to 200 mg, more preferably 20 to 160 mg, more preferably 40 to 80 mg, and most preferably 80 mg. In one embodiment, the therapeutically effective amount of an antibody or portion thereof for use in the methods of the invention is about 20 mg. In another embodiment, the therapeutically effective amount of an antibody or portion thereof for use in the methods of the invention is about 40 mg. In still another embodiment, the therapeutically effective amount of an antibody or portion thereof for use in the methods of the invention is about 80 mg. In one embodiment, the therapeutically effective amount of an antibody or portion thereof for use in the methods of the invention is about 120 mg. In yet another embodiment, the therapeutically effective amount of an antibody or portion thereof for use in the methods of the invention is about 160 mg. Ranges intermediate to the above recited dosages, e.g. about 78.5 to about 81.5; about 15 to about 25; about 30 to about 50; about 60 to about 100; about 90 to about 150; about 120 to about 200, are also intended to be part of this invention. For example, ranges of values using a combination of any of the above recited values as upper and/or lower limits are intended to be included.

The invention provides a multiple-variable dose method for treating a disorder in which TNFα activity is detrimental, comprising administering to a subject in need thereof at least one induction dose of a TNFα inhibitor, such as a human antibody, such that a threshold level of TNFα inhibitor is achieved within an induction phase, and subsequently administering to the subject a treatment dose of the human antibody within a treatment phase, such that treatment occurs.

The multiple-variable dose treatment method of the invention comprises administering a therapeutic agent in an induction phase, followed by a lower amount of the therapeutic agent during a treatment phase. In one embodiment, the induction dose comprises either 160 mg or 80 mg. In another embodiment, the induction dose ranges from about 20 to about 200 mg of a TNFα inhibitor. More preferably the induction dose ranges from about 40 to about 160 mg of a TNFα inhibitor. Most preferably the induction dose ranges from about 80 to about 160 mg of a TNFα antibody. The induction phase is complete once a threshold level of therapeutic agent is reached. The induction phase can include a single induction dose, or multiple induction doses wherein the same or different amounts of therapeutic agent are used. More than one induction dose may be administered during the induction phase, wherein any determined amount of time interval may occur between induction doses, including, for example, one hour apart, one day apart, one week apart, two weeks apart, etc. Examples of induction phase treatments of the invention used to achieve a threshold level of TNFα inhibitor include, but are not limited to, the following regimens: a 160 mg dose followed by an 80 mg dose; at least one dose of 160 mg dose; at least one dose of 80 mg dose; at least two doses of 80 mg dose; and two 80 mg induction doses at a one week interval.

A threshold level is achieved once a pre-determined therapeutic effect is reached. For example, the threshold level of a TNFα inhibitor for the treatment of Crohn's disease may be determined by monitoring a subject in the induction phase of treatment for a reduction in their CDAI index. In another example, the threshold level of a TNFα inhibitor for treatment of psoriasis may be determined by a decrease in psoriatic plaques, an improvement in the patient's Psoriasis Area Severity Index (PASI) score, or an improved Physician's Global Assessment (PGA) score. In still another example, the threshold level of a TNFα inhibitor for treatment of a TNFα-related disorder is determined by achievement of a stable blood plasma serum concentration of the TNFα inhibitor.

Once a threshold level is achieved, the treatment phase is initiated. At least one treatment dose is administered during the treatment phase. More than one treatment dose may administered during the treatment phase, wherein any determined amount of time interval may occur between induction doses, including, for example, one hour apart, one day apart, one week apart, two weeks apart, etc. In one embodiment, the treatment dose ranges from about 20 to about 120 mg of a TNFα inhibitor. Most preferably the treatment dose ranges from about 40 to about 80 mg of a TNFα inhibitor. In one embodiment, the treatment phase comprises administering 40 mg of a TNFα inhibitor. In another embodiment, the treatment phase comprises administering 80 mg of a TNFα inhibitor.

The multiple-variable dose method described herein is based on a treatment regimen which includes administration of at least two different doses of a TNFα inhibitor. The induction dose can be any multiple number greater than the treatment dose. For example, the induction dose can be two times greater than the treatment dose. In one embodiment of the invention, the induction dose is 160 mg, and the treatment dose is 80 mg. In another embodiment, the induction dose is 80 mg, and the treatment dose is 40 mg. In yet another embodiment, the induction dose is 70 mg, and the treatment dose is 35 mg. In another example, the treatment dose is 40% to 60% of the induction dose, e.g., the induction dose is 160 mg and the treatment dose ranges from 64 mg to 96 mg or the induction dose ranges from 80 mg and the treatment dose is 32 mg to 48 mg.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention also pertains to packaged pharmaceutical compositions or kits for administering the multiple-variable dose regimen of the invention. In one embodiment of the invention, the kit comprises a TNFα inhibitor, such as an antibody, and administration instructions according to the multiple-variable dose method for treatment. In one embodiment, the kit of the invention comprises an induction dose and/or a treatment dose for treatment of a particular disorder in which TNFα activity is detrimental. The kit may also include instructions relating to administration of the induction and/or treatment doses. The instructions may describe how, e.g., subcutaneously, and when, e.g., at week 0 and week 2, the different doses of TNFα inhibitor shall be administered to a subject for treatment. The instructions may also describe the administration of the TNFα inhibitor during the induction and the treatment phases of the multiple-variable dose treatment.

Kits to be used for the methods of the invention may include individual doses of a TNFα inhibitor which can be used in part, in whole, or in combination with one another to achieve the multiple-variable dose regimen. For example, the kit may include a number of prefilled syringes containing the TNFα antibody D2E7, wherein each syringe contains a 40 mg dose of the TNFα inhibitor. In one embodiment, multiple-variable dose therapy includes administration of a 160 mg induction dose of D2E7, followed by subsequent administration of an 80 mg dose of D2E7 at least two weeks following administration of the induction dose for the treatment of Crohn's disease. In such a case, the instructions would describe administration of four syringes of D2E7 for the induction dose, followed by administration of two syringes of D2E7 at least two weeks later. A kit of the invention for the treatment of Crohn's may also include a dose or doses of methotrexate for administration in combination with D2E7.

In another example, the kit of the invention may include doses of D2E7 for multiple-variable dose treatment of psoriasis. In one embodiment, the kit may contain at least one induction dose of 80 mg of D2E7, and at least one maintenance dose of 40 mg of D2E7. Instructions for administration of D2E7 for the treatment of psoriasis may include, for example, directions for administering one 80 mg dose, a second 80 mg dose a week later, and a 40 mg dose a week later and subsequently every other week. In another example, the instructions may include directions for a single 80 mg dose of D2E7, followed by a 40 mg treatment dose a week later and subsequently every other week.

Another aspect of the invention pertains to kits containing a pharmaceutical composition comprising an anti-TNFα antibody and a pharmaceutically acceptable carrier and one or more pharmaceutical compositions each comprising a drug useful for treating a TNFα-related disorder and a pharmaceutically acceptable carrier. Alternatively, the kit comprises a single pharmaceutical composition comprising an anti-TNFα antibody, one or more drugs useful for treating a TNFα-related disorder and a pharmaceutically acceptable carrier. The kits contain instructions for dosing of the pharmaceutical compositions for the treatment of a TNFα-related disorder in which the administration of an anti-TNFα antibody is beneficial, such as Crohn's disease or psoriasis.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

In one embodiment, the invention also provides a single dose method for treating a disorder in which TNFα activity is detrimental, comprising administering to a subject in need thereof a single dose of a TNFα inhibitor, such as a human antibody. In one embodiment, the TNFα inhibitor is the anti-TNFα antibody D2E7. The single dose of TNFα inhibitor can be any therapeutically or prophylactically effective amount. In one embodiment, a subject is administered either about 20 mg, 40 mg, or 80 mg single dose of D2E7. The single dose may be administered through any route, including, for example, subcutaneous administration.

B. Additional Therapeutic Agents

The invention pertains to pharmaceutical compositions and methods of use thereof for the treatment of a TNFα-related disorder using a multiple-variable dose regimen. The pharmaceutical compositions comprise a first agent that prevents or inhibits a TNFα-related disorder. The pharmaceutical composition and methods of use may comprise a second agent that is an active pharmaceutical ingredient; that is, the second agent is therapeutic and its function is beyond that of an inactive ingredient, such as a pharmaceutical carrier, preservative, diluent, or buffer. The second agent may be useful in treating or preventing TNFα-related disorders. The second agent may diminish or treat at least one symptom(s) associated with the targeted disease. The first and second agents may exert their biological effects by similar or unrelated mechanisms of action; or either one or both of the first and second agents may exert their biological effects by a multiplicity of mechanisms of action. A pharmaceutical composition may also comprise a third compound, or even more yet, wherein the third (and fourth, etc.) compound has the same characteristics of a second agent.

It should be understood that the pharmaceutical compositions described herein may have the first and second, third, or additional agents in the same pharmaceutically acceptable carrier or in a different pharmaceutically acceptable carrier for each described embodiment. It further should be understood that the first, second, third and additional agent may be administered simultaneously or sequentially within described embodiments. Alternatively, a first and second agent may be administered simultaneously, and a third or additional agent may be administered before or after the first two agents.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions. In certain embodiments, an antibody or antibody portion of the invention is coformulated with and/or coadministered with one or more additional therapeutic agents that are useful for treating TNFα-related disorder in which TNFα activity is detrimental. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies. Specific therapeutic agent(s) are generally selected based on the particular TNFα-related disorder being treated, as discussed below.

Nonlimiting examples of therapeutic agents with which an antibody, antibody portion, or other TNFα inhibitor can be combined in a multiple variable dose method of treatment of the invention include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kDTNFR-IgG/etanercept (75 kD TNF receptor-IgG fusion protein; Immunex; see e.g., *Arthritis & Rheumatism* (1994) Vol. 37, S295; *J. Invest. Med.* (1996) Vol. 44, 235A); 55 kDTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; Inflammation Research (1996) Vol. 45, pp. 103-107); tranexamic acid (inhibitor of plasminogen activation; see e.g., *Arthritis & Rheumatism* (1996) Vol. 39, No. 9 (supplement), S284);

T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα antibody of the invention to treat an TNFα-related disorder using the multiple variable dose or single dose method of treatments of the invention.

In one embodiment, the TNFα antibody of the invention is administered in combination with one of the following agents for the treatment of rheumatoid arthritis using the multiple variable dose method of treatment of the invention: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; anakinra (Kineret®/Amgen); leflunomide; naproxen; valdecoxib; sulfasalazine; ibuprofen; methylprednisolone; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; sulfadiazine; amitriptyline hcl; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, the TNFα antibody of the invention is administered using a multiple-variable dose method for the treatment of a TNFα related disorder in combination with one of the above mentioned agents for the treatment of rheumatoid arthritis. In another embodiment, the above-mentioned additional agents are used in combination with a TNFα antibody in the single dose method of treatment of the invention.

In one embodiment, the TNFα antibody of the invention is administered using the multiple variable dose regimen in combination with one of the following agents for the treatment of a TNFα-related disorder in which TNFα activity is detrimental: anti-IL12 antibody (ABT 874); anti-IL18 antibody (ABT 325); small molecule inhibitor of LCK; small molecule inhibitor of COT; anti-IL1 antibody; small molecule inhibitor of MK2; anti-CD19 antibody; small molecule inhibitor of CXCR3; small molecule inhibitor of CCR5; small molecule inhibitor of CCR11 anti-E/L selectin antibody; small molecule inhibitor of P2X7; small molecule inhibitor of IRAK-4; small molecule agonist of glucocorticoid receptor; anti-C5a receptor antibody; small molecule inhibitor of C5a receptor; anti-CD32 antibody; and CD32 as a therapeutic protein.

In yet another embodiment, the TNFα antibody of the invention is administered using the multiple variable dose regimen in combination with an antibiotic or antiinfective agent. Antiinfective agents include those agents known in the art to treat viral, fungal, parasitic or bacterial infections. The term, "antibiotic," as used herein, refers to a chemical substance that inhibits the growth of, or kills, microorganisms. Encompassed by this term are antibiotic produced by a microorganism, as well as synthetic antibiotics (e.g., analogs) known in the art. Antibiotics include, but are not limited to, clarithromycin (Biaxin®), ciprofloxacin (Cipro®), and metronidazole (Flagyl®).

In another embodiment, the TNFα antibody of the invention is administered using the multiple variable dose regimen in combination with an additional therapeutic agent to treat sciatica or pain. Examples of agents which can be used to reduce or inhibit the symptoms of sciatica or pain include hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, and temazepam.

In yet another embodiment, the TNFα-related disorder is treated using the multiple variable dose regimen with the TNFα antibody of the invention in combination with hemodialysis.

In another embodiment, a TNFα antibody of the invention is used in combination with a drug used to treat Crohn's disease or a Crohn's-related disorder in the multiple variable dose regimen of the invention. Examples of therapeutic agents which can be used to treat Crohn's include mesalamine, prednisone, azathioprine, mercaptopurine, infliximab, budesonide, sulfasalazine, methylprednisolone sod succ; diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, hyoscyamine sulfate, cholestyramine/sucrose, ciprofloxacin hydrochloride, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, natalizumab, methylprednisolone, interferon-gamma, and sargramostim (GM-CSF). In one embodiment, methotrexate is administered for the treatment of Crohn's disease at a dose of 2.5 mg to 30 mg per week.

In another embodiment, a TNFα antibody is administered in combination with an additional therapeutic agent to treat asthma in the multiple variable dose regimen of the invention. Examples of agents which can be used to reduce or inhibit the symptoms of asthma include the following: albuterol; salmeterol/fluticasone; sodium; fluticasone propionate; budesonide; prednisone; salmeterol xinafoate; levalbuterol hcl; sulfate/ipratropium; prednisolone sodium phosphate; triamcinolone acetonide; beclomethasone dipropionate; ipratropium bromide; Azithromycin; pirbuterol acetate; prednisolone; theophylline anhydrous; zafirlukast; methylprednisolone sod succ; clarithromycin; formoterol fumarate; influenza virus vaccine; methylprednisolone; trihydrate; allergy injection; cromolyn sodium; cefprozil; fexofenadine hydrochloride; flunisolide/menthol; levofloxacin; amoxicillin/clavulanate, inhaler assist device, guaifenesin, dexamethasone sod phosphate; moxifloxacin hcl; hyclate; guaifenesin/d-methorphan; gatifloxacin; pephedrine/cod/chlorphenir; cetirizine hydrochloride; mometasone furoate; salmeterol xinafoate; benzonatate; cephalexin; pe/hydrocodone/chlorphenir; cetirizine hcl/pseudoephed; phenylephrine/cod/promethazine; codeine/promethazine; flunisolide; dexamethasone; guaifenesin/pseudoephedrine; chlorpheniramine/hydrocodone; nedocromil sodium; terbutaline sulfate; epinephrine and methylprednisolone, metaproterenol sulfate.

In another embodiment, the TNFα □ antibody of the invention is administered in combination with an additional therapeutic agent to treat COPD in the multiple variable dose regimen of the invention. Examples of agents which can be used to reduce or inhibit the symptoms of COPD include, albuterol sulfate/ipratropium; ipratropium bromide; salmeterol/fluticasone; albuterol; salmeterol; xinafoate; fluticasone propionate; prednisone; theophylline anhydrous; levofloxacin; methylprednisolone sod succ; montelukast sodium; budesonide; formoterol fumarate; triamcinolone acetonide; guaifenesin; azithromycin; beclomethasone; dipropionate; levalbuterol hcl; flunisolide; sodium; trihydrate; gatifloxacin; zafirlukast; furoate; amoxicillin/clavulanate; flunisolide/menthol; chlorpheniramine/hydrocodone; metaproterenol sulfate; methylprednisolone; ephedrine/cod/chlorphenir; pirbuterol acetate; -ephedrine/loratadine; terbutaline sulfate; tiotropium bromide; (R,R)-formoterol; TgAAT; Cilomilast and Roflumilast In another embodiment, the TNFα antibody of the invention is administered in combination with an additional therapeutic agent to treat IPF in the multiple variable dose regimen of the invention. Examples of agents which can be used to reduce or inhibit the symptoms of IPF include prednisone; azathioprine; albuterol; colchicines; sulfate; digoxin; gamma interferon; methylprednisolone sod succ; furosemide; lisinopril; nitroglycerin; spironolactone; cyclophosphamide; ipratropium bromide; actinomycin d; alteplase; fluticasone propionate; levofloxacin; metaproterenol sulfate; morphine sulfate; oxycodone hcl; potassium chloride; triamcinolone acetonide; tacrolimus anhydrous; calcium; interferon-alpha; methotrexate; mycophenolate mofetil.

In one embodiment of the invention, a TNFα antibody is administered in combination with an agent which is commonly used to treat spondyloarthropathies in the multiple variable dose regimen of the invention. Examples of such agents include nonsteroidal, anti-inflammatory drugs (NSAIDs), COX 2 inhibitors, including Celebrex®, Vioxx®, and Bextra®, and etoricoxib. Physiotherapy is also commonly used to treat spondyloarthropathies, usually in conjunction with non-steroidal inflammatory drugs.

In another embodiment, the TNFα antibody of the invention is administered in combination with an additional therapeutic agent to treat ankylosing spondylitis in the multiple variable dose regimen of the invention. Examples of agents which can be used to reduce or inhibit the symptoms of ankylosing spondylitis include ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab.

In another embodiment, the TNFα antibody of the invention is administered in combination with an additional therapeutic agent to treat psoriatic arthritis in the multiple variable dose regimen of the invention. Examples of agents which can be used to reduce or inhibit the symptoms of psoriatic arthritis include methotrexate; etanercept; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; and efalizumab.

In one embodiment the TNFα inhibitor is administered following an initial procedure for treating coronary heart disease in the multiple variable dose regimen of the invention. Examples of such procedures include, but are not limited to coronary artery bypass grafting (CABG) and Percutaneous transluminal coronary balloon angioplasty (PTCA) or angioplasty. In one embodiment, the TNFα inhibitor is administered in order to prevent stenosis from re-occurring. In another embodiment of the invention, the TNFα inhibitor is administered in order to prevent or treat restenosis. The invention also provides a method of treatment, wherein the TNFα inhibitor is administered prior to, in conjunction with, or following the insertion of a stent in the artery of a subject receiving a procedure for treating coronary heart disease. In one embodiment the stent is administered following CABG or PTCA.

A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody, or, modular. Moreover, the stent graft may be adapted to release the drug at only the distal ends, or along the entire body of the stent graft. The TNFα inhibitor of the invention can also be administered on a stent. In one embodiment, the TNFα antibody of the invention, including, for example, D2E7/ HUMIRA® is administered by a drug-eluting stent.

The TNFα antibody can be administered in combination with an additional therapeutic agent to treat restenosis in the multiple variable dose regimen of the invention. Examples of agents which can be used to treat or prevent restenosis include sirolimus, paclitaxel, everolimus, tacrolimus, ABT-578, and acetaminophen.

The TNFα antibody of the invention can be administered in combination with an additional therapeutic agent to treat myocardial infarction in the multiple variable dose regimen of the invention. Examples of agents which can be used to treat or prevent myocardial infarction include aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, abciximab, and cariporide.

The TNFα antibody of the invention can be administered in combination with an additional therapeutic agent to treat angina in the multiple variable dose regimen of the invention. Examples of agents which can be used to treat or prevent angina include: aspirin; nitroglycerin; isosorbide mononitrate; atenolol; metoprolol succinate; metoprolol tartrate; amlodipine besylate; digoxin; dilitiazem hydropchloride; isosorbide dinitrate; clopidogrel bisulfate; nifedipine; atorvastatin calcium; potassium chloride; simvastatin; verapamil hcl; furosemide; propranolol hcl; carvedilo; lisinopril; sprionolactone; hydrochlorothiazide; enalapril maleate; madolol; ramipril; enoxaparin sodium; heparin sodium; valsartan; sotalol hydrochloride; fenofibrate; ezetimibe; bumetanide; losartan potassium; lisinopril/hydrochlorothiazide; felodipine; captopril; and bisoprolol fumarate.

In one embodiment of the invention, a TNFα antibody is administered in combination with an agent which is commonly used to treat hepatitis C virus in the multiple variable dose regimen of the invention. Examples of such agents include Interferon-alpha-2a, Interferon-alpha-2b, Interferon-alpha con1, Interfero-alpha-n1, Pegylated interferon-alpha-2a, Pegylated interferon-alpha-2b, Ribavirin, Peginterferon alfa-2b and ribavirin, Ursodeoxycholic Acid, Glycyrrhizic Acid, Thymalfasin, Maxamine, and VX-497.

The TNFα antibody of the invention is administered in combination with topical corticosteroids, vitamin D analogs, and topical or oral retinoids, or combinations thereof, for the treatment of psoriasis in the multiple variable dose regimen of the invention. In addition, the TNFα antibody of the invention is administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB and other phototherapy, and sulfasalazine.

An antibody, antibody portion, or other TNFα inhibitor of the invention can be used in combination with other agents to treat skin conditions in the multiple variable dose regimen of the invention. For example, an antibody, antibody portion, or other TNFα inhibitor of the invention is combined with PUVA therapy. PUVA is a combination of psoralen (P) and long-wave ultraviolet radiation (UVA) that is used to treat many different skin conditions. The antibodies, antibody portions, or other TNFα inhibitors of the invention can also be combined with pimecrolimus. In another embodiment, the antibodies of the invention are used to treat psoriasis, wherein the antibodies are administered in combination with tacrolimus. In a further embodiment, tacrolimus and TNFα inhibitors are administered in combination with methotrexate and/or cyclosporine. In still another embodiment, the TNFα inhibitor of the invention is administered with excimer laser treatment for treating psoriasis.

Nonlimiting examples of other therapeutic agents with which a TNFα inhibitor can be combined to treat a skin or nail disorder include UVA and UVB phototherapy in the multiple variable dose regimen of the invention. Other nonlimiting examples which can be used in combination with a TNFα inhibitor include anti-IL-12 and anti-IL-18 therapeutic agents, including antibodies.

In one embodiment, the TNFα antibody of the invention is administered in combination with an additional therapeutic agent in the treatment of Behcet's disease in the multiple variable dose regimen of the invention. Additional therapeutic agents which can be used to treat Behcet's disease include, but are not limited to, prednisone, cyclophosphamide (Cytoxan), Azathioprine (also called imuran, methotrexate, timethoprim/sulfamethoxazole (also called bactrim or septra) and folic acid.

Any one of the above-mentioned therapeutic agents, alone or in combination therewith, can be administered to a subject suffering from a TNFα-related disorder in which TNFα is detrimental, in combination with the TNFα antibody using a multiple variable dose treatment regimen of the invention. In one embodiment, any one of the above-mentioned therapeutic agents, alone or in combination therewith, can be administered to a subject suffering from rheumatoid arthritis in addition to a TNFα antibody to treat a TNFα-related disorder. It should be understood that the additional therapeutic agents can be used in combination therapy as described above, but also may be used in other indications described herein wherein a beneficial effect is desired.

It also is understood that the above-mentioned additional agents can also be used in combination with a TNFα inhibitor, e.g., a TNFα antibody, to treat a TNFα-related disorder using the single dose treatment method of the invention.

This invention is further illustrated by the following examples which should not be construed as limiting. The contents of all references, patents and published patent applications cited throughout this application are incorporated herein by reference

EXAMPLES

Example 1

Study of Efficacy of Multiple-Dose Therapy for Treatment of Crohn's Disease

Multiple-Variable Dose Treatment of Crohn's Disease with D2E7

Studies were performed to determine the efficacy of a multiple-variable dose regimen of a TNFα inhibitor, namely D2E7 (also referred to as adalimumab and Humira®), for treating Crohn's disease. Efficacy and tolerability of D2E7 in the treatment of patients with active Crohn's disease were evaluated in a randomized, double-blind, placebo-controlled, multicenter study.

In this study, two hundred ninety-nine patients without previous exposure to TNF-antagonists and with active Crohn's Disease were selected. Crohn's disease in each patient was confirmed by endoscopic or radiologic evaluation. Subjects were randomized equally to one of four treatment groups (three treatment groups and one placebo group). Eligible subjects included men and women between 18 and 75 years of age having a diagnosis of Crohn's disease for more than four months. In addition, selected patients had active Crohn's disease, defined as a Crohn's Disease Activity Index (CDAI) score of 220 to 450 points.

At baseline (Week 0), subjects received a loading dose of D2E7 followed by a treatment dose at Week 2, wherein the treatment dose was lower than the initial loading dose. Patients received one of the following multiple variable dose treatment regimens at Week 0 (baseline) and Week 2 (Week 0/Week 2): 160 mg/80 mg D2E7; 80 mg/40 mg D2E7; 40 mg/20 mg D2E7; or placebo/placebo. Patients were administered D2E7 or placebo treatment subcutaneously The study was conducted for up to ten weeks, including an initial two week screening period, a four week treatment period (Weeks 0 to 4), and a four week follow-up period. Participants were evaluated for induction of clinical remission of Crohn's disease, defined as a CDAI score of <150 at week 4. Clinical response, defined as a decrease in CDAI compared to the CDAI baseline reading of ≥70 [Δ70] or ≥100 points [Δ100]), was also assessed in the participants. Efficacy of the multiple-variable dose regimen was further measured according to improvements in the patient's Inflammatory Bowel Disease Questionnaire (IBDQ) score, and improvements or remission of draining fistulas. Fistula remission was defined as closure of all fistulas that were draining at baseline for at least two consecutive visits. Fistula improvement was defined as a decrease of ≥50% in the number of draining fistula for at least two consecutive visits. C-reactive protein (CRP) levels were also measured, as CRP levels are reflective of inflammation in the body.

Results from the study show that multiple, variable D2E7 dosage treatments were effective at inducing Crohn's disease remission. Table 1 shows the percentage of patients with clinical remission (CDAI<150) at week 4 of the dosing regimen. As shown below in Table 1, thirty percent of patients who received 80/40 mg or 160/80 mg of D2E7 achieved clinical remission compared with 12% who received placebo (p=0.004.) Patients in the highest dose group, 160/80 mg, achieved a statistically significant remission rate of 36% versus a placebo rate of 12%.

TABLE 1

D2E7 induces clinical remission in treatment groups at Week 4

|  | Placebo | 40/20 mg | 80/40 mg | 160/80 mg |
| --- | --- | --- | --- | --- |
| CDAI ≤ 150 | 12% | 18% | 24% | 36%* |

(*denotes p = 0.001)
(Placebo n = 74; 20 mg n = 74; 40 mg n = 75; 80 mg n = 76)

Results of remission of Crohn's disease (measured CDAI<150) from each dosage group are also shown in FIG. 1 (note dosage references in FIG. 1, as well as FIGS. 2-6 refer to the treatment dose, i.e., 40 mg refers to the 80/40 treatment regimen).

Figure 2:
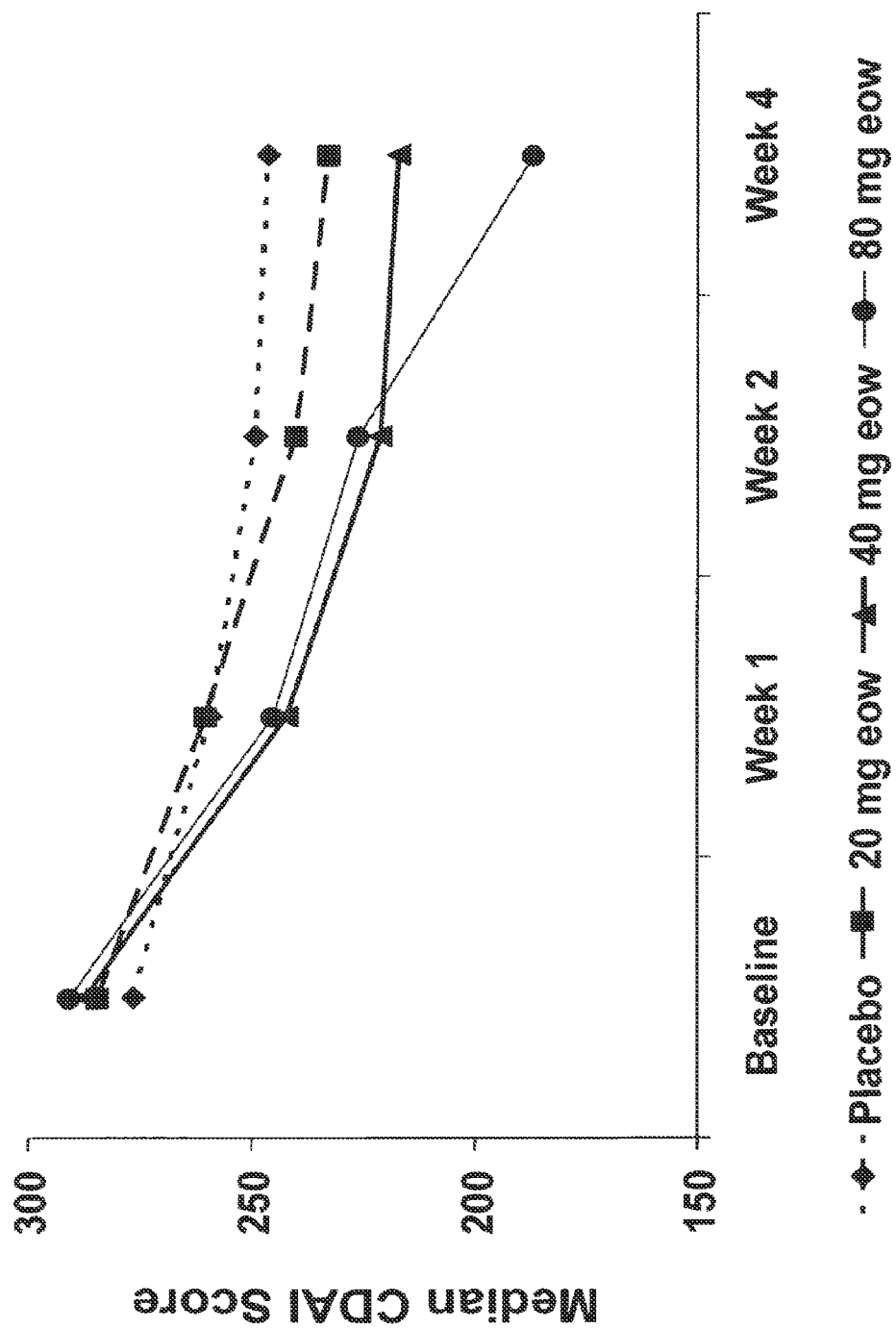
FIG. 2 shows a graph of the decrease in the mean CDAI score of Crohn's patients receiving the multiple variable dose regimens over time.
Figure 3A:
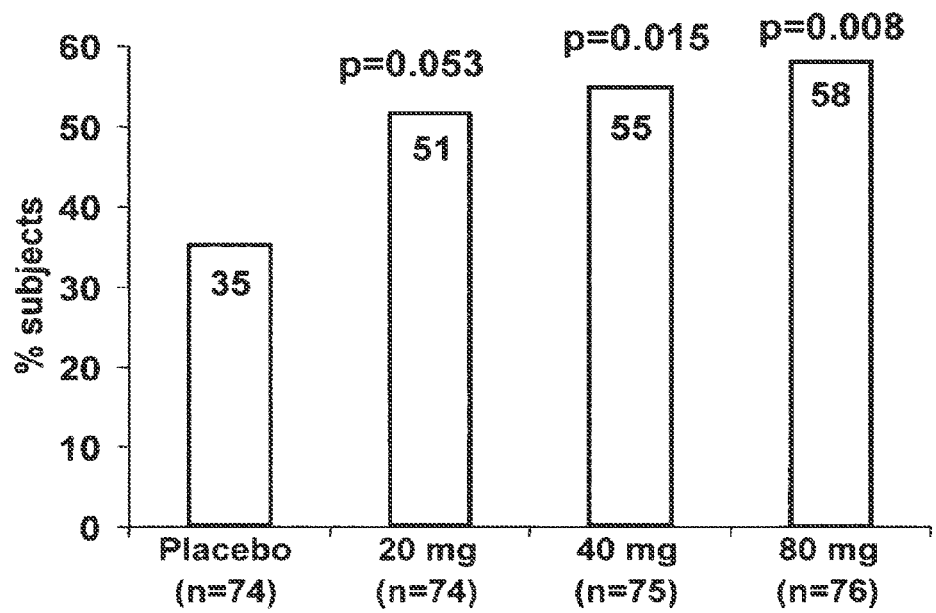
FIGS. 3A and 3B show remission and clinical response in Crohn's patients receiving multiple variable dose treatment.
Figure 3B:
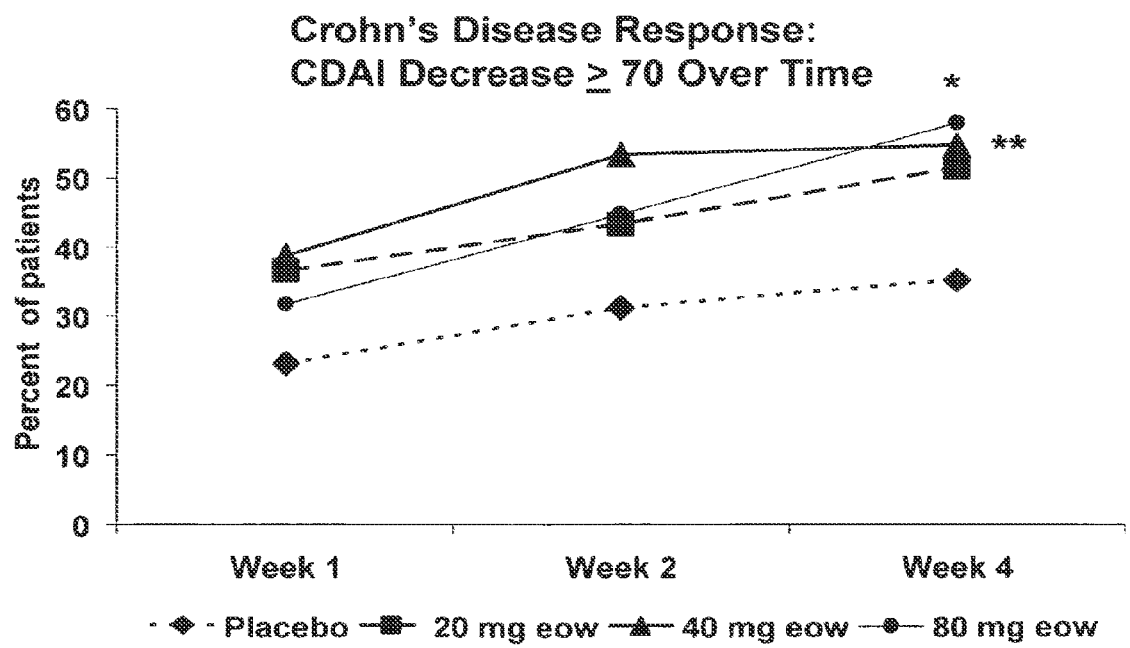
Figure 4A:
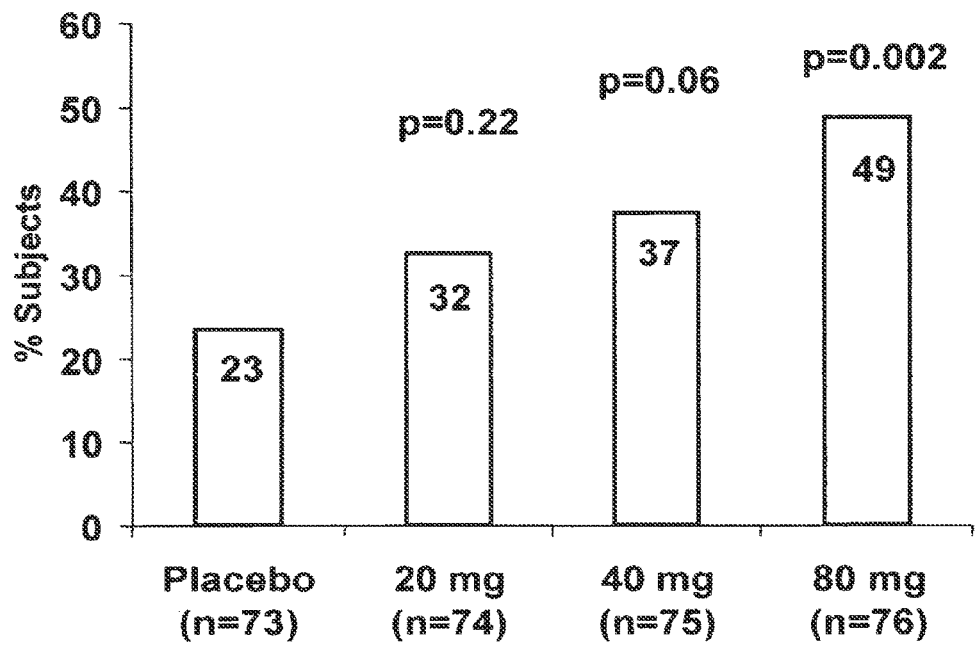
FIGS. 4A and 4B show remission and clinical response in Crohn's patients receiving multiple variable dose treatment.
Figure 4B:
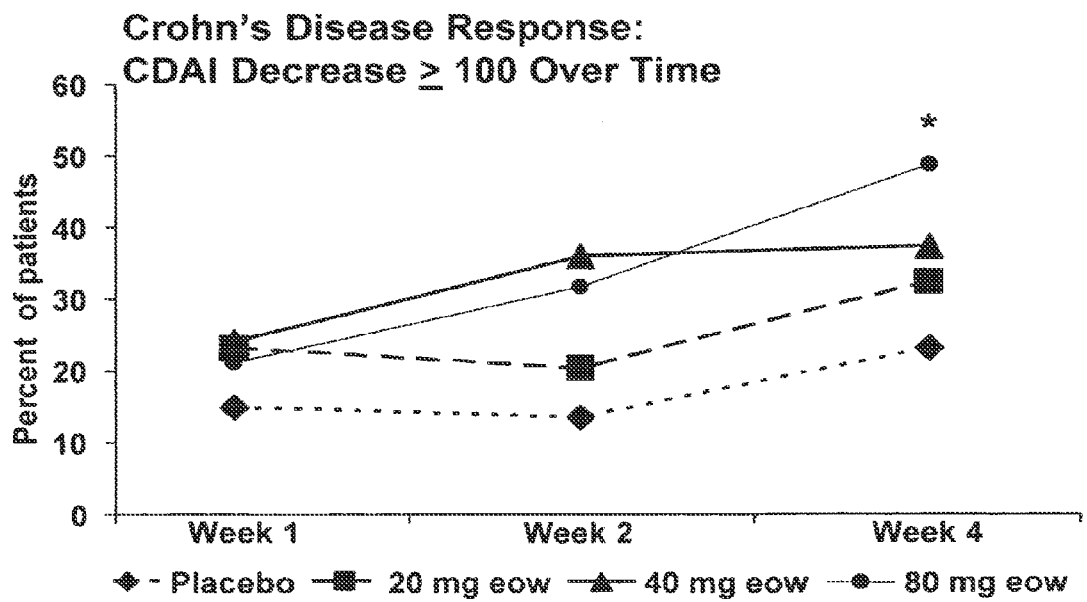
Figure 6:
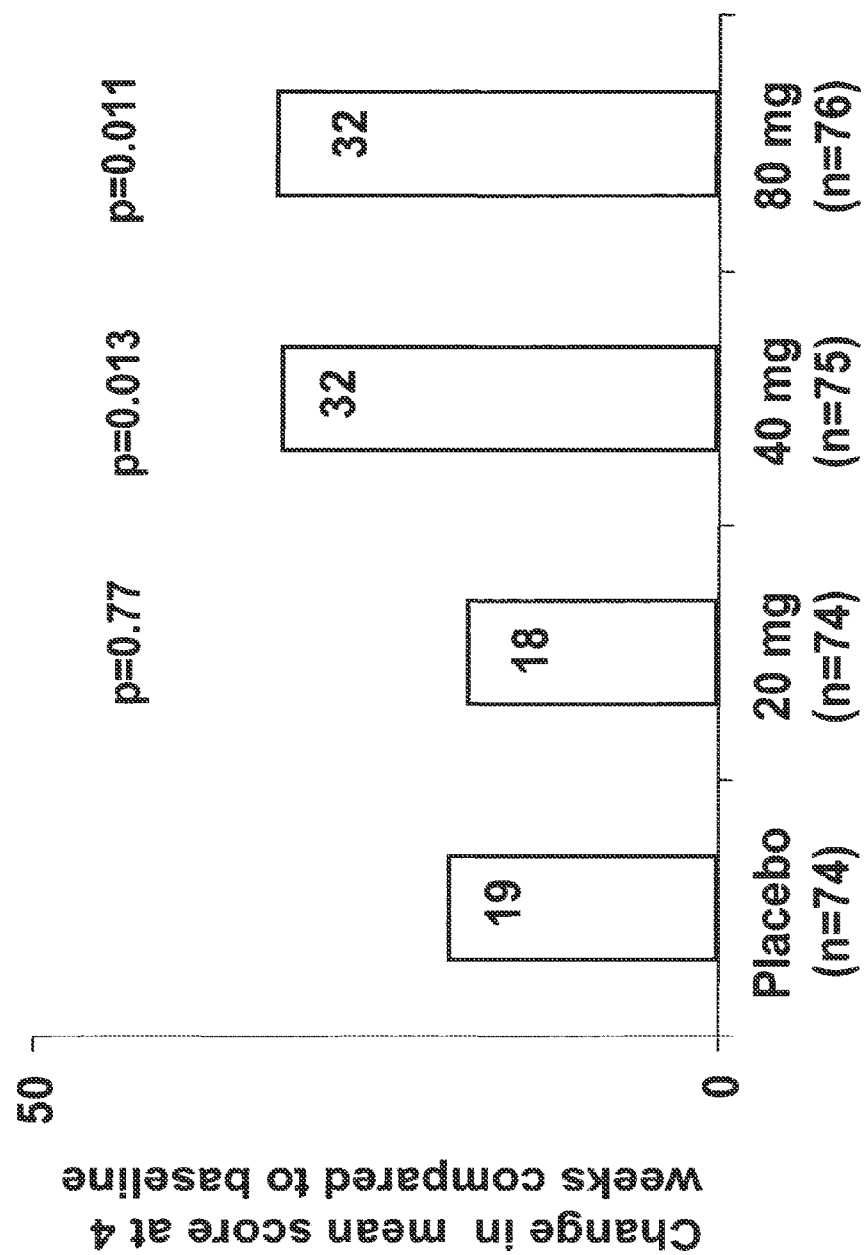
FIG. 6 provides results of the efficacy of the multiple-variable dose regimen at treating Crohn's disease as measured by the IBDQ score at four weeks (P-values represent comparison with placebo group).

The median 4-week changes in the CDAI index for each dose group (points with data at both baseline and week 4) were as follows: placebo, Δ−47 (n=67); 20 mg, Δ−73 (n=70); 40 mg, Δ−90 (n=70); and 80 mg, Δ−101 (n=73). The decrease in the CDAI index for patients who received the multiple variable dose treatment of D2E7 is also shown in FIG. 2. Clinical response results of CDAI≥70 point and ≥100 point decrease from baseline at four weeks are shown in FIGS. 3A and 3B (CDAI≥70) and FIGS. 4A and 4B (CDAI≥100). Thus, patients who received multiple, variable doses of D2E7, especially Crohn's patients receiving 80/40 mg and 160/80 mg, showed a decrease in the CDAI index indicating remission of Crohn's disease. In addition, as shown in FIG. 5, patients receiving the 160/80 mg dosing regimen showed the greatest decrease in CRP levels, with the placebo group showing the least decrease. Patients also showed an overall improvement in their IBDQ score, as shown in FIG. 6. In addition, sustained serum D2E7 concentrations were achieved early in treatment as a result of the multiple variable dose regimen.

The overall incidence of adverse events (AE) was low and did not differ among groups. The most common AE were injection site reactions, most of which were mild. Statistically significant results were not dependent on baseline CRP concentration.

In sum, multiple, variable doses of D2E7 significantly increased the frequency of remission of disease in Crohn's disease subjects. In combination, 30% of subjects receiving D2E7 doses of 80/40 mg and 160/80 mg achieved remission in comparison to only 12% of placebo subjects. There was also a significant increase in the clinical response (a decrease in the CDAI index of ≥70 points) and IBDQ scores of the 40 mg and 80 mg treatment doses every other week compared to the placebo. In the treatment group receiving an 80 mg D2E7 treatment dose every other week, 49% of the subjects achieved a clinical response (a decrease in the CDAI of ≥100 points).

Example 2

Additional Study of Efficacy of Multiple-Dose Therapy for Treatment of Crohn's Disease Multiple-Variable Dose Treatment of Crohn's Disease with D2E7

A study was performed to assess the tolerability and clinical benefit of a multiple-variable dose treatment using a TNFα inhibitor, specifically D2E7, in adult patients with Crohn's disease who had previously received and responded to a different TNFα inhibitor. The study included patients who had previously received the chimeric anti-TNF antibody infliximab, but who no longer have a sustained response and/or tolerance to infliximab.

Patients who had lost responsiveness or developed intolerance (acute or delayed infusion reactions) were treated with D2E7 80 mg at week 0 and 40 mg at week 2. All treatments were subcutaneous. Antibodies to infliximab (ATI) were determined at baseline (Prometheus Laboratories, San Diego, Calif.). Crohn's disease activity index (CDAI) scores, presence of fistulas, and C-reactive protein (CRP) concentration were determined at weeks 0 and 4. Clinical response (decrease in CDAI of $>/=100$ points), clinical remission (CDAI$</=150$ points), fistula improvement (closure $>/=50\%$ of open fistulas), complete fistula closure, and acute and delayed hypersensitivity reactions were recorded throughout the study.

Twenty-four patients were enrolled and completed 4 weeks of the multiple-variable dose therapy. Four of 16 patients (25%) were positive for ATI. Of 13 patients with week 0 CDAI scores $>/=220$, 6 (46%) achieved clinical response and 1 (8%) achieved remission at week 4. Of 6 patients with perianal and/or rectovaginal fistulas, 4 (67%) had fistula improvement and 3 (50%) had complete fistula closure at week 4. Only 6 patients (38%) had CRP values above the normal range. Among all patients, the mean+/−SD CRP concentrations decreased from 17.0+/−29.3 mg/L at week 0 to 11.3+/−17.3 mg/L at week 4. No patients experienced acute or delayed hypersensitivity reactions during treatment with D2E7 (including 8 who previously experienced treatment-limiting acute hypersensitivity reactions and 3 who previously experienced delayed hypersensitivity reactions with infliximab).

In sum, multiple-variable dose treatment using D2E7 was well tolerated and was clinically beneficial in patients with Crohn's disease who had previously received and responded to infliximab, but who no longer had a sustained response to or could not tolerate infliximab.

Example 3

Efficacy of Multiple-Dose Therapy Using TNFα Inhibitor for Treatment of Psoriasis Multiple-Variable Dose Treatment of Psoriasis with D2E7

A study was performed to determine the efficacy of a multiple-variable dose regimen of D2E7 for treating psoriasis. Efficacy and tolerability of D2E7 in the treatment of patients with moderate to severe chronic plaque psoriasis were evaluated in a randomized, double-blind, placebo-controlled multicenter study.

In this study, one hundred forty-eight adult patients with a diagnosis of moderate to severe psoriasis for at least one year were selected to receive multiple-variable dose treatment. Patients were also selected based on an affected body surface area (BSA) of ≥5%. Subjects were randomized equally to one of three groups (two treatment groups and one placebo).

At baseline (Week 0) patients in both treatment groups received an induction dose of 80 mg of D2E7. Patients in the first treatment group subsequently received a treatment dose of 40 mg of D2E7 at week 1 followed by 40 mg every other week (eow) starting at week 3. Subjects in the second treatment group received an induction dose of 80 mg dose of D2E7 at Week 1 (following the initial 80 mg dose at Week 0) followed by a treatment dose of 40 mg of D2E7 weekly starting at week 2. The placebo group received only the placebo weekly starting at baseline. All treatment was administered subcutaneously (sc) with pre-filled syringes. A summary of the different regimens are described below in Table 2:

TABLE 2

| Psoriasis study regimens | |
|---|---|
| Regimen | Detailed description |
| A | D2E7 80 mg sc administered at Week 0 (baseline); D2E7 40 mg sc every other week administered starting at Week 1 through Week 11, with placebo administered on alternate weeks |
| B | D2E7 80 mg sc administered starting at Week 0 (baseline) and at Week 1 (80/80); D2E7 40 mg sc weekly administered starting at Week 2 through Week 11 |
| C | Placebo sc will be administered at baseline and then weekly through Week 11, with two injections given at Week 1 and Week 1 |

In order to maintain the blind study, all subjects received a total of 2 injections at baseline and week 1. During the remaining period of the study (weeks 2 through 12), subjects received one injection per week. The treatment dose per injection correlated to the dose regimen randomly assigned to each subject.

The PASI of the participants of the multiple-variable dose regimen was determined according to standard methods (see Fredriksson and Pettersson, supra and Marls et al., supra). The primary efficacy endpoint of the study was the percentage of subjects achieving a clinical response as defined by at least a 75% reduction in the PASI score (≥PAST 75) at Week 12.

Secondary efficacy measures included a static Physician's Global Assessment (PGA) of "clear" or "almost clear" at Week 12. PGA was determined according to a seven point scale used to measure the severity of psoriasis at the time of the physician's evaluation. Descriptions of the disease used included the following: severe=very marked plaque elevation, scaling, and/or erythema; moderate to severe=marked plaque elevation, scaling, and/or erythema; moderate=moderate plaque elevation, scaling, and/or erythema; mild to moderate=intermediate between moderate and mild; mild=slight plaque elevation, scaling, and/or erythema; almost clear=intermediate between mild and clear; and clear=no signs of psoriasis.

The results show that at Week 12, statistically significantly greater percentages of patients achieved a PASI 75 response or better on D2E7 than those on a placebo treatment. For patients receiving 40 mg treatment dose of D2E7 eow, 53% demonstrated a PASI of 75 or higher. In addition, 80% of patients receiving a 40 mg treatment dose of D2E7 weekly showed a PASI 75 or higher, compared to only 4% of the placebo treatment group (p<0.001 vs. placebo).

Figure 7:
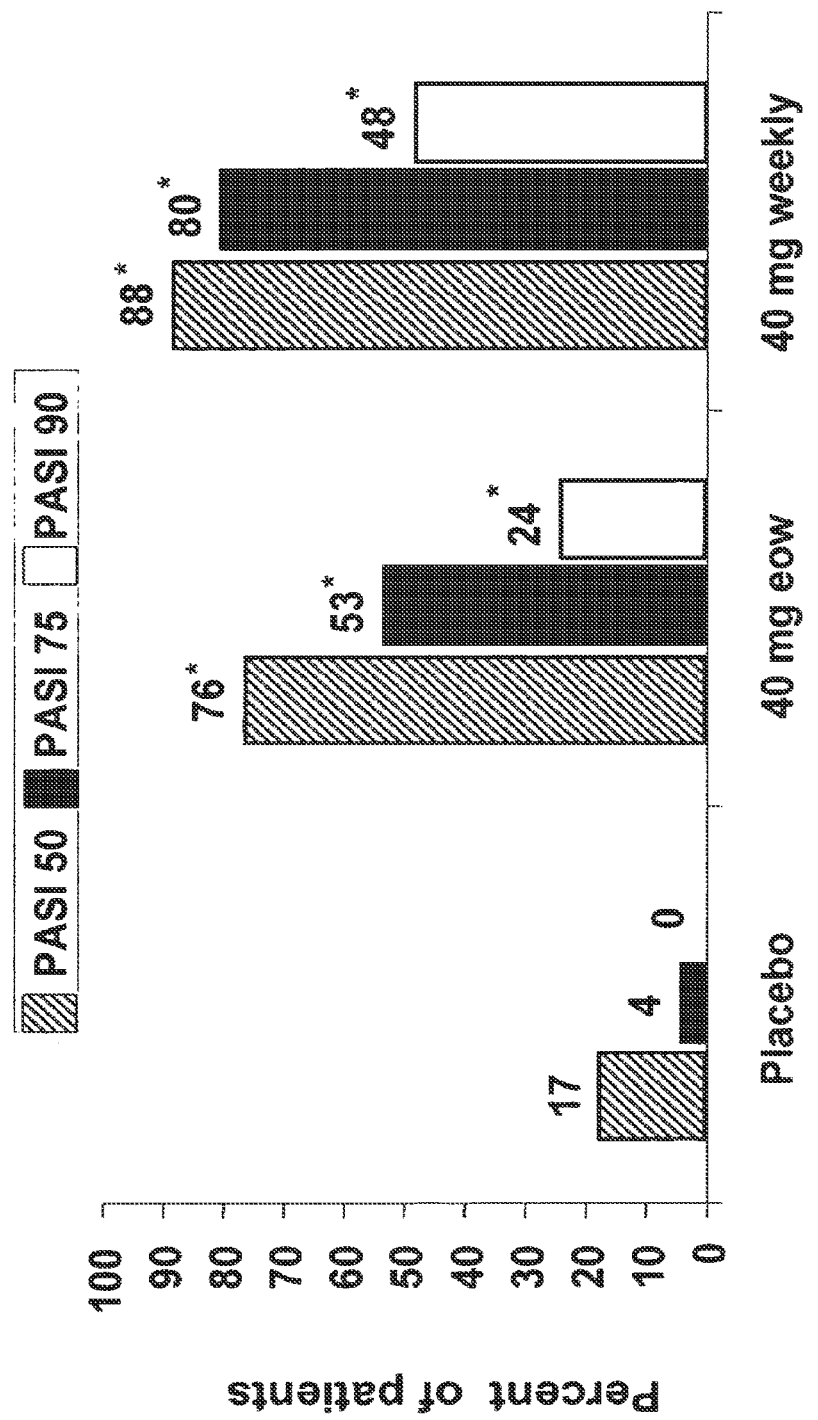
FIG. 7 shows the percentage of psoriasis patients with ≥PASI 50/75/90 response at week 12 following treatment with each multiple variable D2E7 dose and the placebo.

Response rates at Week 12 for both dosing regimens of D2E7 were statistically significantly greater than for placebo, as shown in FIG. 7.

Figure 8:
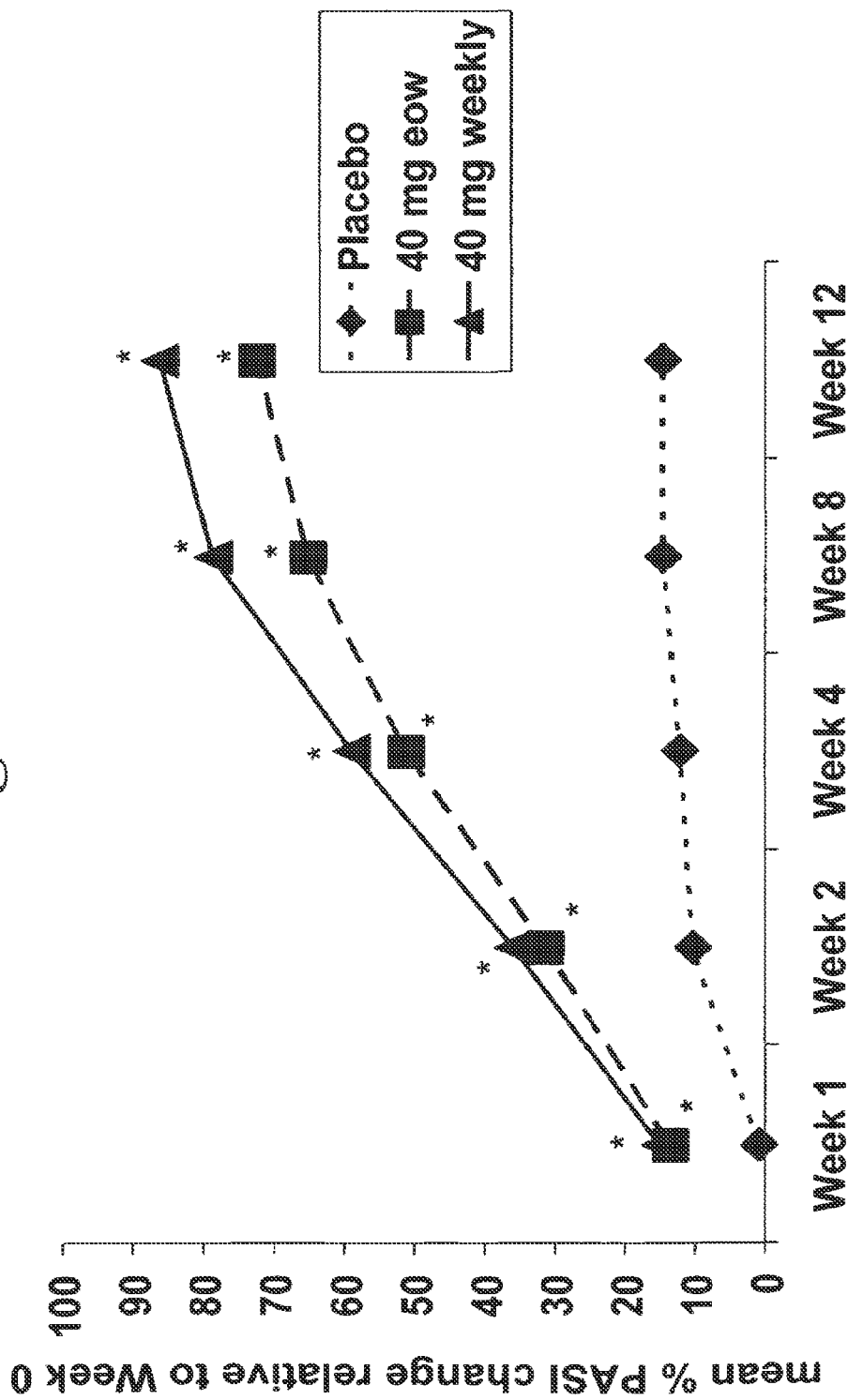
FIG. 8 provides results of the mean percentage PASI (Psoriasis Area and Severity Index) improvement over a 12 week treatment (eow=every other week; *=p<0.001 vs. placebo).

Overall, the mean percentage changes in PASI score for patients on D2E7 multiple-variable dose therapy were statistically significantly greater than placebo. The changes were evident as early as Week 1 after the initial dose, as shown in FIG. 8. At Week 12, 49% of patients on D2E7 receiving 40 mg eow and 76% of patients receiving 40 mg of D2E7 weekly achieved a PGA of "clear" or "almost clear," compared with 2% of placebo patients.

Figure 9:
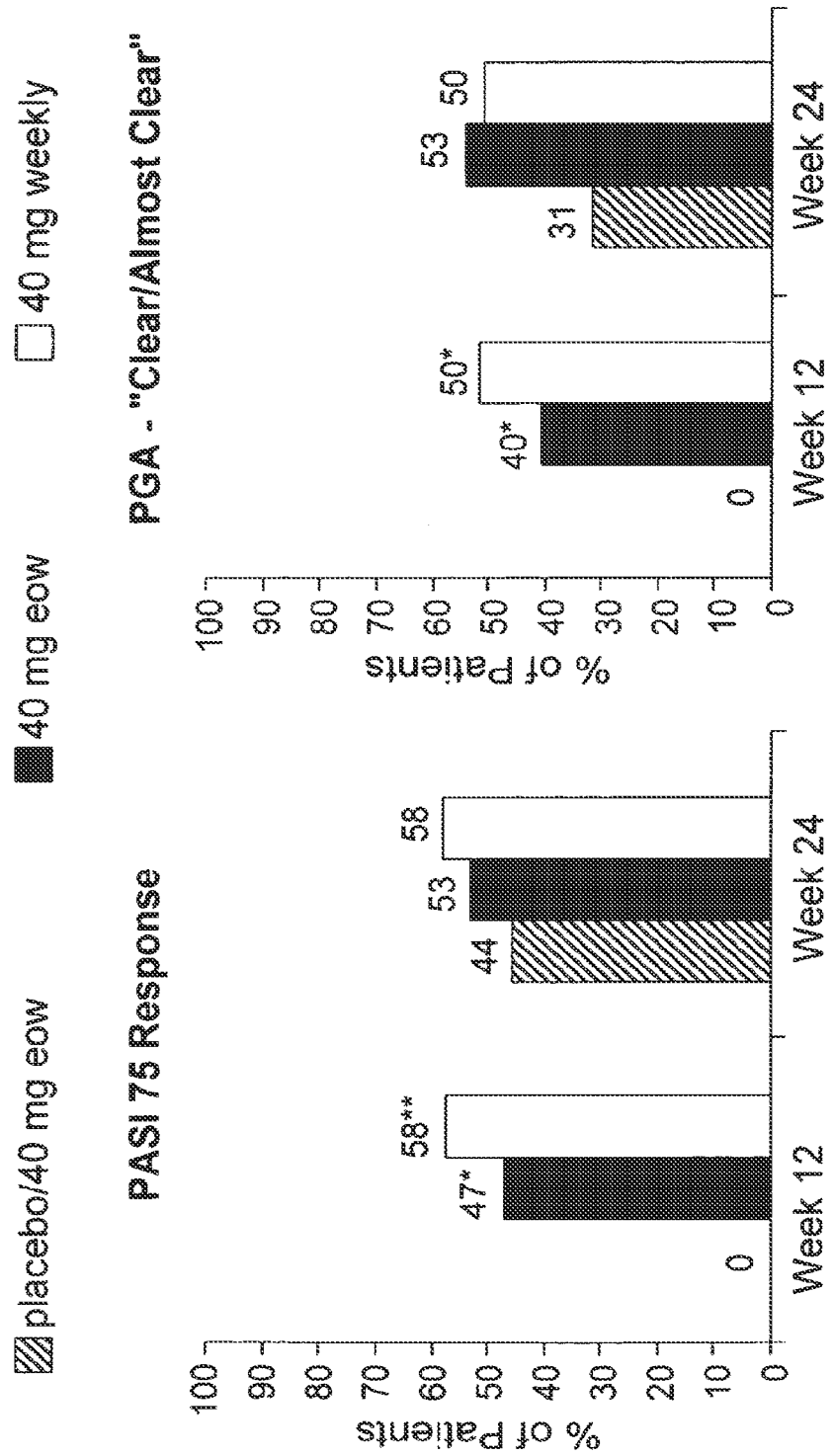
FIG. 9 shows a comparative graph of the efficacy response at week 12 and week 24 for patients with psoriasis and PsA.
Figure 10:
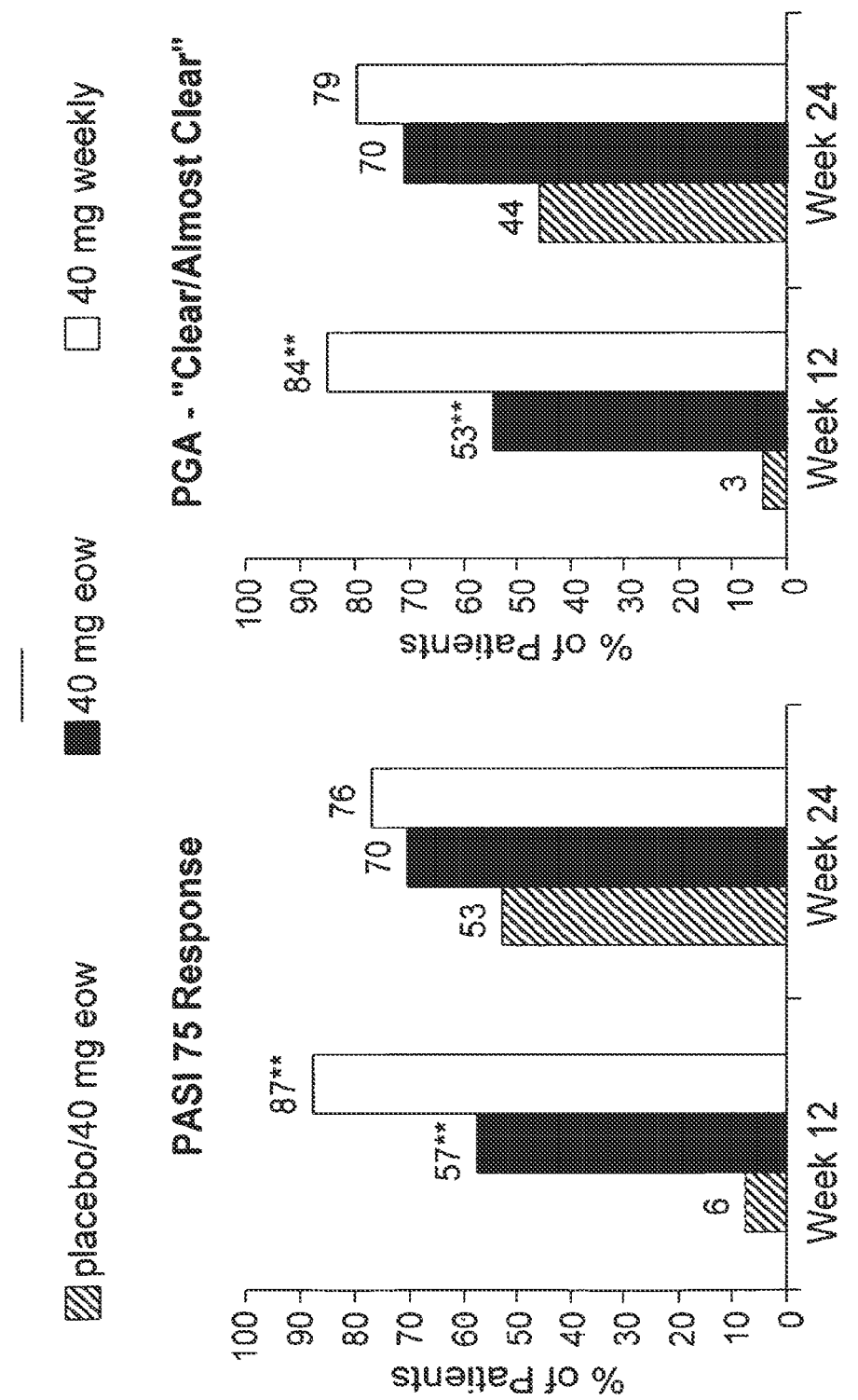
FIG. 10 shows a comparative graph of the efficacy response at week 12 and week 24 for patients with psoriasis and without PsA.

Of the one hundred forty-eight adult patients enrolled in the study, 29% also had a medical history of psoriatic arthritis (PsA). Both doses of D2E7 were effective in the treatment of psoriasis in both patients with and without PsA. Patients with PsA had a similar efficacy response to D2E7 as those without PsA. For both PsA and without PsA subgroups, the percentages of patients achieving a PASI 75 response or better at week 12 was statistically significant for the eow (with PsA, 47%; without PsA, 57%) and weekly treatment arms (with PsA, 58%; without PsA, 87%) compared with placebo. Continued improvements in efficacy were seen through week 24 in the eow arm (with PsA, 53%; without PsA, 70%). Efficacy responses in patients with and without PsA at weeks 12 and 24 are shown in FIGS. 9 and 10, respectively.

In conclusion, D2E7 administered for 12 weeks was effective in the treatment of moderate to severe chronic plaque psoriasis. 53% of patients on 40 mg eow achieved ≥PASI 75, compared with 4% on placebo. 80% of patients on 40 mg weekly achieved ≥PASI 75. 49% and 76% of patients on D2E7 40 mg eow and 40 mg weekly, respectively, were "clear" or "almost clear" of their psoriasis. In addition, D2E7 was equally effective at treating psoriasis patients with and without PsA.

Example 4

Efficacy of Single Dose Treatment of D2E7

A study was performed to determine the efficacy of a single dose regimen of D2E7 for treating rheumatoid arthritis (RA). The objective of the study was to determine and compare the single-dose safety and efficacy of 3 subcutaneous (sc) doses (20, 40, or 80 mg) of D2E7 in Japanese and Caucasian subjects with RA.

D2E7 was administered as single sc doses (20, 40, or 80 mg) in 40 Japanese (in Japan) and 36 Caucasian (in US) subjects with RA, well-matched for moderate-to-severe baseline disease severity, in 2 separate clinical studies of similar design—open-label, parallel group. On Study Days 1, 15 and 29, safety evaluations included physical examinations, vital signs, and laboratory assessments to determine adverse events (AEs), and efficacy evaluations included CRP, Physician's and Subject's Assessment of Disease Activity, Subject's Assessment of Pain, Disability Index of the Health Assessment Questionnaire (DIHAQ), and tender and swollen joint counts.

Results from the study showed that all Japanese treatment groups had statistically significant improvements of all ACR components (except DIHAQ) on Day 15 and on Day 29 compared to Day 1. In the 3 Caucasian treatment groups, only the 80-mg treatment group exhibited a statistically significant improvement at Day 29 in all individual ACR components with the exception of the DIHAQ score. Although the study duration was only 29 days, ACR20 responses were achieved in 47.5% (19/40) of the Japanese patients and in 30.6% (11/36) of the Caucasian patients. In addition, the difference in frequency of subjects reporting AEs between treatment groups was not clinically relevant within each study. Interestingly, there was an increased incidence of AEs in Japanese subjects which may reflect racial differences or investigator cultural tendency to report.

The results demonstrate an improvement of comparable magnitude in RA signs and symptoms in both groups in this short-term study using a single dose treatment. These results also suggest similar safety of single-dose sc administration of ADA in Japanese and Caucasian subjects.

Forming part of the present disclosure is the appended Sequence Listing, the contents of which are summarized in the table below:

| SEQ ID NO: | ANTIBODY CHAIN | REGION | SEQUENCE TYPE |
| --- | --- | --- | --- |
| 1 | D2E7 | VL | amino acid |
| 2 | D2E7 | VH | amino acid |
| 3 | D2E7 | VL CDR3 | amino acid |
| 4 | D2E7 | VH CDR3 | amino acid |
| 5 | D2E7 | VL CDR2 | amino acid |
| 6 | D2E7 | VH CDR2 | amino acid |
| 7 | D2E7 | VL CDR1 | amino acid |
| 8 | D2E7 | VH CDR1 | amino acid |
| 9 | 2SD4 | VL | amino acid |
| 10 | 2SD4 | VH | amino acid |
| 11 | 2SD4 | VL CDR3 | amino acid |
| 12 | EP B12 | VL CDR3 | amino acid |
| 13 | VL10E4 | VL CDR3 | amino acid |
| 14 | VL100A9 | VL CDR3 | amino acid |
| 15 | VLL100D2 | VL CDR3 | amino acid |
| 16 | VLL0F4 | VL CDR3 | amino acid |
| 17 | LOE5 | VL CDR3 | amino acid |
| 18 | VLLOG7 | VL CDR3 | amino acid |
| 19 | VLLOG9 | VL CDR3 | amino acid |
| 20 | VLLOH1 | VL CDR3 | amino acid |
| 21 | VLLOH10 | VL CDR3 | amino acid |
| 22 | VL1B7 | VL CDR3 | amino acid |
| 23 | VL1C1 | VL CDR3 | amino acid |
| 24 | VL0.1F4 | VL CDR3 | amino acid |
| 25 | VL0.1H8 | VL CDR3 | amino acid |
| 26 | LOE7.A | VL CDR3 | amino acid |
| 27 | 2SD4 | VH CDR3 | amino acid |
| 28 | VH1B11 | VH CDR3 | amino acid |
| 29 | VH1D8 | VH CDR3 | amino acid |
| 30 | VH1A11 | VH CDR3 | amino acid |
| 31 | VH1B12 | VH CDR3 | amino acid |
| 32 | VH1E4 | VH CDR3 | amino acid |
| 33 | VH1F6 | VH CDR3 | amino acid |
| 34 | 3C-H2 | VH CDR3 | amino acid |
| 35 | VH1-D2.N | VH CDR3 | amino acid |
| 36 | D2E7 | VL | nucleic acid |
| 37 | D2E7 | VH | nucleic acid |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A multiple-variable dose method for treating idiopathic inflammatory bowel disease in a subject in need thereof, comprising subcutaneously administering to the subject:
   a 160 mg dose of a recombinant human anti-TNFα antibody administered to the subject within a day; and
   a 40 mg dose of the antibody administered to the subject within a day, wherein the 40 mg dose is administered two weeks following administration of the 160 mg dose;
   wherein the antibody comprises:
   a heavy chain comprising a CDR1 comprising the amino acid sequence of SEQ ID NO:8; a CDR2 comprising the amino acid sequence of SEQ ID NO:6; and a CDR3 comprising the amino acid sequence of SEQ ID NO:4; and
   a light chain comprising a CDR1 comprising the amino acid sequence of SEQ ID NO:7; a CDR2 comprising the amino acid sequence of SEQ ID NO:5; and a CDR3 comprising the amino acid sequence of SEQ ID NO:3.

2. The method of claim 1, wherein the heavy chain comprises a heavy chain variable region comprising the amino acid sequence of SEQ ID NO:2, and the light chain comprises a light chain variable region comprising the amino acid sequence of SEQ ID NO:1.

3. The method of claim 2, wherein the heavy chain comprises an IgG1 heavy chain constant region and the light chain comprises a kappa light chain constant region.

4. The method of claim 3, wherein the antibody is adalimumab.

5. The method of claim 1, wherein the method further comprises subcutaneously administering to the subject additional 40 mg doses of the antibody, wherein the 40 mg doses are administered two weeks apart.

6. The method of claim 5, wherein the heavy chain comprises a heavy chain variable region comprising the amino acid sequence of SEQ ID NO:2, and the light chain comprises a light chain variable region comprising the amino acid sequence of SEQ ID NO:1.

7. The method of claim 6, wherein the heavy chain comprises an IgG1 heavy chain constant region and the light chain comprises a kappa light chain constant region.

8. The method of claim 7, wherein the antibody is adalimumab.

9. The method of claim 1, wherein the subject has Crohn's disease.

10. The method of claim 1, wherein the subject has ulcerative colitis.

11. The method of claim 5, wherein the subject has Crohn's disease.

12. The method of claim 5, wherein the subject has ulcerative colitis.

13. The method of claim 1, wherein each dose is subcutaneously administered to the subject using a prefilled syringe.

14. The method of claim 5, wherein each dose is subcutaneously administered to the subject using a prefilled syringe.

15. A multiple-variable dose method for treating idiopathic inflammatory bowel disease in a subject in need thereof, comprising subcutaneously administering to the subject:
   a 160 mg dose of a recombinant human anti-TNFα antibody administered as a set of four 40 mg injections of the antibody administered to the subject within a day; and a 40 mg dose of the antibody administered to the subject within a day, wherein the 40 mg dose is administered two weeks following administration of the 160 mg dose;

wherein the antibody comprises:

a heavy chain comprising a CDR1 comprising the amino acid sequence of SEQ ID NO:8; a CDR2 comprising the amino acid sequence of SEQ ID NO:6; and a CDR3 comprising the amino acid sequence of SEQ ID NO:4; and a light chain comprising a CDR1 comprising the amino acid sequence of SEQ ID NO:7; a CDR2 comprising the amino acid sequence of SEQ ID NO:5; and a CDR3 comprising the amino acid sequence of SEQ ID NO:3.

16. The method of claim 15, wherein the heavy chain comprises a heavy chain variable region comprising the amino acid sequence of SEQ ID NO:2, and the light chain comprises a light chain variable region comprising the amino acid sequence of SEQ ID NO:1.

17. The method of claim 16, wherein the heavy chain comprises an IgG1 heavy chain constant region and the light chain comprises a kappa light chain constant region.

18. The method of claim 17, wherein the antibody is adalimumab.

19. The method of claim 15, wherein the method further comprises subcutaneously administering to the subject additional 40 mg doses of the antibody, wherein the 40 mg doses are administered two weeks apart.

20. The method of claim 19, wherein the heavy chain comprises a heavy chain variable region comprising the amino acid sequence of SEQ ID NO:2, and the light chain comprises a light chain variable region comprising the amino acid sequence of SEQ ID NO:1.

21. The method of claim 20, wherein the heavy chain comprises an IgG1 heavy chain constant region and the light chain comprises a kappa light chain constant region.

22. The method of claim 21, wherein the antibody is adalimumab.

23. The method of claim 15, wherein the subject has Crohn's disease.

24. The method of claim 15, wherein the subject has ulcerative colitis.

25. The method of claim 19, wherein the subject has Crohn's disease.

26. The method of claim 19, wherein the subject has ulcerative colitis.

27. The method of claim 15, wherein each subcutaneous injection or said 40 mg dose is administered to the subject using a prefilled syringe.

28. The method of claim 19, wherein each subcutaneous injection or said 40 mg dose is administered to the subject using a prefilled syringe.

* * * * *

UNITED STATES PATENT AND TRADEMARK OFFICE
CERTIFICATE OF CORRECTION

| | | |
|---|---|---|
| PATENT NO. | : 9,499,615 B2 | Page 1 of 1 |
| APPLICATION NO. | : 14/804164 | |
| DATED | : November 22, 2016 | |
| INVENTOR(S) | : Hoffman et al. | |

It is certified that error appears in the above-identified patent and that said Letters Patent is hereby corrected as shown below:

On the Title Page

(72) Inventors:
Please add --Albert Assad, Wilmington, DE (US)--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: D2E7 heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: D2E7 light chain variable region CDR3
<220> FEATURE:
<221> NAME/KEY: SITE
<222> LOCATION: 9
<223> OTHER INFORMATION: Xaa = Any Amino Acid

```
<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
<220> FEATURE:
<221> NAME/KEY: SITE
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8

Asp Tyr Ala Met His
1               5

<210> SEQ ID NO 9
<211> LENGTH: 107
```

```
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
```

<213> ORGANISM: Artificial Sequence
<220> FEATURE:
<223> OTHER INFORMATION: EP B12 light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence

```
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
```

```
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                   10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3
```

```
<400> SEQUENCE: 30

Ala Ser Tyr Leu Ser Thr Ser Ser Ser Leu Asp Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10

<210> SEQ ID NO 36
<211> LENGTH: 321
<212> TYPE: DNA
<213> ORGANISM: Artificial Sequence
<220> FEATURE:
<223> OTHER INFORMATION: D2E7 light chain variable region
```

```
<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc     60
tcctgtgcgg cctctggatt cacctttgat gattatgcca tgcactgggt ccggcaagct   120
ccagggaagg gcctggaatg ggtctcagct atcacttgga atagtggtca catagactat   180
gcggactctg tggagggccg attcaccatc tccagagaca acgccaagaa ctccctgtat   240
ctgcaaatga acagtctgag agctgaggat acggccgtat attactgtgc gaaagtctcg   300
taccttagca ccgcgtcctc ccttgactat tggggccaag gtaccctggt caccgtctcg   360
agt                                                                 363
```